US011878057B2

(12) United States Patent
Rotjan et al.

(10) Patent No.: US 11,878,057 B2
(45) Date of Patent: Jan. 23, 2024

(54) IMMUNOMODULATORY LIPOPOLYSACCHARIDE COMPOSITIONS

(71) Applicants: TRUSTEES OF BOSTON UNIVERSITY, Boston, MA (US); THE CHILDREN'S MEDICAL CENTER CORPORATION, Boston, MA (US); MINISTRY OF FISHERIES AND MARINE RESOURCES DEVELOPMENT, Tarawa (KI)

(72) Inventors: Randi Dawn Rotjan, Lincoln, MA (US); Anna Gauthier, Boston, MA (US); Aranteiti Tekiau, Boston, MA (US); Jonathan C. Kagan, Brookline, MA (US)

(73) Assignees: TRUSTEES OF BOSTON UNIVERSITY, Boston, MA (US); THE CHILDREN'S MEDCIAL CENTER CORPORATION, Boston, MA (US); MINISTRY OF FISHERIES AND MARINE RESOURCES DEVELOPMENT, Tarawa (KI)

(*) Notice: Subject to any disclaimer, the term of this patent is extended or adjusted under 35 U.S.C. 154(b) by 0 days.

(21) Appl. No.: 17/547,639

(22) Filed: Dec. 10, 2021

(65) Prior Publication Data
US 2022/0184206 A1 Jun. 16, 2022

Related U.S. Application Data

(60) Provisional application No. 63/124,340, filed on Dec. 11, 2020.

(51) Int. Cl.
| | | |
|---|---|---|
| *A61K 31/739* | (2006.01) | |
| *A61K 39/00* | (2006.01) | |
| *A61K 39/02* | (2006.01) | |
| *A61K 39/39* | (2006.01) | |

(52) U.S. Cl.
CPC .......... *A61K 39/39* (2013.01); *A61K 31/739* (2013.01); *A61K 39/02* (2013.01); *A61K 2039/55572* (2013.01); *A61K 2039/6087* (2013.01)

(58) Field of Classification Search
None
See application file for complete search history.

(56) References Cited

U.S. PATENT DOCUMENTS

2016/0082093 A1* 3/2016 Longenecker .......... A61K 9/127
424/185.1

OTHER PUBLICATIONS

Apicella et al. In: Methods in Enzymology, Academic Press Inc., pp. 241-252, 1994.*
Hoffman et al. (Carbohydrate Res. 347: 164-167, 2012.*
Deneke et al. Canadian J. Microbiol. 19: 1211-1217, 1973.*
Benediktsdottir et al. Int. J. System. Evolut. Microbiol. 50: 470-488, 2000.*
Bjornsson et al. J. Appl. Micobiol. 111: 17-25, 2011.*
Clark et al. Appl Environ Microbiol. Oct. 2021; 87(20): e00964-21, Abstract.*
Apicella. "Isolation and characterization of lipopolysaccharides." Bacterial Pathogenesis : Mar. 13, 2008.
Caroff et al. "Structural and functional analyses of bacterial lipopolysaccharides." Microbes and Infection 4(9): 915-926 Jul. 2002.
Di Lorenzo et al. "Lipid A structure and immunoinhibitory effect of the marine bacterium Cobetia pacifica Kmm 3879T." Eur. J. Org. Chem. 2707-2716 2018.
Ei Hamidi et al. "Microextraction of bacterial lipid A: easy and rapid method for mass spectrometric characterization." Journal of Lipid Research 46(8): (2005): 1773-1778 Jun. 1, 2005.
Facchini et al. "Structure-activity relationship in monosaccharide-based toll-like receptor 4 (TLR4) antagonists." Journal of Medicinal Chemistry 61(7): 2895-2909 Mar. 1, 2018.
Gregg et al. "Rationally designed TLR4 ligands for vaccine adjuvant discovery." MBio 8(3): 1-14 May 9, 2017.
Kokoulin et al. "Partial structure and immunological properties of lipopolysaccharide from marine-derived Pseudomonas stutzeri KMM 226." Antonie Van Leeuwenhoek 110(12):1569-1580 Jul. 1, 2017.
Lorenzo et al. "The deep-sea polyextremophile Halobacteroides lacunaris TB21 rough-type LPS: Structure and Inhibitory activity towards toxic LPS." Marine Drugs 15(7): 1-16 Jun. 27, 2017.
Li et al. "Influence of lipid A acylation pattern on membrane permeability and innate immune stimulation." Marine Drugs 11(9): 3197-3208 Jun. 30, 2013.
Matsuura. "Structural modifications of bacterial lipopolysaccharide that facilitate gram-negative bacteria evasion of host innate immunity." Frontiers in Immunology 104(4): 1-9 May 24, 2013.
Pizzuto et al. "Saturation of acyl chains converts cardiolipin from an antagonist to an activator of Toll-like receptor-4." Cellular and Molecular Life Sciences 76(18): 3667-3678 May 6, 2019.
Rietschel et al. "Bacterial endotoxin: molecular relationships of structure to activity and function." The FASEB Journal (82): 217-225 Feb. 1, 1994.
Scott et al. "Lipid A structural modifications in extreme conditions and identification of unique modifying enzymes to define the Toll-like receptor 4 structure-activity relationship." Biochimica et Biophysica Acta (BBA)-Molecular and Cell Biology of Lipids 1862(11): 1439-1450 Jan. 17, 2017.
Steimle et al. "Structure and function: Lipid A modifications in commensals and pathogens." International Journal of Medical Microbiology 306(5): 290-301 Mar. 2, 2016.

* cited by examiner

*Primary Examiner* — S. Devi
(74) *Attorney, Agent, or Firm* — NIXON PEABODY LLP; Ronald I. Eisenstein; Jeanne Jodoin

(57) ABSTRACT

Provided herein are lipid A molecules engineered from *Moritella* lipopolysaccharides and uses thereof.

9 Claims, 20 Drawing Sheets
(12 of 20 Drawing Sheet(s) Filed in Color)
Specification includes a Sequence Listing.

S1. CTD cast 1   S4. Te Terina   S7. Winslow (seastar)
S2. Te Marena    S5. Orona       S8. McKean
S3. Rawaki       S6. Winslow     S9. Carondelet Reef

| stimulatory (+/+) | non-stimulatory (-/-) | other (-/+) |
|---|---|---|
| CD14+/TLR4+ | CD14-/TLR4- | CD14-/TLR4+ |
| 9 | 24 | 17 |

IMMUNOMODULATORY LIPOPOLYSACCHARIDE COMPOSITIONS

CROSS-REFERENCE TO RELATED APPLICATIONS

This application claims benefit under 35 U.S.C. § 119(e) to U.S. Provisional Application No. 63/124,340, filed Dec. 11, 2020, the contents of which are incorporated herein by reference in their entirety.

GOVERNMENT SUPPORT

This invention was made with government support under Grant No NA170AR0110083, awarded by The National Oceanic and Atmospheric Administration, and Grant Nos. AI133524, AI093589, AI116550, and DK034854, awarded by The National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Feb. 2, 2022, is named 701586-099260US-PT_SL.txt and is 1,243 bytes in size.

FIELD OF THE INVENTION

The field of the invention relates to modulation of the immune system using lipid A molecules engineered from *Moritella* lipopolysaccharide.

BACKGROUND

The lipopolysaccharide (LPS) molecule of Gram-negative bacteria is composed of three distinct regions. The hydrophobic lipid A region anchors LPS to the bacterial outer membrane, whereas the water-soluble core oligosaccharide and O-antigen extend from the lipid A anchor into the aqueous extracellular space. Conventional lipid A derived from *Escherichia coli* is a potent stimulator of the immune system but is too strong to be used in modulation of the immune system in humans.

SUMMARY

The compositions and methods described herein are based, in part, on the discovery that lipid A molecules engineered from isolated lipopolysaccharides from a *Moritella* genus bacterium can be either immunostimulatory, weakly immunostimulatory or immune-silent when administered to a subject. That is, these lipid A molecules produce immune activation along a spectrum or continuum ranging from no activation to strong activation, thereby permitting one of skill in the art to modulate an immune response to a desired degree.

In some embodiments, these immunostimulatory lipid A molecules are weaker at inducing the immune system than conventional lipid A molecules (e.g., from *E. coli*), which permits them to be used in the setting of vaccines, vaccine adjuvants and immunomodulatory molecules, where *E. coli* lipid A cannot be used due to severe side effects. In addition, provided herein are lipid A molecules that do not raise a measurable immune response in a subject but retain their ability to naturally form micelles, making them a useful tool in the preparation of drug delivery particles or devices.

Accordingly, one aspect provided herein relates to a composition comprising: an immunostimulatory lipid A molecule engineered from a lipopolysaccharide (LPS) isolated from a bacterium of the genus *Moritella*.

In one embodiment of this aspect and all other aspects provided herein, the immunostimulatory lipid A molecule comprises five, six or seven acyl chains.

In another embodiment of this aspect and all other aspects provided herein, no more than one of the five, six or seven acyl chains comprises a length of at least 16 carbons (C16).

In another embodiment of this aspect and all other aspects provided herein, each of the five, six or seven acyl chains each comprise a length of 12-14 carbons (C12-C14).

In another embodiment of this aspect and all other aspects provided herein, the lipid A molecule further comprises a bisphospho-di-glucosamine moiety.

In another embodiment of this aspect and all other aspects provided herein, the lipid A is capable of activating Toll-like receptor signaling, caspase signaling or a combination thereof.

In another embodiment of this aspect and all other aspects provided herein, the lipid A binds to Toll-like Receptor isoform 4 (TLR-4).

In another embodiment of this aspect and all other aspects provided herein, the bacterium of the genus *Moritella* is selected from the group consisting of: *Moritella* 5, *Moritella* 9, *Moritella* 10, *Moritella* 14, *Moritella* 18, *Moritella* 19, *Moritella* 20, *Moritella* 24 and *Moritella* 30.

Another aspect provided herein relates to a vaccine adjuvant or vaccine formulation comprising a *Moritella* lipid A or lipopolysaccharide composition as described herein.

In one embodiment of this aspect and all other aspects provided herein, the vaccine adjuvant or vaccine formulation further comprises a nucleic acid or polypeptide.

In another embodiment of this aspect and all other aspects provided herein, the nucleic acid comprises DNA, RNA, mRNA, dsDNA, dsRNA, siRNA, miRNA, or shRNA.

Another aspect provided herein relates to a method of inducing an immune response against an antigen in a subject, the method comprising: administering to a subject a vaccine comprising an antigen or a nucleic acid encoding an antigen in combination with an immunostimulatory lipid A engineered from a lipopolysaccharide (LPS) isolated from a bacterium of the genus *Moritella*, thereby inducing an immune response in the subject, wherein the immune response is increased by at least 10% compared to the vaccine comprising an antigen or nucleic acid encoding an antigen administered in the absence of the immunostimulatory lipid A.

In one embodiment of this aspect and all other aspects provided herein, the vaccine comprising the antigen or nucleic acid encoding the antigen and the immunostimulatory lipid A are in the same composition.

In another embodiment of this aspect and all other aspects provided herein, the vaccine comprising the antigen or nucleic acid encoding the antigen and the immunostimulatory lipid A are in different compositions.

In another embodiment of this aspect and all other aspects provided herein, the immunostimulatory lipid A molecule comprises five, six or seven acyl chains.

In another embodiment of this aspect and all other aspects provided herein, no more than one of the five, six or seven acyl chains comprises a length of at least 16 carbons (C16).

In another embodiment of this aspect and all other aspects provided herein, each of the five, six or seven acyl chains each comprise a length of 12-14 carbons (C12-C14).

In another embodiment of this aspect and all other aspects provided herein, the lipid A molecule further comprises a bisphospho-di-glucosamine moiety.

In another embodiment of this aspect and all other aspects provided herein, the lipid A activates Toll-like receptor signaling, caspase signaling or a combination thereof.

In another embodiment of this aspect and all other aspects provided herein, the lipid A binds to Toll-like Receptor isoform 4 (TLR-4).

In another embodiment of this aspect and all other aspects provided herein, the bacterium of the genus *Moritella* is selected from the group consisting of: *Moritella* 5, *Moritella* 9, *Moritella* 10, *Moritella* 14, *Moritella* 18, *Moritella* 19, *Moritella* 20, *Moritella* 24 and *Moritella* 30.

Another aspect provided herein relates to a composition comprising: an immune-silent lipid A molecule engineered from a lipopolysaccharide (LPS) isolated from a bacterium of the genus *Moritella*.

In one embodiment of this aspect and all other aspects provided herein, the lipid A molecule comprises five, six or seven acyl chains.

In another embodiment of this aspect and all other aspects provided herein, at least one of the five, six or seven acyl chains comprises a length of at least 16 carbons (C16).

In another embodiment of this aspect and all other aspects provided herein, at least two of the five, six or seven acyl chains comprises a length of at least 16 carbons (C16).

In another embodiment of this aspect and all other aspects provided herein, the remaining acyl chains each comprise a length of 12-14 carbons (C12-C14).

In another embodiment of this aspect and all other aspects provided herein, the lipid A molecule engineered from a lipopolysaccharide comprises at least two acyl chains each having a length of at least 16 carbons is more immune-silent than a substantially similar lipid A molecule comprising one acyl chain having a length of at least 16 carbons.

In another embodiment of this aspect and all other aspects provided herein, the immune response is determined by measuring loss of CD14 or TLR-4 receptors from the surface of cells using flow cytometry.

In another embodiment of this aspect and all other aspects provided herein, the immune-silent lipid A does not activate Toll-like receptor signaling or caspase signaling.

In another embodiment of this aspect and all other aspects provided herein, the immune-silent lipid A engineered from a lipopolysaccharide (LPS) further comprises a phosphoethanolamine moiety.

In another embodiment of this aspect and all other aspects provided herein, the bacterium of the genus *Moritella* is selected from the group consisting of: *Moritella* 28 and *Moritella* 36.

Another aspect provided herein relates to a drug delivery composition comprising a *Moritella* immune-silent lipid A as described herein and an agent, wherein the drug delivery composition does not raise an appreciable immune response when administered to a subject.

In one embodiment of this aspect and all other aspects provided herein, the composition comprises a micelle or liposome.

In another embodiment of this aspect and all other aspects provided herein, the agent comprises a nucleic acid, a protein, a drug, a small molecule, or an imaging molecule.

In another embodiment of this aspect and all other aspects provided herein, the nucleic acid comprises DNA, RNA, mRNA, dsDNA, dsRNA, siRNA, miRNA, or shRNA.

Also provided herein, in another aspect, is a method for delivering an agent to a subject in need thereof, the method comprising: administering to a subject a drug delivery composition comprising an immune-silent lipid A engineered from a lipopolysaccharide (LPS) isolated from a bacterium of the genus *Moritella* and an agent, thereby delivering the agent to the subject without inducing an appreciable immune response in the subject.

Another aspect provided herein relates to a heterogeneous lipid A composition comprising: a plurality of heterogeneous lipid A molecules engineered from a heterogeneous mixture of lipopolysaccharides (LPS) isolated from at least one bacterium of the genus *Moritella*, wherein the composition comprises a greater proportion of lipid A molecules having C16 length acyl chains than lipid A molecules lacking C16 acyl chains and is immune-silent, or wherein the composition comprises a greater proportion of lipid A molecules lacking C16 length acyl chains than lipid A molecules having C16 acyl chains and is immune-stimulatory.

In one embodiment of this aspect and all other aspects provided herein, the heterogeneous mixture comprises a ratio of immune stimulatory: immune-silent lipid A or lipopolysaccharide of: 1:1, 1:2, 1:3, 1:4, 1:5, 1:6, 1:7, 1:8, 1:9, 1:10, 1:15, 1:20, 1:25, 1:50, 1:100, or 1:200.

In another embodiment of this aspect and all other aspects provided herein, the heterogeneous mixture comprises a ratio of immune-silent:immune stimulatory lipid A or lipopolysaccharide of: 1:1, 1:2, 1:3, 1:4, 1:5, 1:6, 1:7, 1:8, 1:9, 1:10, 1:15, 1:20, 1:25, 1:50, 1:100, or 1:200.

In one embodiment of this aspect and all other aspects provided herein, the immune response upon administration to a subject can be modulated based on the proportion of lipid A molecules having C16 length acyl chains as compared to lipid A molecules lacking C16 acyl chains.

Another aspect provided herein relates to a composition comprising: a weakly immunostimulatory lipid A molecule engineered from a lipopolysaccharide (LPS) isolated from a bacterium of the genus *Moritella*.

In one embodiment of this aspect and all other aspects provided herein, the weakly immunostimulatory lipid A molecule comprises five, six or seven acyl chains.

In another embodiment of this aspect and all other aspects provided herein, one of the five, six or seven acyl chains comprises a length of at least 16 carbons (C16).

In another embodiment of this aspect and all other aspects provided herein, the remaining acyl chains each comprise a length of 12-14 carbons (C12-C14).

In another embodiment of this aspect and all other aspects provided herein, the lipid A molecule further comprises a bisphospho-di-glucosamine moiety.

In another embodiment of this aspect and all other aspects provided herein, the lipid A is capable of activating Toll-like receptor signaling, caspase signaling or a combination thereof.

In another embodiment of this aspect and all other aspects provided herein, the lipid A binds to Toll-like Receptor isoform 4 (TLR-4).

In another embodiment of this aspect and all other aspects provided herein, the bacterium of the genus *Moritella* is selected from the group consisting of: *Moritella* 5, *Moritella* 9, *Moritella* 10, *Moritella* 14, *Moritella* 18, *Moritella* 19, *Moritella* 20, *Moritella* 24 and *Moritella* 30.

In another embodiment of this aspect and all other aspects provided herein, the weakly immunostimulatory lipid A induces an immune response when administered to a subject that is at least 20% less than an immune response when the subject is administered lipid A derived from *E. coli*.

Also provided herein, in another aspect, is a vaccine adjuvant or vaccine formulation comprising a weakly immunostimulatory lipid A molecule engineered from a lipopolysaccharide (LPS) isolated from a bacterium of the genus *Moritella*.

In one embodiment of this aspect and all other aspects provided herein, the vaccine adjuvant or vaccine formulation further comprises a nucleic acid or polypeptide.

In another embodiment of this aspect and all other aspects provided herein, the nucleic acid comprises DNA, RNA, mRNA, dsDNA, dsRNA, siRNA, miRNA, or shRNA.

Another aspect provided herein relates to a method of inducing an immune response against an antigen in a subject, the method comprising: administering to a subject a vaccine comprising an antigen or a nucleic acid encoding an antigen in combination with a weakly immunostimulatory lipid A engineered from a lipopolysaccharide (LPS) isolated from a bacterium of the genus *Moritella*, thereby inducing an immune response in the subject, wherein the immune response is increased by at least 10% compared to the vaccine comprising an antigen or nucleic acid encoding an antigen administered in the absence of the weakly immunostimulatory lipid A.

BRIEF DESCRIPTION OF THE FIGURES

This patent or application file contains at least one drawing executed in color. Copies of this patent or patent application publication with color drawing(s) will be provided by the Office upon request and payment of the necessary fee.

(FIG. 1B). Overview of the microbial community composition at Stations S1-S9 as determined by 16S rRNA amplicon analysis (FIG. 1C). Streak purified bacteria strains isolated and sequenced from seawater and substrates collected at S2-S5 (FIG. 1D). *Moritella* relative 16S amplicon abundance in seawater samples collected from different depths at stations S2-S5 (FIG. 1E).

FIGS. 6A-6D. MALDI-TOF MS spectra of *Moritella* lipid A generated using the FLAT technique (FIG. 6A). Relative fatty acid content in lipid A derived from silent and stimulatory *Moritella* as determined by gas chromatography-mass spectrometry (GC-MS) (FIG. 6B). Whole genome phylogeny of *Moritella* strains. The amino acid phylogeny was inferred using maximum likelihood from a concatenated alignment of 120 single copy genes [65] generated from the four newly-sequenced *Moritella* genomes (green squares) and other publicly available assemblies. Black dots on branches indicate bootstrap support >75% (FIG. 6C). Degree of sequence conservation for enzymes in the lipid A biosynthesis pathway. The maximum likelihood phylogeny at left is based on a concatenated amino acid alignment of the 10 indicated Lipid A biosynthesis enzymes from each genome. The heatmap depicts the % amino acid identity for each individual enzyme in the pathway, as compared to

Figure 6A:
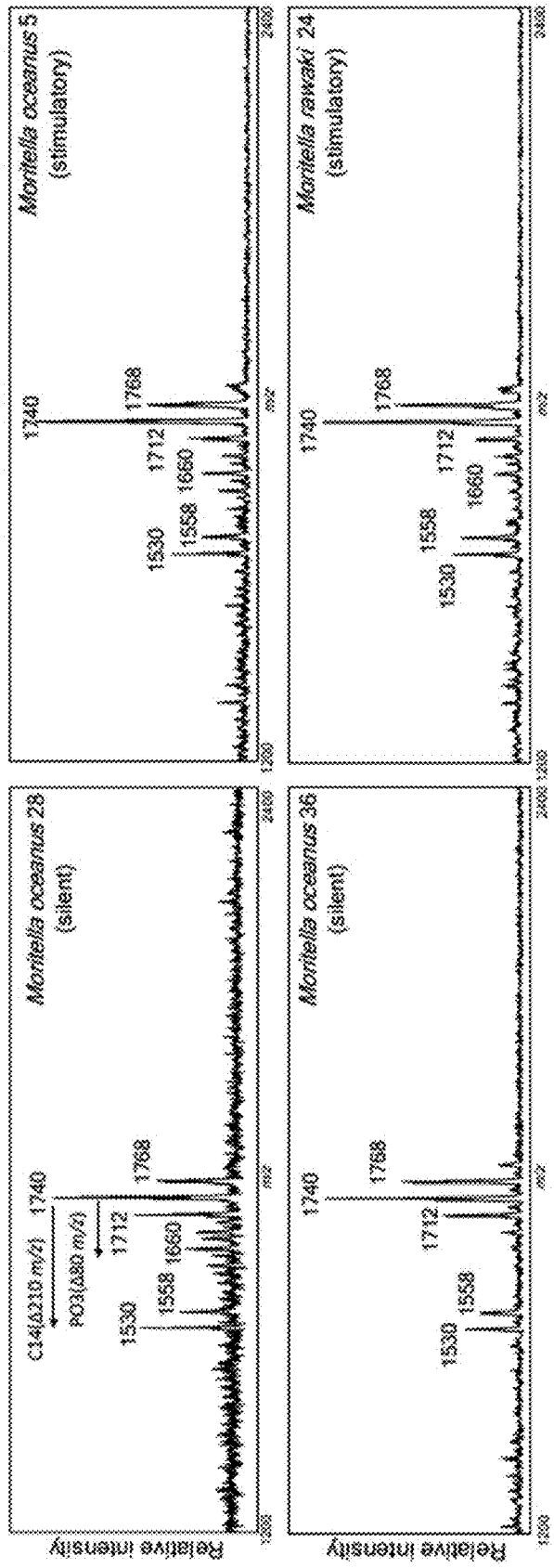
Figure 6B:
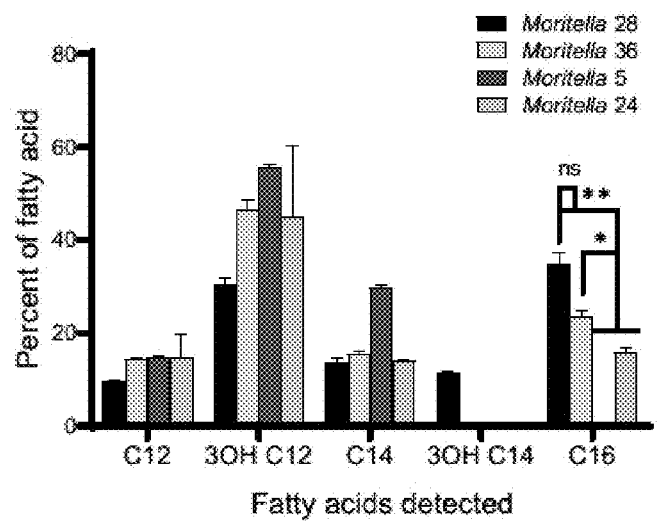

*Moritella oceanus* 28. Black dots on tree branches indicate bootstrap support >75% (FIG. 6D).

Figure 7:
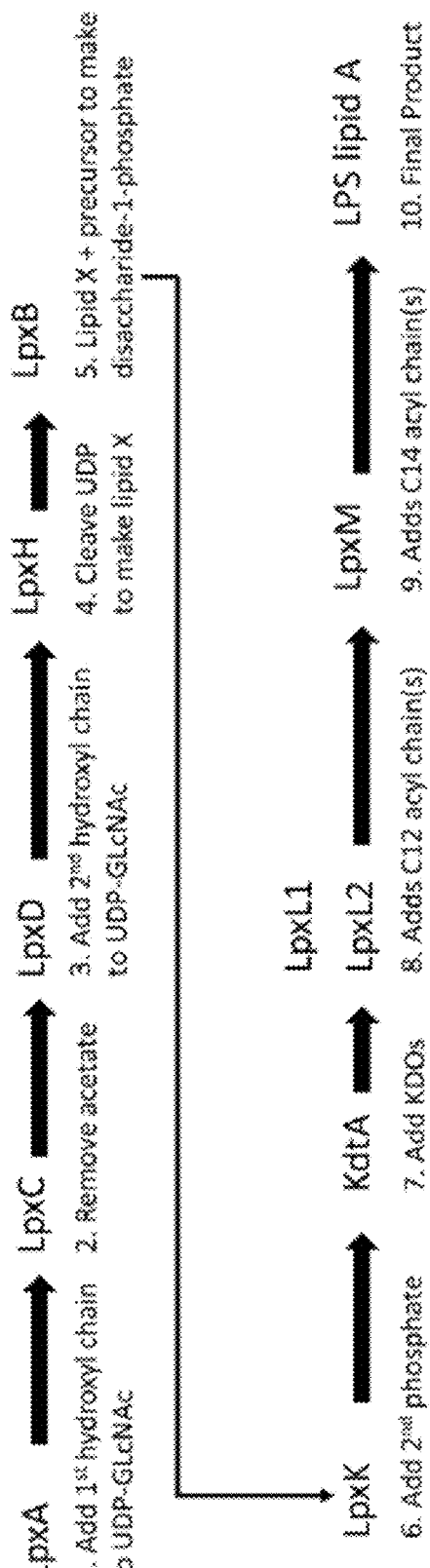

FIG. 7. A schematic representation of LPS lipid A biosynthesis pathway in Gram-negative bacteria [37].

Figure 8:
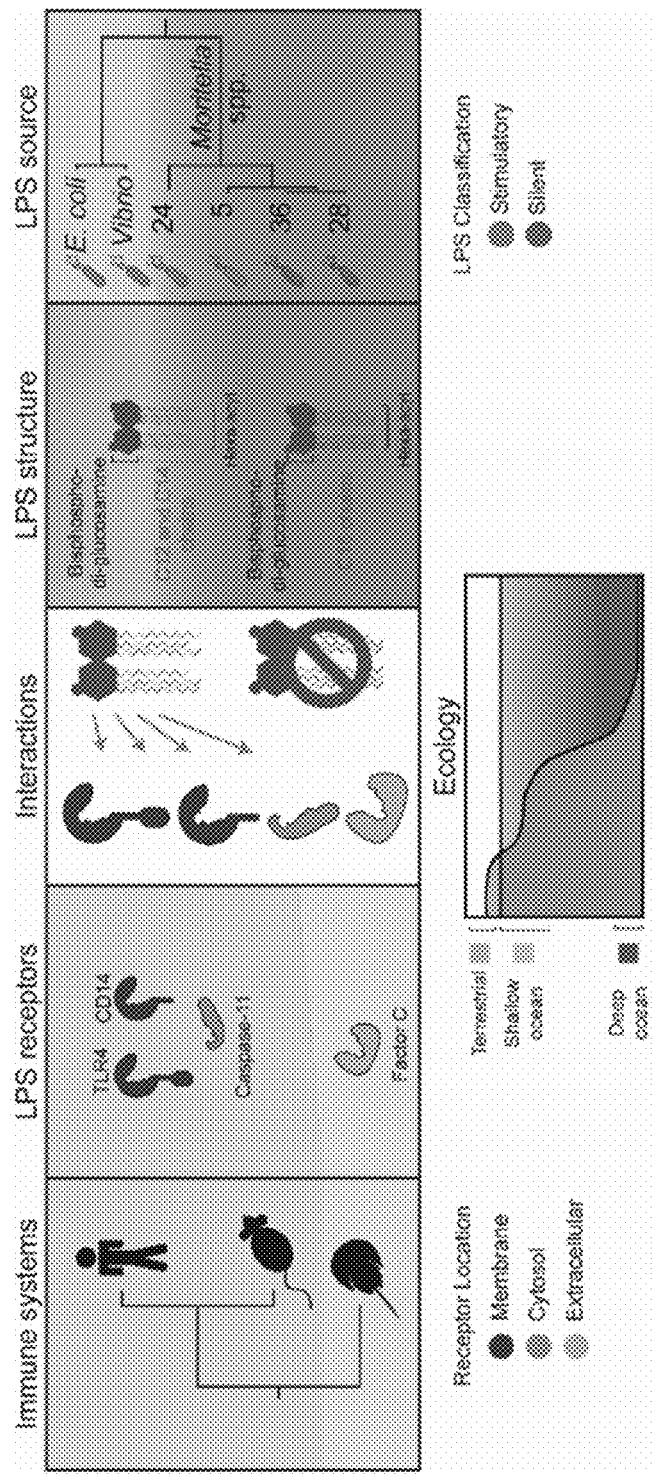

FIG. 8 *Moritella* LPS structure dictates PRR engagement in mice, humans, and horseshoe crabs (*L. polyphemus*). Membrane bound (TLR4, CD14) and intracellular (caspase-11) PRRs from terrestrial mammals (mice and humans) do not engage with LPS derived from deep-sea *Moritella* containing high concentrations of C16 secondary acyl chains on its lipid A. Likewise, the extracellular PRR (Factor C) from shallow water, ocean-dwelling horseshoe crabs does not engage with deep-sea *Moritella* LPS lipid A with high concentrations of C16 secondary acyl chains. There are no immuno-silent modifications to the bis-phosphorylated diglucosamine backbone, rather differences in secondary acyl chain length are reported and implicated in the immuno-silent phenotype observed for *Moritella oceanus* 28 and 36.

DETAILED DESCRIPTION

Provided herein are compositions and methods for modulating an immune response in a subject comprising engineered lipid A molecules derived from a *Moritella* genus of bacteria. Such lipid A molecules can modulate the immune system to varying degrees depending on the number of C16 acyl chains in the lipid A molecule. For example, a strong immunostimulatory effect is induced when the lipid A comprises acyl chains having a length of no more than 12-14 carbons (i.e., C8, C10, C12, C14), while lipid A molecules having at least two acyl chains having a length of at least 16 carbons (e.g., C16, C18, C20, C22, C24) are "silent" to the immune system. Lipid A molecules having a single acyl chain having a length of at least 16 carbons induce the immune system to a lesser degree than a lipid A comprising no C16 acyl chains but more than a lipid A comprising two C16 acyl chains (see e.g., FIG. 8).

Definitions

As used herein, the term "engineered from a *Moritella* LPS molecule" refers to the process of removing the O antigen and core oligosaccharide from the LPS molecule (as described in the working examples) and separating out the hydrophobic lipid A portion.

As used herein, the term "immunostimulatory lipid A molecule" refers to lipid A molecules that stimulate the immune system to some degree as assessed by using one or more assays known in the art or described herein in the working Examples (e.g., quantification of TNFα production and the phosphorylation of the transcription factor STAT1 from the plasma membrane or endosomes in the presence of a lipid A molecule). Typically, an immunostimulatory lipid A molecule comprises no more than one C16-length acyl chain and binds to one or both pattern recognition receptors that can also bind *E. coli* lipid A (e.g., CD14 and Toll-like receptor (e.g., TLR-4)). The degree of immune stimulation can vary along a continuum from weakly immunostimulatory to strongly immunostimulatory and the immune response is determined by the number of C16 length acyl chains.

"Weakly immunostimulatory" lipid A molecules derived from *Moritella* LPS have at least one C16 acyl chain and activate the immune system to a lesser degree than strongly immunostimulatory lipid A molecules derived from *Moritella*. Strongly immunostimulatory lipid A molecules typically have no acyl chains of C16 length or greater (e.g., all acyl chains are C12-C14 in length) and activate the immune system to a degree that is at least 80% similar to the immune activation in response to *E. coli* LPS (e.g., at least 85%, at least 90%, at least 95%, at least 98%, at least 99%, at least 100%, at least 105%, at least 110% of the immune activation in response to *E. coli* LPS) as assessed, for example, using the assays or reference values described in the working examples. In addition, "weakly immunostimulatory" lipid A molecules activate only one of the pattern recognition receptors (e.g., either CD14 or TLR-4, but not both) while strongly immunostimulatory lipid A molecules activate both pattern recognition receptors.

As used herein, the term "immune silent lipid A molecules" refers to lipid A molecules derived from *Moritella* LPS that do not substantially induce an immune response when administered to a subject. That is, administration of an immune silent lipid A molecule does not substantially activate the production of cytokines, chemokines, antibodies against lipid A and the like. In some embodiments, a parameter of immune activation induced by a composition comprising a *Moritella* lipid A molecule is increased by no more than 20% as compared to a substantially similar composition lacking the lipid A molecule (e.g., the lipid A molecule induces an activation that is no more than 15%, no more than 10%, no more than 5%, no more than 2%, no more than 1% or is below detectable limits of the assay as compared to the immune response of the same composition lacking the lipid A).

As used herein, the term "more immune silent" refers to the response of different *Moritella* lipid A molecules along an immune activation/immune silent continuum and refers to a *Moritella* lipid A molecule that induces immune cell activation to a lesser degree (e.g., less cytokine production or less antibody production by at least 10%) as compared to a second *Moritella* lipid A molecule. Typically, the more C16-length acyl chains that the *Moritella* lipid A molecule contains, the more immune silent it is along the continuum.

The term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—. An acyl group can be derived from an organic acid by removal of the hydroxy group. Examples of acyl groups include acetyl, propionyl, dodecanoyl, tetradecanoyl, isobutyryl, and the like. A preferred acyl group at positions C-2, C-3, C-2' and C-3' of the functionalized monosaccharides and disaccharides as described herein is an acyl group derived from fatty acid. A fatty acid can be saturated or non-saturated, and preferably contains from 4 to 28 carbon atoms.

As used herein, the term "inducing an immune response" refers to the induction of either an innate or adaptive immune response in a subject administered a lipid A molecule as described herein that is at least 20% greater than the innate or adaptive immune response in a subject that is administered a vehicle control lacking lipid A (e.g., at least 30%, at least 40%, at least 50%, at least 60%, at least 70%, at least 80%, at least 90%, at least 95%, at least 98%, at least 99%, at least 1-fold, at least 2-fold, at least 5-fold, at least 10-fold or more than the response induced by a substantially similar control lacking lipid A). Activation of an innate immune response can be determined by measuring the presence and/or level of one or more cytokines, chemokines, monokines, lymphokines, interleukins or tumor necrosis factor alpha (TNF-α). Activation of an adaptive immune response in a subject can be assessed by measuring the production/presence of antibodies against a vaccine antigen (e.g., neutralizing antibodies) or antibody titers thereof.

As used herein, the term "does not raise an appreciable immune response" refers to the lack of detectable immune activation parameters (e.g., less than 10%, 5%, or 1% immune activation as compared to a saline control) using standard assays known in the art or described herein in the examples section.

As used herein, the term "adjuvant" refers to a protein or chemical that, when administered with a vaccine antigen, enhances the immune response to the vaccine antigen. An adjuvant is distinguished from an antigenic moiety or carrier protein in that the adjuvant is not chemically coupled to the immunogen or the antigen, unless so desired. The immunostimulatory or weakly immunostimulatory lipid A molecules described herein can be used as an adjuvant in combination with a vaccine. The degree of immune stimulation or the strength of the lipid A adjuvant can be modulated from weakly immunogenic using a weakly immunostimulatory lipid A molecule as described herein, to strongly immunogenic using a strongly immunostimulatory lipid A molecule as described herein. In some embodiments, the lipid A vaccine adjuvant is a separate composition from a vaccine comprising an antigen or antigenic moiety. In other embodiments, the lipid A adjuvant is in the same composition as the antigen or antigenic moiety.

As used herein, the term "agent" is used to describe a bioactive molecule or precursor that can induce a desired effect on a cell or tissue. An agent can be a small molecule (i.e., a drug, a prodrug, a vitamin, a nutraceutical), endogenously occurring molecules (i.e., a growth factor, a cytokine, an enzyme, or a chemokine) an RNA interference molecule (e.g., siRNA, shRNA, or miRNA), or a diagnostic agent (i.e., a chromogenic agent, a luminogenic agent, or a fluorogenic agent). In one embodiment, the agent can be a cassette containing a promoter operably linked to a nucleic acid encoding a bioactive molecule.

As used herein, the term "targeting moiety" refers to a functional group which acts to target or direct a drug delivery particle and agent to a particular location, cell type, diseased tissue, or association, and permits concentration or accumulation at a given site. In general, the "targeting moiety" is directed against a target molecule and allows concentration of the compositions in a particular site within a subject. In certain embodiments, the targeting moiety can comprise a binding pair, antibodies, monoclonal antibodies, or derivatives or analogs thereof, including without limitation: Fv fragments, single chain Fv (scFv) fragments, Fab' fragments, F(ab')2 fragments, single domain antibodies, camelized antibodies and antibody fragments, humanized antibodies and antibody fragments, and multivalent versions of the foregoing; multivalent binding reagents including without limitation: monospecific or bispecific antibodies, such as disulfide stabilized Fv fragments, scFv tandems ((scFv)2 fragments), diabodies, tribodies or tetrabodies, which typically are covalently linked or otherwise stabilized (i.e., leucine zipper or helix stabilized) scFv fragments; and other targeting moieties include for example, aptamers, receptors, ligands, and fusion proteins.

The terms "decrease", "reduced", "reduction", or "inhibit" are all used herein to mean a decrease or lessening of a property, level, or other parameter by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase" or "enhance" or "activate" are all used herein to generally mean an increase of a property, level, or other parameter by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

The term "pharmaceutically acceptable" can refer to compounds and compositions which can be administered to a subject (e.g., a mammal or a human) without undue toxicity.

As used herein, the term "pharmaceutically acceptable carrier" can include any material or substance that, when combined with an active ingredient (e.g., a lipid A molecule derived from *Moritella* LPS), allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. The term "pharmaceutically acceptable carriers" excludes tissue culture media.

As used herein, the term "lipid A derivative" is inclusive of synthetic lipid As that are chemically identical to lipid As that are naturally occurring, and it also includes non-naturally occurring lipid A structures such as those obtainable by chemical or enzymatic synthesis.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean ±1%.

All references provided herein are incorporated by reference in their entirety.

Conventional Lipopolysaccharide (LPS) and Lipid A

Lipopolysaccharides (LPS) are molecules present in the outer membrane of gram negative bacteria and are involved in stabilizing the membrane structure. Structurally, conventional LPS molecules (e.g., from *E. coli*) comprise three domains: the O-antigen, a core oligosaccharide and lipid A. The O-antigen is the outermost portion of the LPS molecule and is a repetitive glycan polymer. The core oligosaccharide binds to both the O-antigen and to lipid A and comprises oligosaccharides (e.g., sugars) and non-carbohydrate components.

Lipid A is a hydrophobic domain, which structurally comprises a phosphorylated glucosamine disaccharide attached to multiple acyl chains (e.g., fatty acid chains). LPS is traditionally understood to have six acyl chains, four of which are attached directly to the glucosamine sugars, and two additional acyl chains attached to the beta hydroxy group. The fatty acids serve the function of retaining the LPS molecule in the bacterial membrane.

The structure of lipid A varies among bacterial species. The lipid A portion of the LPS molecule is responsible for a majority of a host's immune response. Conventional LPS molecules can strongly activate an immune response, leading to undesirable effects such as e.g., septic shock. Thus, previous studies have attempted to modulate the immune response by altering the structure of lipid A.

Immunomodulatory Lipid A molecules from *Moritella*

Provided herein are lipid A molecules derived from the *Moritella* genus of bacteria that can be used to modulate an immune response in a subject. For example, provided herein are lipid A molecules that produce a strong immune response (e.g., immunostimulatory lipid A), a weaker immune response (e.g., weakly immunostimulatory lipid A), or no discernable or measurable immune response (e.g., immune-silent lipid A).

In one embodiment, an immunostimulatory lipid A comprises a minimum of five, six, or seven acyl chains, wherein each of the acyl chains are no longer than 14 carbons in length (i.e., C14). In some embodiments, an immunostimulatory lipid A comprises acyl chains that are a mixture of C12 and C14 chains. It is specifically contemplated herein that immunostimulatory lipid A molecules can comprise shorter acyl chains (e.g., C6, C8, C10) or any mixture of C6, C8, C10, C12 and/or C14 chains (i.e., C6-C14).

Weakly immunostimulatory lipid A molecules differ from immunostimulatory lipid A molecules by the presence of a secondary acyl chain, which is indirectly attached to the glucosamine backbone and is 16 carbons in length (i.e., C16). The remaining acyl chains (e.g., 7 or higher, 4 or lower) can be of any length less than C16, but not including a C16 length. In some embodiments, the non-C16 acyl chains are C12, C14, or a mixture thereof.

Immune-silent lipid A molecules, as that term is used herein, comprise at least two C16-length acyl chains (e.g., 2, 3, 4, 5, 6, or 7). The other acyl chains can be of any desired length provided that they are shorter than C16. In some embodiments, the remaining acyl chains are C12 acyl chain, C14 acyl chains or a mixture thereof.

In some embodiments, such lipid A molecules can activate Toll-like receptor signaling (e.g., through TLR-4), caspase signaling or a combination of both. In some embodiments, it may be desirable to prepare a composition comprising a lipid A molecule that activates only one of the two major pathways (TLR-4 and caspase) that conventional LPS molecules activate, thereby modulating the immune response to a desired degree.

In some embodiments, the lipid A molecules are derived from one or more of the following *Moritella* bacterial species as recited in Table 3. In other embodiments, the lipid A molecules are derived from *Moritella oceanus*, or *Moritella rawaki*, as those terms are used herein. In one embodiment, the lipid A molecules are immune-silent and are derived from *Moritella* 28 or 36. In another embodiment, the lipid A molecules are immunostimulatory and are derived from *Moritella* 5, 9, 10 14, 18, 19, 20, 24 and 30.

The potency of a particular lipid A or derivative thereof, when used as an adjuvant or agonist to stimulate cytokine production, can be described by its EC50 value. The EC50 of a lipid A is the concentration of the lipid A at which 50% of the activity is produced. The EC50 value for a lipid A or derivative thereof can be determined using, for example, a cytokine production assay. When administered to stimulate cytokine production (e.g., as an adjuvant or agonist), the lipid A preferably exhibits an EC50 of less than about 100 nanomolar (100 nM). In a vaccine composition, an effective amount of a lipid A adjuvant is an amount that, when added to the vaccine, will enhance the magnitude or quality or duration of the immune response to the antigen(s) or immunogen(s) in the vaccine. An effective amount of lipid A for use as an adjuvant can be within the range of about 1 µg to about 1 mg See, e.g., LaPosta et al., US Pat Pub 20020025330 published Feb. 28, 2002.

In some embodiments, the LPS molecules from *Moritella* used to generate lipid A are generated by the bacteria, for example, in a bioreactor or batch cell culture system as known in the art. In some embodiments, LPS is generated in a system comprising *Moritella* bacteria. In alternative embodiments, an LPS or lipid A derivative that is substantially similar to the LPS molecules from *Moritella* and their corresponding lipid A can be chemically synthesized.

Lipid A can be produced from *Moritella* lipopolysaccharides using the methods described in the working examples.

Immune Responses

A host immune system aims to protect organisms from infection. The "innate" immune system provides an immediate, but non-specific response to infection by a pathogen. Some organisms, including humans, possess a second layer of protection, referred to herein as the "adaptive" immune system. The adaptive immune system provides an improved response that is retained after the pathogen has been eliminated, in the form of an immunological memory, and allows the adaptive immune system to mount faster and stronger attacks each time this pathogen is detected.

Adaptive Immune System and Response: The adaptive immune system permits regulation of the adaptive immune response by providing the vertebrate immune system with the ability to recognize and recall specific pathogens, and to mount a faster and/or stronger attack each time the pathogen is encountered. The system is highly adaptable because of somatic hypermutation (a process of accelerated somatic mutations), and V(D)J recombination (an irreversible genetic recombination of antigen receptor gene segments). This mechanism allows a small number of genes to generate a vast number of different antigen receptors, which are then uniquely expressed on each individual lymphocyte.

Thus, the adaptive immune response is typically understood to be an antigen-specific response of the immune system. Antigen specificity allows for the generation of responses that are tailored to specific pathogens or pathogen-infected cells. The ability to mount these tailored responses is usually maintained in the body by "memory cells".

In some embodiments, the lipopolysaccharides or lipid A engineered therefrom and described herein can induce an immune response, which can be measured by detecting the presence of or the titer of antibodies that can bind the *Moritella* lipopolysaccharides described herein.

Innate Immune System: The innate immune system refers to the cells and mechanisms that defend the host from infection by other organisms in a non-specific manner. Thus, the innate immune system does not confer long-lasting or protective immunity to the host. Typically, a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system; and/or acting as a physical and chemical barrier to infectious agents. The innate immune system can be, e.g., activated by ligands of Toll-like receptors (TLRs) or other auxiliary substances such as lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent.

Thus, in some embodiments, the *Moritella* lipid A or the lipopolysaccharides from which the lipid A is derived, can induce an innate immune response that can be measured by detecting an increase in at least one cytokine, monokine, lymphokine, interleukin or chemokine as described herein.

Vaccine Formulations

In some embodiments, the *Moritella* lipopolysaccharides or lipid A molecules derived therefrom can be used as an adjuvant. Such adjuvants can be administered separately from a vaccine composition or can be comprised within a vaccine composition. The *Moritella* lipopolysaccharide or lipid A molecules can be used with any vaccine including, for example, a protein vaccine, a polypeptide vaccine, an mRNA vaccine, an inactivated virus, a live-attenuated vaccine, a viral vector vaccine, a subunit vaccine, a recombinant vaccine, a conjugate vaccine, or a toxoid vaccine. In one embodiment, the *Moritella* lipopolysaccharide or lipid A molecules described herein are used in combination with an mRNA vaccine. The antigen comprised by the vaccine can be a viral antigen, a bacterial antigen, a cancer antigen or any other desired antigen or antigenic moiety.

In certain embodiments, *Moritella* lipopolysaccharide or lipid A molecules as described herein are used in combination with a nucleic acid vaccine (e.g., RNA or DNA vaccines). In one embodiment, the *Moritella* lipopolysaccharide or lipid A molecules are administered in combination with an mRNA vaccine or as part of an mRNA vaccine composition. The use of RNA (e.g., mRNA) reduces the risk of undesired genomic integration and generation of anti-DNA antibodies that can occur with DNA vaccines. However, RNA is considered to be a rather unstable molecular species. On the one hand, in the extracellular space, RNA is subject to degradation by almost ubiquitous RNAses. On the other hand, in vivo mRNA half-life in the cytoplasm is limited by the rate of enzymatic mRNA decay, which depends, at least in part, on cis-acting elements in the mRNA molecule. Thereby, controlled degradation of mRNA contributes to the fine regulation of eukaryotic gene expression (Friedel et al., Conserved principles of mammalian transcriptional regulation revealed by RNA half-life, Nucleic Acid Research, 2009, 1-12). Accordingly, each naturally occurring mRNA has its individual half-life depending on the gene, from which the mRNA is derived. In some embodiments, the *Moritella* lipopolysaccharide or lipid A molecules can be used in combination with an mRNA vaccine. In some embodiments, the *Moritella* lipopolysaccharide or lipid A molecules can be used to stabilize mRNA molecules within a vaccine composition. In some embodiments, the lipid A molecules described herein can be used to form micelles, or as components of a liposome or nanoparticle composition that can be used in combination with an mRNA encoding an antigen. In such embodiments, the mRNA can be encapsulated, attached to or associated with the micelle, liposome or nanoparticle composition.

Thus, in some embodiments, provided herein are RNA (e.g., mRNA) vaccines that include at least one RNA (e.g., mRNA) polynucleotide having an open reading frame encoding at least one antigenic polypeptide or an immunogenic fragment thereof (e.g., an immunogenic fragment capable of inducing an immune response to the antigenic polypeptide) and at least one *Moritella* lipopolysaccharide or lipid A molecule as described herein. As non-limiting examples, the RNA (e.g., mRNA) vaccines can be used to induce an immune response against a respiratory virus, such as hMPV, PIV, RSV, MeV, and/or BetaCoV (e.g., MERS-CoV, SARS-CoV, HCoV-OC43, HCoV-229E, HCoV-NL63, HCoV-NL, HCoV-NH and/or HCoV-HKU1), or any combination thereof.

In some embodiments, the immunity generated against a given antigen is long lasting (e.g., at least 2 years, at least 5 years, at least 10 years, at least 20 years, at least 30 years, at least 40 years, or even for the entire lifespan of the subject). Alternatively, in some embodiments, it is contemplated herein that the vaccine formulations as described herein are administered on an annual basis, tailored to prevalent or predicted prevalent strains of the target virus, analogous to immunization with the influenza vaccine, and can provide protection for at least 3 months from the last administration, at least 6 months, at least 8 months, at least one year, at least 1.5 years, or at least two years. The vaccine formulations described herein can prevent at least one of the symptoms associated with the viral or bacterial infection or can completely prevent presentation of any symptom. Common symptoms of a viral or bacterial infection can include, but are not limited to, fever, chills, cough, shortness of breath/difficulty breathing, fatigue, muscle/body aches, headache, new loss of taste or smell, sore throat, congestion or runny nose, nausea, vomiting, or diarrhea. A reduction in a symptom may be determined subjectively or objectively, e.g., self-assessment by a subject, by a clinician's assessment or by conducting an appropriate assay or measurement (e.g. body temperature, fluid in lungs, elevated heart rate, clinical PCR or antigen test etc.), including, e.g., a quality of life assessment, a slowed progression of infection or additional symptoms, a reduced severity of disease symptoms or a suitable assays (e.g. antibody titer, clinical PCR or antigen test and/or T-cell activation assay).

Vaccine formulations can comprise at least one antigen or nucleic acid encoding an antigen operably linked to a promoter that is microencapsulated or macroencapsulated using methods well known in the art (e.g., liposomes or micelles comprising a *Moritella* lipid A molecule). Other components of liposomes can comprise, for example, the inner capsid protein of bovine rotavirus (Redmond et al., Mol. Immunol. 28:269 (1991)) into immune stimulating molecules (ISCOMS) composed of saponins such as Quil A (Morein et al., Nature 308:457 (1984)); Morein et al., in Immunological Adjuvants and Vaccines (G. Gregoriadis al. eds.) pp. 153-162, Plenum Press, NY (1987)) or into controlled-release biodegradable microspheres composed, for example, of lactide-glycolide copolymers (O'Hagan et al., Immunology 73:239 (1991); O'Hagan et al., Vaccine 11:149 (1993)).

Polypeptide antigens can also be adsorbed to the surface of lipid microspheres containing *Moritella* lipid A and optionally squalene or squalane emulsions prepared with a PLURONIC block-copolymer such as L-121 and stabilized with a detergent such as TWEEN 80 (see Allison and Byers, Vaccines: New Approaches to Immunological Problems (R. Ellis ed.) pp. 431-449, Butterworth-Hinemann, Stoneman N.Y. (1992)).

Vaccine formulations described herein comprise an antigen or nucleic acid encoding an antigen and/or *Moritella* lipopolysaccharide or lipid A molecules as described herein in an "effective amount" or a "therapeutically effective amount." As used herein, the phrase "effective amount" or "therapeutically effective amount" refers to a dose sufficient to provide concentrations high enough to generate (or contribute to the generation of) an immune response in the recipient thereof. The specific effective dose level for any particular subject will depend upon a variety of factors including the disorder being treated, the severity of the disorder, the activity of the specific compound, the route of administration, the rate of clearance of the administered agent(s), the duration of treatment, the drugs used in combination or coincident with the administered agent(s), the potency of the lipid A composition, the age, body weight, sex, diet, and general health of the subject, and like factors well known in the medical arts and sciences. Various general considerations taken into account in determining the "therapeutically effective amount" are known to those of skill in the art and are described, e.g., in Gilman et al., eds., Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990.

The pH of the formulation can also vary. In general, it is between about pH 6.2 to about pH 8.0. In some embodiments, the pH is about 6.2, about 6.4, about 6.6, about 6.8, about 7.0, about 7.2, about 7.4, about 7.6, about 7.8, or about 8.0. Of course, the pH may also be within a range of values. Thus, in some embodiments the pH is between about 6.2 and about 8.0, between about 6.2 and 7.8, between about 6.2 and 7.6, between about 6.2 and 7.4, between about 6.2 and 7.2, between about 6.2 and 7.0, between about 6.2 and 6.8, between about 6.2 and about 6.6, or between about 6.2 and 6.4. In other embodiments, the pH is between about 6.4 and about 8.0, between about 6.4 and 7.8, between about 6.4 and 7.6, between about 6.4 and 7.4, between about 6.4 and 7.2, between about 6.4 and 7.0, between about 6.4 and 6.8, or between about 6.4 and about 6.6. In still other embodiments, the pH is between about 6.6 and about 8.0, between about 6.6 and 7.8, between about 6.6 and 7.6, between about 6.6 and 7.4, between about 6.6 and 7.2, between about 6.6 and 7.0, or between about 6.6 and 6.8. In yet other embodiments, it is between about 6.8 and about 8.0, between about 6.8 and 7.8, between about 6.8 and 7.6, between about 6.8 and 7.4, between about 6.8 and 7.2, or between about 6.8 and 7.0. In still other embodiments, it is between about 7.0 and about 8.0, between about 7.0 and 7.8, between about 7.0 and 7.6, between about 7.0 and 7.4, between about 7.0 and 7.2, between about 7.2 and 8.0, between about 7.2 and 7.8, between about 7.2 and about 7.6, between about 7.2 and 7.4, between about 7.4 and about 8.0, about 7.4 and about 7.6, or between about 7.6 and about 8.0.

In some embodiments, the formulation can include one or more salts, such as sodium chloride, sodium phosphate, or a combination thereof. In general, each salt is present in the formulation at about 10 mM to about 200 mM. Thus, in some embodiments, any salt that is present is present at about 10 mM to about 200 mM, about 20 mM to about 200 mM, about 25 mM to about 200 mM, at about 30 mM to about 200 mM, at about 40 mM to about 200 mM, at about 50 mM to about 200 mM, at about 75 mM to about 200 mM, at about 100 mM to about 200 mM, at about 125 mM to about 200 mM, at about 150 mM to about 200 mM, or at about 175 mM to about 200 mM. In other embodiments, any salt that is present is present at about 10 mM to about 175 mM, about 20 mM to about 175 mM, about 25 mM to about 175 mM, at about 30 mM to about 175 mM, at about 40 mM to about 175 mM, at about 50 mM to about 175 mM, at about 75 mM to about 175 mM, at about 100 mM to about 175 mM, at about 125 mM to about 175 mM, or at about 150 mM to about 175 mM. In still other embodiments, any salt that is present is present at about 10 mM to about 150 mM, about 20 mM to about 150 mM, about 25 mM to about 150 mM, at about 30 mM to about 150 mM, at about 40 mM to about 150 mM, at about 50 mM to about 150 mM, at about 75 mM to about 150 mM, at about 100 mM to about 150 mM, or at about 125 mM to about 150 mM. In yet other embodiments, any salt that is present is present at about 10 mM to about 125 mM, about 20 mM to about 125 mM, about 25 mM to about 125 mM, at about 30 mM to about 125 mM, at about 40 mM to about 125 mM, at about 50 mM to about 125 mM, at about 75 mM to about 125 mM, or at about 100 mM to about 125 mM. In some embodiments, any salt that is present is present at about 10 mM to about 100 mM, about 20 mM to about 100 mM, about 25 mM to about 100 mM, at about 30 mM to about 100 mM, at about 40 mM to about 100 mM, at about 50 mM to about 100 mM, or at about 75 mM to about 100 mM. In yet other embodiments, any salt that is present is present at about 10 mM to about 75 mM, about 20 mM to about 75 mM, about 25 mM to about 75 mM, at about 30 mM to about 75 mM, at about 40 mM to about 75 mM, or at about 50 mM to about 75 mM. In still other embodiments, any salt that is present is present at about 10 mM to about 50 mM, about 20 mM to about 50 mM, about 25 mM to about 50 mM, at about 30 mM to about 50 mM, or at about 40 mM to about 50 mM. In other embodiments, any salt that is present is present at about 10 mM to about 40 mM, about 20 mM to about 40 mM, about 25 mM to about 40 mM, at about 30 mM to about 40 mM, at about 10 mM to about 30 mM, at about 20 mM to about 30, at about 25 mM to about 30 mM, at about 10 mM to about 25 mM, at about 20 mM to about 25 mM, or at about 10 mM to about 20 mM. In one embodiment, the sodium chloride is present in the formulation at about 100 mM. In one embodiment, the sodium phosphate is present in the formulation at about 25 mM.

Vaccine formulations described herein can further comprise a solubilizing agent such as a nonionic detergent. Such detergents include, but are not limited to, polysorbate 80 (Tween® 80), TritonX100 and polysorbate 20.

Vaccine Administration and Efficacy

Vaccine formulations as described herein can further comprise a pharmaceutically acceptable carrier, including any suitable diluent or excipient, which includes any pharmaceutical agent that does not itself induce the production of an immune response harmful to the vertebrate receiving the composition, and which may be administered without undue toxicity. As used herein, the term "pharmaceutically acceptable" means being approved by a regulatory agency of the Federal or a state government or listed in the U.S. Pharmacopia, European Pharmacopia or other generally recognized pharmacopia for use in vertebrates, and more particularly in humans. These compositions can be useful as a vaccine and/or antigenic compositions for inducing a protective immune response in a vertebrate.

Pharmaceutically acceptable carriers or excipients include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration. In a preferred embodiment, the formulation is suitable for administration to humans, preferably is sterile, non-particulate and/or non-pyrogenic.

The composition, if desired, can also contain minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Generally, the vaccines described herein are administered in combination with an effective amount or quantity of lipid A as described herein that is sufficient to stimulate an immune response against a given antigen (e.g., viral or bacterial etc). Typically, the dose can be adjusted based on, e.g., age, physical condition, body weight, sex, diet, time of administration, and other clinical factors.

While stimulation of substantial immunity with a single dose is preferred, additional dosages can be administered, by the same or different route, to achieve the desired effect. In neonates and infants, for example, multiple administrations may be required to elicit sufficient levels of immunity. Administration can continue at intervals throughout childhood, as necessary to maintain sufficient levels of protection against a viral or bacterial infection. Similarly, adults who are particularly susceptible to serious disease or repeat infections, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

A prophylactic vaccine formulation can be systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract. While any of the above routes of delivery can result in an immune response, intranasal administration may confer the added benefit of eliciting mucosal immunity at one of the sites of entry of respiratory viruses (e.g., beta coronaviruses, influenza).

Non-limiting methods of administering a vaccine formulation as described herein include, but are not limited to, parenteral administration (e.g., intradermal, intramuscular, intravenous and subcutaneous), epidural, and mucosal (e.g., intranasal and oral or pulmonary routes or by suppositories). In a specific embodiment, vaccine compositions as described herein are administered intramuscularly, intravenously, subcutaneously, transdermally or intradermally. The compositions may be administered by any convenient route, for example by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and may be administered together with other biologically active agents. In some embodiments, intranasal or other mucosal routes of administration of a vaccine composition as described herein may induce an antibody or other immune response that is substantially higher than other routes of administration. Administration can be systemic or local. In some embodiments, the vaccine formulation is administered in such a manner as to target mucosal tissues in order to elicit an immune response at the site of immunization. For example, mucosal tissues such as gut associated lymphoid tissue (GALT) can be targeted for immunization by using oral administration of compositions which contain adjuvants with particular mucosal targeting properties. Additional mucosal tissues can also be targeted, such as nasopharyngeal lymphoid tissue (NALT) and bronchial-associated lymphoid tissue (BALT).

Vaccine formulations as described herein can also be administered on a dosage schedule, for example, an initial administration of the vaccine composition with subsequent booster administrations. In particular embodiments, a second dose of the composition is administered anywhere from two weeks to one year, preferably from about 1, about 2, about 3, about 4, about 5 to about 6 months, after the initial administration. Additionally, a third dose may be administered after the second dose and from about three months to about two years, or even longer, preferably about 4, about 5, or about 6 months, or about 7 months to about one year after the initial administration. The third dose may be optionally administered when no or low levels of specific immunoglobulins are detected in the serum and/or urine or mucosal secretions of the subject after the second dose. In some embodiment, a second dose is administered about two weeks to one month after the first administration and a third dose is administered about six months after the second administration.

The dosage of the pharmaceutical formulation can be determined readily by the skilled artisan, for example, by first identifying doses effective to elicit a prophylactic or therapeutic immune response, e.g., by measuring the serum titer of virus specific immunoglobulins or by measuring the inhibitory ratio of antibodies in serum samples, or urine samples, or mucosal secretions. Said dosages can be determined from animal studies. A non-limiting list of animals used to study respiratory viruses include the guinea pig, Syrian hamster, chinchilla, hedgehog, chicken, rat, mouse, pig, bovine, bat and ferret. Any of the above animals can be dosed with a vaccine formulation as described herein, to partially characterize the immune response induced, and/or to determine if any neutralizing antibodies have been produced.

In addition, human clinical studies can be performed to determine the preferred effective dose for humans by a skilled artisan. Such clinical studies are routine and well known in the art. The precise dose to be employed will also depend on the route of administration. Effective doses can be extrapolated from dose-response curves derived from in vitro or animal test systems.

While the lipid A molecules described herein can be used to raise a sufficient immune response to a given vaccine antigen, it is specifically contemplated that the vaccine or adjuvant composition can also comprise one or more immune stimulators, such as one or more cytokines, lymphokines or chemokines with immunostimulatory, immunopotentiating, and/or pro-inflammatory activities (e.g., interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc.) to further refine the immune response to a desired degree or level. Such immunostimulatory molecules can be administered in the same formulation as the vaccine formulation, or can be administered separately.

Drug Delivery Particles

Lipopolysaccharides from *Moritella* are amphiphilic and comprise both a hydrophobic region and a water soluble region, thus making them useful for the production of micelles, liposomes or other drug delivery particles (e.g., self-assembling structures). In addition, lipid A molecules derived or engineered from *Moritella* lipopolysaccharide are hydrophobic and can be used as components of micelles, liposomes, or polymeric compositions to deliver bioactive agents to a desired site. Such drug delivery particles can comprise a targeting moiety to target them to a particular tissue, organ or disease site (e.g., a tumor).

Micelles and Liposomes: Amphiphilic polymers form a micelle structure in an aqueous solution since the water solubility of their hydrophilic moiety greatly differs from that of their hydrophobic moiety. In the aqueous solution, the micelle has a unique core-shell structure wherein the hydrophobic moieties form an inner core and the hydrophilic moieties form an outer shell. The inner cores of such micelles can be filled with water-insoluble drugs, thereafter which would show a greatly-enhanced water solubility and an extended duration of a therapeutic effect. Furthermore, it is possible to control drug distribution in a body depending on the size of the micelle and to deliver a drug onto a target depending on the surface properties thereof.

The term "liposomes" refers to a synthetic entity or vesicle, formed of at least one lipid bilayer membrane (or matrix) enclosing an aqueous compartment. Liposomes can be unilamellar (a single bilayer membrane) or multilamellar (several membranes layered like an onion). The lipids constituting the bilayer membrane comprise a nonpolar region which, typically, is made of chain(s) of fatty acids or of cholesterol and a polar region (e.g., lipid A molecules described herein and the like), typically made of a phosphate group and/or of tertiary or quaternary ammonium salts. Depending on its composition, the polar region may, in particular at physiological pH (pH≈7) carry either a negative (anionic lipid) or positive (cationic lipid) net (overall) surface charge, or not carry a net charge (neutral lipid).

The liposomes comprising lipid A as a component can any type of liposome; in particular, they may be constituted of any lipid known to be of use in the production of liposomes. The lipid(s) that go(es) to make up the composition of the liposomes can be neutral, anionic or cationic lipid(s); the latter being preferred. These lipids can be of natural origin (plant or egg extraction products, for example) or synthetic origin. The liposomes can also be constituted of a mixture of these lipids; for example, of a cationic or anionic lipid or a neutral lipid and/or lipid A molecules as described herein, as a mixture. Micelles and liposomes can comprise any amount of lipid A or *Moritella* LPS as desired to generate a drug delivery particle with desired characteristics (e.g., 100%, 95%, 90%, 85%, 80%, 75%, 70%, 65%, 60%, 55%, 50%, 45%, 40%, 35%, 30%, 25%, 20%, 15%, 10%, 5%, 2% or 1% of the drug delivery particle is lipid A or *Moritella* LPS).

When a mixture of lipids is used in a drug delivery particle, the neutral lipid is often referred to as colipid. According to one advantageous embodiment, the charged (cationic or anionic) lipid: neutral lipid molar ratio is between 10:1 and 1:10, advantageously between 4:1 and 1:4, preferably between 3:1 and 1:3, limits included.

Non-limiting examples of neutral lipids include: (i) cholesterol; (ii) phosphatidylcholines such as, for example, 1,2-diacyl-sn-glycero-3-phosphocholines, e.g. 1,2-dioleoyl-sn-glycero-3-phosphocholine (DOPC), and also 1-acyl-2-acyl-sn-glycero-3-phosphocholines of which the acyl chains are different than one another (mixed acyl chains); and (iii) phosphatidylethanolamines such as, for example, 1,2-diacyl-sn-glycero-3-phosphoethanolamines, e.g. 1,2-dioleoyl-sn-glycero-3-phosphoethanolamine (DOPE), and also 1-acyl-2-acyl-sn-glycero-3-phosphoethanolamines bearing mixed acyl chains.

Exemplary anionic lipids include, but are not limited to: (i) cholesteryl hemisuccinate (CHEMS); (ii) phosphatidylserines such as 1,2-diacyl-sn-glycero-3-[phospho-L-serine]s, e.g. 1,2-dioleoyl-sn-glycero-3-[phospho-L-serine] (DOPS), and 1-acyl-2-acyl-sn-glycero-3-[phospho-L-serine]s bearing mixed acyl chains; (iii) phosphatidylglycerols such as 1,2-diacyl-sn-glycero-3-[phospho-rac-(1-glycerol)]s, e.g. 1,2-dioleoyl-sn-glycero-3-[phospho-rac-(1-glycerol)] (DOPG), and 1-acyl-2-acyl-sn-glycero-3-[phospho-rac-(1-glycerol)]s bearing mixed acyl chains; (iv) phosphatidic acids such as 1,2-diacyl-sn-glycero-3-phosphates, e.g. 1,2-dioleoyl-sn-glycero-3-phosphate (DOPA), and 1-acyl-2-acyl-sn-glycero-3-phosphates bearing mixed acyl chains; and (v) phosphatidylinositols such as 1,2-diacyl-sn-glycero-3-(phosphoinositol)s, e.g. 1,2-dioleoyl-sn-glycero-3-(phosphoinositol) (DOPI), and 1-acyl-2-acyl-sn-glycero-3-(phosphoinositol)s bearing mixed acyl chains.

Non-limiting examples of cationic lipids include but are not limited to: (i) lipophilic amines or alkylamines such as, for example, dimethyldioctadecylammonium (DDA), trimethyldioctadecylammonium (DTA) or structural homologs of DDA and of DTA [these alkylamines are advantageously used in the form of a salt; for example, of dimethyldioctadecylammonium bromide (DDAB)]; (ii) octadecenoyloxy (ethyl-2-heptadecenyl-3-hydroxyethyl)imidazolinium (DOTIM) and structural homologs thereof, (iii) lipospermines such as N-palmitoyl-D-erythrosphingosyl-1-O-carbamoylspermine (CCS) and dioctadecylamidoglycylspermine (DOGS, transfectam); (iv) lipids incorporating an ethylphosphocholine structure, such as cationic derivatives of phospholipids, in particular phosphoric ester derivatives of phosphatidylcholine, for example those described in patent application WO 05/049080 and including, in particular:

1,2-dimyristoyl-sn-glycero-3-ethylphosphocholine,
1,2-dipalmitoyl-sn-glycero-3-ethylphosphocholine,
1,2-palmitoyloleoyl-sn-glycero-3-ethylphosphocholine,
1,2-distearoyl-sn-glycero-3-ethylphosphocholine (DSPC),
1,2-dioleyl-sn-glycero-3-ethylphosphocholine (DOEPC or EDOPC or ethyl-DOPC or ethyl PC),
and also structural homologs thereof;

(v) lipids incorporating a trimethylammonium structure, such as N-(1-[2,3-dioleyloxy]propyl)-N,N,N-trimethylammonium (DOTMA) and structural homologs thereof and those incorporating a trimethylammonium propane structure, such as 1,2-dioleyl-3-trimethylammonium propane (DOTAP) and structural homologs thereof, and also lipids incorporating a dimethylammonium structure, such as 1,2-dioleyl-3-dimethylammonium propane (DODAP) and structural homologs thereof, and (vi) cationic derivatives of cholesterol, such as 3β-[N—(N',N'-dimethylaminoethane)-carbamoyl]cholesterol (DC-Chol) or other cationic derivatives of cholesterol, such as those described in U.S. Pat. No. 5,283,185, and in particular cholesteryl-3β-carboxamidoethylenetrimethylammonium iodide, cholesteryl-3β-carboxyamidoethylene-amine, cholesteryl-3β-oxysuccinamidoethylenetrimethylammonium iodide and 3β-[N-(polyethyleneimine)carbamoyl]cholesterol.

The term "structural homologs" signifies lipids which have the characteristic structure of the reference lipid while at the same time differing therefrom by virtue of secondary modifications, especially in the nonpolar region, in particular of the number of carbon atoms and of double bonds in the fatty acid chains. These fatty acids, which are also found in the neutral and anionic phospholipids, are, for example, dodecanoic or lauric acid (C12:0), tetradecanoic or myristic acid (C14:0), hexadecanoic or palmitic acid (C16:0), cis-9-hexadecanoic or palmitoleic acid (C16:1), octadecanoic or stearic acid (C18:0), cis-9-octadecanoic or oleic acid (C18:1), cis,cis-9,12-octadecadienoic or linoleic acid (C18:2), cis-cis-6,9-octadecadienoic acid (C18:2), all-cis-9,12,15-octadecatrienoic or α-linolenic acid (C18:3), all-cis-6,9,12-octadecatrienoic or γ-linolenic acid (C18:3), eicosanoic or arachidic acid (C20:0), cis-9-eicosenoic or gadoleic acid (C20:1), all-cis-8,11,14-eicosatrienoic acid (C20:3), all-cis-5,8,11,14-eicosatetraenoic or arachidonic acid (C20:4), all-cis-5,8,11,14,17-eicosapentaneoic acid (C20:5), docosanoic or behenic acid (C22:0), all-cis-7,10,13,16,19-docosapentaenoic acid (C22:5), all-cis-4,7,10,13,16,19-docosahexaenoic acid (C22:6) and tetracosanoic or lignoceric acid (C24:0).

Microparticles and Nanoparticles: In some embodiments, lipid A as described herein is incorporated into a "targeting particle," which are substantially spherical bodies or membranous bodies from 500 nm-999 m in size, such as e.g., liposomes, micelles, exosomes, microbubbles, or unilamellar vesicles. In some embodiments, the particle is less than 900 m, less than 800 m, less than 700 m, less than 600 m, less than 500 m, less than 400 m, less than 300 m, less than 200 m, less than 100 m, less than 90 m, less than 80 m, less than 75 m, less than 70 m, less than 60 m, less than 50 m, less than 40 m, less than 30 m, less than 25 m, less than 20 m, less than 15 m, less than 10 m, less than 5 m, less than 2 m, less than 1 m, less than 750 nm, less than 500 nm or smaller. As will be readily understood by those of skill in the art, a targeting particle that is of nanometer size (e.g., 10 to 1000 nm) is also referred to herein as a "nanoparticle."

Nanoparticles can be solid, colloidal particles consisting of macromolecular substances that vary in size from 10-1000 nanometers. A therapeutic agent can be dissolved, entrapped, adsorbed, attached or encapsulated into the nanoparticle matrix for delivery (including targeted delivery) for therapeutic treatment of a given disease. The nanoparticle matrix can be comprised of biodegradable materials such as polymers or proteins and lipid A as described herein. Depending on the method of preparation, nanoparticles can be obtained with different properties and release characteristics for the encapsulated therapeutic agents (Sahoo S K and Labhasetwar V, Nanotech approaches to drug delivery and imaging, DDT 8:1112-1120, 2003).

Nanoparticles, because of their small size, can penetrate through smaller capillaries and are taken up by cells, which allows efficient drug accumulation at the target sites (Panyam J et al., Nanoparticles can be made of biodegradable materials to permit sustained drug release within the target site over a period of days or even weeks. Nanoparticles can also be effective drug delivery mechanisms for drugs whose targets are cytoplasmic.

Targeted delivery of nanoparticles can be achieved by either passive or active targeting. Active targeting of a therapeutic agent is achieved by including a moiety that recognizes and binds to a tissue or cell-specific ligand (Lamprecht et al., Biodegradable nanoparticles for targeted drug delivery in treatment of inflammatory bowel disease, J Pharmacol Exp Ther. 299:775-81, 2002). Passive targeting is achieved by coupling the therapeutic agent to a macromolecule that passively reaches the target organ or cell type (Monsky W L et al., Augmentation of transvascular transport of macromolecules and nanoparticles in tumors using vascular endothelial growth factor, Cancer Res. 59:4129-35, 1999).

Nanoparticles prepared using biodegradable materials are preferable, however any suitable material can be used in the preparation of drug-delivery nanoparticles including, but not limited to, polymers, lipids (e.g., hydrogenated soy phosphatidylcholine (HSPC), egg phosphatidylcholine (EPC), phosphatidyl ethanolamine (PE), phosphatidyl glycerol (PG), phosphatidyl inositol (PI), monosialogangolioside, sphingomyelin (SPM), distearoylphosphatidylcholine (DSPC), dimyristoylphosphatidylcholine (DMPC), or dimyristoylphosphatidylglycerol (DMPG)), metals (e.g., gold, silver, or a magnetic nanoparticle), etc. Representative, non-limiting examples of biodegradable polymers include synthetic polymers such as polymers of lactic acid and glycolic acid, polyanhydrides, poly(ortho)esters, polyurethanes, poly(hydroxybutiric acid), poly(valeric acid), and poly (lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin, and other hydrophilic proteins. The compositions described herein can also comprise bioerodible hydrogels which are prepared from materials and combinations of materials such as polyhyaluronic acids, casein, gelatin, gluten, polyanhydrides, polyacrylic acid, alginate, chitosan, poly(methyl methacrylates), poly(ethyl methacrylates), poly(butylmethacrylate), poly (isobutyl methacrylate), poly (hexylmethacrylate), poly (isodecyl methacrylate), poly (lauryl methacrylate), poly (phenyl methacrylate), poly(methyl acrylate), poly(isopropyl acrylate), poly(isobutyl acrylate), and poly (octadecyl acrylate). Preferred biodegradable polymers are polyglycolic acid, polylactic acid, copolymers of glycolic acid and L- or D,L-lactic acid, and copolymers of glycolide and L- or D,L-lactide.

In some embodiments, the drug delivery particle comprising immune-silent lipid A further comprises a polymer or a polymeric shell. The polymer can be natural or synthetic, with synthetic polymers being preferred due to the better characterization of degradation and, where appropriate, release profile of an incorporated agent. The polymer can be selected based on the period over which degradation or release of an agent is desired, generally in the range of at several weeks to several months, although shorter or longer periods may be desirable.

The compositions described herein can also include a conjugate of a lipid and a hydrophilic polymer, referred to as a 'lipopolymer.' Lipopolymers can be obtained commercially or can be synthesized using known procedures. For example, lipopolymers comprised of methoxy(polyethylene glycol) (mPEG) and a phosphatidylethanolamine (e.g., dimyristoyl phosphatidylethanolamine, dipalmitoyl phosphatidylethanolamine, 1,2-distearoyl-3-sn-glycerophosphoethanolamine (distearoyl phosphatidylethanolamine (DSPE)), or dioleoyl phosphatidylethanolamine) can be obtained from Avanti Polar Lipids, Inc. (Alabaster, Ala.) at various mPEG molecular weights (350, 550, 750, 1000, 2000, 3000, 5000 Daltons). Lipopolymers of mPEG-ceramide can also be purchased from Avanti Polar Lipids, Inc. Preparation of lipid-polymer conjugates are known in the art and are not described in detail herein.

The hydrophobic component of the lipopolymer can be lipid A as described herein or any other hydrophobic compound can have or are modified to have a chemical group suitable for covalent attachment of a hydrophilic polymer chain. Exemplary chemical groups are, for example, an amine group, a hydroxyl group, an aldehyde group, and a carboxylic acid group. Preferred hydrophobic components are lipids, such as cholesterol, cholesterol derivatives, sphingomyelin, and phospholipids, such as phosphatidylcholine (PC), phosphatidylethanolamine (PE), phosphatidylglycerol (PG), phosphatidic acid (PA), phosphatidylinositol (PI), where the two hydrocarbon chains are typically between about 8-24 carbon atoms in length, and have varying degrees of unsaturation. These lipids are exemplary and are not intended to be limiting, as those of skill can readily identify other lipids that can be covalently modified with a hydrophilic polymer and incorporated into the particles described herein. In some embodiments, the lipopolymer is formed of polyethylene-glycol and a lipid, such as distearoyl phosphatidylethanolamine (DSPE), PEG-DSPE. PEG-DSPE has some degree of biodegradability in vivo, by virtue of the hydrolysable bonds between the fatty acids and the glycerol moiety.

Lipid nanoparticle formulations are specifically contemplated for delivering components of a CRISPR/Cas system.

Bioactive Agents

In some embodiments, the *Moritella* lipopolysaccharide or lipid A molecules described herein can be used as part of a drug delivery composition to facilitate delivery of a biologically active agent or therapeutic agent. A variety of different pharmaceutical/therapeutic agents can be used in conjunction with the methods and compositions described herein and include, but are not limited to, small molecules, proteins, antibodies, peptides and nucleic acids. In one embodiment, the bioactive agent comprises a nucleic acid, such as DNA, RNA, mRNA, siRNA, miRNA, oligonucleotide, shRNA, etc. Other exemplary agents include, but are not limited to, enzyme inhibitors, hormones, RNA interference molecules, cytokines, growth factors, receptor ligands, antibodies, antigens, ion binding compounds, chelators, substantially complementary nucleic acids, nucleic acid binding proteins including transcription factors, toxins, etc. In one embodiment, the nucleic acid encodes a bioactive agent. In such embodiments, the nucleic acid is operably linked to a promoter.

In general, bioactive agents which can be administered with a composition comprising a *Moritella* lipopolysaccharide or lipid A molecule as described herein include, without limitation: anti-infectives such as antibiotics and antiviral agents; chemotherapeutic agents (i.e. anticancer agents); anti-rejection agents; analgesics and analgesic combinations; anti-inflammatory agents; hormones (e.g., steroids); growth factors, and other naturally derived or genetically engineered proteins, polysaccharides, glycoproteins, or lipoproteins. Additionally, the particles described herein can be used to deliver any type of molecular compound, such as for example, pharmacological agents, vitamins, sedatives, steroids, hypnotics, antibiotics, chemotherapeutic agents, prostaglandins, and radiopharmaceuticals. The compositions described herein are suitable for delivery of the above materials and others including, but not limited to, proteins, peptides, nucleotides, carbohydrates, simple sugars, anti-thrombotics, anti-metabolics, growth factor inhibitors, growth promoters, anticoagulants, antimitotics, fibrinolytics, anti-inflammatory steroids, drugs, and monoclonal antibodies, among others.

In some embodiments the agent can be a growth factor, a hormone, or a cytokine such as leptin, sortilin, transglutaminase, prostaglandin E, 1,25-dihydroxyvitamin D3, ascorbic acid, TAK-778, statins, interleukins such as IL-3 and IL-6, growth hormone, human growth hormone, steel factor (SF), activin A (ACT), retinoic acid (RA), bone morphogenetic proteins (BMP), hepatocyte growth factor, hematopoietic growth factors, peptide growth factors, erythropoietin, interleukins, tumor necrosis factors, interferons, colony stimulating factors, heparin binding growth factor (HBGF), alpha or beta transforming growth factor ($\alpha$ or $\beta$-TGF), fibroblast growth factors, vascular endothelium growth factor (VEGF), nerve growth factor (NGF), thrombopoietin (TPO), insulin, transferrin, ciliary neurotrophic factor, prolactin, adrenocorticotropic hormone (ACTH), calcitonin, human chorionic gonadotropin, cortisol, estradiol, follicle stimulating hormone (FSH), thyroid-stimulating hormone (TSH), leutinizing hormone (LH), progesterone, testosterone, toxins including ricin, and any drugs as outlined in the Physician's Desk Reference, Medical Economics Data Production Company, Montvale, N J, 1998 and the Merck Index, 11th Edition (especially pages Ther-1 to Ther-29), both of which are expressly incorporated by reference.

In other embodiments, the agent is an anti-thrombotic agent including, but not limited to, heparin, inhibitors of factor Xa, thrombin inhibitors, thrombolytics, cyclooxygenase inhibitors, ADP receptor inhibitors, phosphodiesterase inhibitors, glycoprotein IIb/IIIa inhibitors, nitric oxide producing drugs and adenosine reuptake inhibitors.

The therapeutically active compound can also be a drug used to treat cancer. In one embodiment, the bioactive agent is a chemotherapeutic agent. Chemotherapeutic agents are typically cytotoxic antineoplastic drugs that find use as part of a standardized regimen of cancer treatment. Chemotherapy can be given with a curative intent or it may aim to prolong life or to palliate symptoms. It is often used in conjunction with other cancer treatments, such as radiation therapy or surgery. Certain chemotherapeutic agents also have a role in the treatment of other conditions, including ankylosing spondylitis, multiple sclerosis, Crohn's disease, psoriasis, psoriatic arthritis, rheumatoid arthritis, and scleroderma. Non-limiting examples of suitable cancer drugs include, but are not limited to, antineoplastic drugs, including alkylating agents such as alkyl sulfonates (e.g., busulfan, improsulfan, piposulfan); aziridines (e.g., benzodepa, carboquone, meturedepa, uredepa); ethylenimines and methylmelamines (e.g., altretamine, triethylenemelamine, triethylenephosphoramide, triethylenethiophosphoramide, trimethylolmelamine); nitrogen mustards (e.g., chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard); nitrosoureas (e.g., carmustine, chlorozotocin, fotenmustine, lomustine, nimustine, ranimustine); dacarbazine, mannomustine, mitobranitol, mitolactol; pipobroman; doxorubicin, carboplatin, oxaliplatin, and cisplatin, (including derivatives).

In some embodiments, the therapeutically active compound is an antiviral or antibacterial drug, including, but not limited to, aclacinomycins, actinomycin, anthramycin, azaserine, bleomycins, cuctinomycin, carubicin, carzinophilin, chromomycins, ductinomycin, daunorubicin, 6-diazo-5-oxn-l-norieucine, duxorubicin, epirubicin, mitomycins, mycophenolic acid, nogalumycin, olivomycins, peplomycin, plicamycin, porfiromycin, puromycin, streptonigrin, streptozocin, tubercidin, ubenimex, zinostatin, zorubicin; aminoglycosides and polyene and macrolide antibiotics.

In other embodiments, the therapeutically active compound is a radio-sensitizer drug, which sensitizes cells to radiation. In one embodiment, the cells sensitized are tumor cells. These drugs may be used in conjunction with radiation therapy for cancer treatment. Radiosensitizer drugs include without limitation halogenated pyrimidines such as bromodeoxyuridine and 5-lododeoxyuridine (IUdR), caffeine, and hypoxic cell sensitizers such as isometronidazole.

In another embodiment, the therapeutic agent in a radioprotectant or radioprotector, which protects normal cells, such as non-tumor cells from any damage caused by radiation therapy of tumor cells. Examples of radioprotectants include without limitation amifostine (Ethyol®).

In some embodiments, the therapeutically active compound is an anti-inflammatory drug (either steroidal or non-steroidal).

In one embodiment, the therapeutically active compound is involved in angiogenesis. Suitable moieties include, but are not limited to, endostatin, angiostatin, interferons, platelet factor 4 (PF4), thrombospondin, transforming growth factor beta, tissue inhibitors of metalloproteinase-1, -2 and -3 (TIMP-1, -2 and -3), TNP-470, Marimastat, Neovastat, BMS-275291, COL-3, AG3340, Thalidomide, Squalamine, Combrestastatin, SU5416, SU6668, IFN-σ, EMD121974, CAI, IL-12 and IM862.

In addition, the material may be any number of organic species, including but not limited to organic molecules and salts thereof, as well as biomolecules, including, but not limited to, proteins, nucleic acids, lipids, carbohydrates, and small molecule materials, such as drugs, specifically including hormones, cytokines, antibodies, cellular membrane antigens and receptors (neural, hormonal, nutrient, and cell surface receptors) or their ligands, etc).

RNA interference agents, such as miRNA, shRNA, siRNA, double stranded DNA etc., can be delivered using a drug delivery particle comprising lipid A as described herein, to inhibit the expression and/or activity of a target polypeptide. As used herein, "inhibition of target gene expression" includes any decrease in expression or protein activity or level of the target gene or protein encoded by the target gene as compared to a situation wherein no RNA interference has been induced. The decrease can be of at least 20%, 30%, 40%, 50%, 60%, 70%, 80%, 90%, 95% or 99% or more as compared to the expression of a target gene or the activity or level of the protein encoded by a target gene which has not been targeted by an RNA interfering agent. RNA interfering agents contemplated for use with the methods described herein include, but are not limited to, siRNA, shRNA, miRNA, and dsRNAi.

The target gene or sequence of the RNA interfering agent can be a cellular gene or genomic sequence. An siRNA can be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. Preferably, the siRNA is identical in sequence to its target and targets only one sequence. Each of the RNA interfering agents, such as siRNAs, can be screened for potential off-target effects by, for example, expression profiling. Such methods are known to one skilled in the art and are described, for example, in Jackson et al., Nature Biotechnology 6:635-637 (2003), herein incorporated by reference in its entirety.

It is well within the ability of one skilled in the art to design and test for siRNAs that are useful for inhibiting expression and/or activity of a target polypeptide. Commercially available RNA interference molecules can be obtained from e.g., Santa Cruz Biotechnology Inc. (Santa Cruz, CA), Cell Signaling Technologies (Danvers, MA), Sigma-Aldrich (St. Louis, MO), and Dharmacon Inc. (Lafayette, CO), among others.

In another embodiment, nucleic acid agents can be delivered using a drug delivery agent comprising a lipid A molecule as described herein. The nucleic acids can be single stranded, double stranded, or a combination thereof. The nucleic acid may be DNA (both genomic and cDNA), RNA or a hybrid, depending on its ultimate use, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

In one embodiment, the drug delivery particle comprising lipid A as described herein can be used to deliver a medical imaging agent. By "medical imaging agent" or "diagnostic agent" or "diagnostic imaging agent" herein is meant an agent that can be introduced into a cell, tissue, organ or patient and provide an image of the cell, tissue, organ or patient. Most imaging methods of imaging make use of a contrast agent of one kind or another. Typically, a contrast agent is injected into the vascular system of the patient, and circulates through the body in approximately half a minute. An image taken of the patient then shows enhanced features relating to the contrast agent. Diagnostic imaging agents include magnetic resonance imaging (MRI) agents, nuclear magnetic resonance (NMR) agents, x-ray imaging agents, optical imaging agents, ultrasound imaging agents and neutron capture therapy agents.

Pharmaceutically Acceptable Carriers

Therapeutic compositions comprising the lipid A molecules as described herein can include a physiologically tolerable carrier together with the lipid A molecule or other agents thereof, dissolved or dispersed therein as an active ingredient. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without toxicity or the production of undesirable physiological effects such as nausea, dizziness, gastric upset and the like. A pharmaceutically acceptable carrier will not itself promote the raising of an immune response to an agent with which it is admixed, unless so desired (e.g., in the setting of vaccines). The preparation of a pharmacological composition that contains active ingredients dissolved or dispersed therein is well understood in the art and need not be limited based on formulation. Typically, such compositions are prepared as topical agents or injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein.

Dosage and Administration

In a vaccine composition or method as described herein, an effective amount of one or more antigens combined with an amount of a lipid A that induces an immune response is administered to a patient for the prevention of a disease or a reduction in symptoms of the disease upon infection. In a drug delivery composition or method as described herein, an effective amount of one or more bioactive agents administered with lipid A are provided to a subject suffering from or diagnosed as having a given disease, or in need of an induced systemic immune response (e.g., having an infection or cancer). In one embodiment, the subject can be a mammal (e.g., a primate or a non-primate mammal). In another embodiment, the mammal can be a human, although the approach is effective with respect to all mammals. An "effective amount" means an amount or dose generally sufficient to bring about the desired therapeutic or prophylactic benefit in subjects undergoing treatment.

Effective amounts or doses of a drug delivery composition for treatment or vaccine as described herein can be ascertained by routine methods such as modeling, dose escalation studies or clinical trials, and by taking into consideration routine factors, e.g., the mode or route of administration of delivery, the pharmacokinetics of the composition, the immune activation potency of the lipid A composition, the severity and course of the disorder or condition, the subject's previous or ongoing therapy, the subject's health status and response to drugs, and the judgment of the treating physician. An exemplary dose for a human is in the range of from about 0.001 to about 8 mg per kg of subject's body weight per day, about 0.05 to 300 mg/day, or about 50 to 400 mg/day, in single or divided dosage units (e.g., BID, TID, QID).

While the dosage range for the vaccine or drug delivery composition to induce the immune response depends upon the potency of the composition, and includes amounts large enough to produce the desired effect (e.g., enhanced immune response), the dosage should not be so large as to cause unacceptable adverse side effects. Generally, the dosage will vary with the formulation (e.g., oral, i.v. or subcutaneous formulations), and with the age, condition, and sex of the patient. The dosage can be determined by one of skill in the art and can also be adjusted by the individual physician in the event of any complication. Typically, the dosage of agents delivered via a drug delivery particle will range from 0.001 mg/day to 400 mg/day. In some embodiments, the dosage range is from 0.001 mg/day to 400 mg/day, from 0.001 mg/day to 300 mg/day, from 0.001 mg/day to 200 mg/day, from 0.001 mg/day to 100 mg/day, from 0.001 mg/day to 50 mg/day, from 0.001 mg/day to 25 mg/day, from 0.001 mg/day to 10 mg/day, from 0.001 mg/day to 5 mg/day, from 0.001 mg/day to 1 mg/day, from 0.001 mg/day to 0.1 mg/day, from 0.001 mg/day to 0.005 mg/day. Alternatively, the dose range will be titrated to maintain serum levels between 0.1 µg/mL and 30 µg/mL.

Administration of the doses recited above can be repeated for a limited period of time or as necessary. In some embodiments, the doses are given once a day, or multiple times a day, for example but not limited to three times a day. In one embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

Agents useful in the methods and compositions described herein depend on the site of disease and can be administered topically, intravenously (by bolus or continuous infusion), intratumorally, orally, by inhalation, intraperitoneally, intramuscularly, subcutaneously, intracavity, and can be delivered by peristaltic means, if desired, or by other means known by those skilled in the art. For the treatment of certain cancers (e.g., metastatic disease), the agent can be administered systemically.

Therapeutic compositions containing at least one agent or vaccine formulations can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

Combination Therapy: When at least two agents (e.g., a vaccine and an adjuvant comprising a lipid A molecule as described herein) are administered "in combination", they can be administered simultaneously in a single composition or in different compositions. In other embodiments, the at least two agents are administered separately or concurrently.

Efficacy Measurement

The efficacy of a vaccine or immunostimulatory lipid A molecule induces an immune response can be determined by the skilled clinician by measuring e.g., antibodies against the antigen, antibody titers, or cytokine production in a subject or measuring parameters in a population of vaccinated individuals such as a reduction in hospitalization rates, decrease in disease severity or duration, reduced transmission, reduced mortality, etc. One of skill in the art can readily assess such parameters using methods known in the art.

The efficacy of a drug delivery particle or device against a given disease can be determined by a reduction in at least one sign or symptom of that disease. Thus, a treatment is considered "effective treatment," as the term is used herein, if any one or all of the signs or symptoms of, as but one example, cancer are altered in a beneficial manner, and/or other clinically accepted symptoms or markers of disease are improved or ameliorated, e.g., by at least 10% following treatment with an inhibitor.

Efficacy can also be measured by failure of an individual to worsen as assessed by hospitalization or need for medical interventions (e.g., progression of the disease is halted or at least slowed). Efficacy in a population of patients can also be determined by measuring mortality rates due to advanced disease. Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of the disease; or (2) relieving the disease, e.g., causing regression of symptoms; and (3) preventing or reducing the likelihood of the development of secondary illness (e.g., metastases, pneumonia etc).

The invention may be as described in any one of the following numbered paragraphs:

1. A composition comprising: an immunostimulatory lipid A molecule engineered from a lipopolysaccharide (LPS) isolated from a bacterium of the genus *Moritella*.
2. The composition of paragraph 1, wherein the immunostimulatory lipid A molecule comprises five, six or seven acyl chains.
3. The composition of paragraph 1 or 2, wherein no more than one of the five, six or seven acyl chains comprises a length of at least 16 carbons (C16).
4. The composition of paragraph 1 or 2, wherein each of the five, six or seven acyl chains each comprise a length of 12-14 carbons (C12-C14).
5. The composition of any one of paragraphs 1-4, wherein the lipid A molecule further comprises a bisphospho-di-glucosamine moiety.
6. The composition of any one of paragraphs 1-5, wherein the lipid A is capable of activating Toll-like receptor signaling, caspase signaling or a combination thereof.
7. The composition of paragraph 6, wherein the lipid A binds to Toll-like Receptor isoform 4 (TLR-4).
8. The composition of any one of paragraphs 1-7, wherein the bacterium of the genus *Moritella* is selected from the group consisting of: *Moritella* 5, *Moritella* 9, *Moritella* 10, *Moritella* 14, *Moritella* 18, *Moritella* 19, *Moritella* 20, *Moritella* 24 and *Moritella* 30.
9. A vaccine adjuvant or vaccine formulation comprising the composition of any one of paragraphs 1-8.
10. The vaccine adjuvant or formulation of paragraph 9, further comprising a nucleic acid or polypeptide.
11. The vaccine adjuvant or formulation of paragraph 10, wherein the nucleic acid comprises DNA, RNA, mRNA, dsDNA, dsRNA, siRNA, miRNA, or shRNA.
12. A method of inducing an immune response against an antigen in a subject, the method comprising: administering to a subject a vaccine comprising an antigen or a nucleic acid encoding an antigen in combination with an immunostimulatory lipid A engineered from a lipopolysaccharide (LPS) isolated from a bacterium of the genus *Moritella*, thereby inducing an immune response in the subject,
    wherein the immune response is increased by at least 10% compared to the vaccine comprising an antigen or nucleic acid encoding an antigen administered in the absence of the immunostimulatory lipid A.
13. The method of paragraph 12, wherein the vaccine comprising the antigen or nucleic acid encoding the antigen and the immunostimulatory lipid A are in the same composition.
14. The method of paragraph 12, wherein the vaccine comprising the antigen or nucleic acid encoding the antigen and the immunostimulatory lipid A are in different compositions.
15. The method of any one of paragraphs 12-14, wherein the immunostimulatory lipid A molecule comprises five, six or seven acyl chains.
16. The method of any one of paragraphs 12-14, wherein no more than one of the five, six or seven acyl chains comprises a length of at least 16 carbons (C16).
17. The method of paragraph 16, wherein each of the five, six or seven acyl chains each comprise a length of 12-14 carbons (C12-C14).
18. The method of any one of paragraphs 12-17, wherein the lipid A molecule further comprises a bisphospho-di-glucosamine moiety.
19. The method of any one of paragraphs 12-18, wherein the lipid A activates Toll-like receptor signaling, caspase signaling or a combination thereof.
20. The method of paragraph 19, wherein the lipid A binds to Toll-like Receptor isoform 4 (TLR-4).
21. The method of any one of paragraphs 12-20, wherein the bacterium of the genus *Moritella* is selected from the group consisting of: *Moritella* 5, *Moritella* 9, *Moritella* 10, *Moritella* 14, *Moritella* 18, *Moritella* 19, *Moritella* 20, *Moritella* 24 and *Moritella* 30.
22. A composition comprising: an immune-silent lipid A molecule engineered from a lipopolysaccharide (LPS) isolated from a bacterium of the genus *Moritella*.
23. The composition of paragraph 22, wherein the lipid A molecule comprises five, six or seven acyl chains.
24. The composition of paragraph 23, wherein at least one of the five, six or seven acyl chains comprises a length of at least 16 carbons (C16).
25. The composition of paragraph 24, wherein at least two of the five, six or seven acyl chains comprises a length of at least 16 carbons (C16).
26. The composition of paragraph 24 or 25, wherein the remaining acyl chains each comprise a length of 12-14 carbons (C12-C14).
27. The composition of paragraph 22, wherein the lipid A molecule engineered from a lipopolysaccharide comprises at least two acyl chains each having a length of at least 16 carbons is more immune-silent than a substantially similar lipid A molecule comprising one acyl chain having a length of at least 16 carbons.
28. The composition of paragraph 27, wherein the immune response is determined by measuring loss of CD14 or TLR-4 receptors from the surface of cells using flow cytometry.
29. The composition of any one of paragraphs 22-28, wherein the immune-silent lipid A does not activate Toll-like receptor signaling or caspase signaling.
30. The composition of any one of paragraphs 22-30, wherein the immune-silent lipid A engineered from a lipopolysaccharide (LPS) further comprises a phosphoethanolamine moiety.
31. The composition of any one of paragraphs 22-30, wherein the bacterium of the genus *Moritella* is selected from the group consisting of: *Moritella* 28 and *Moritella* 36.
32. A drug delivery composition comprising the lipid A of any one of paragraphs 22-31 and an agent, wherein the drug delivery composition does not raise an appreciable immune response when administered to a subject.
33. The drug delivery composition of paragraph 32, wherein the composition comprises a micelle or liposome.
34. The drug delivery composition of paragraph 32 or 33, wherein the agent comprises a nucleic acid, a protein, a drug, a small molecule, or an imaging molecule.
35. The drug delivery composition of paragraph 34, wherein the nucleic acid comprises DNA, RNA, mRNA, dsDNA, dsRNA, siRNA, miRNA, or shRNA.

36. A method for delivering an agent to a subject in need thereof, the method comprising: administering to a subject a drug delivery composition comprising an immune-silent lipid A engineered from a lipopolysaccharide (LPS) isolated from a bacterium of the genus *Moritella* and an agent, thereby delivering the agent to the subject without inducing an appreciable immune response in the subject.

37. A heterogeneous lipid A composition comprising: a plurality of heterogeneous lipid A molecules engineered from a heterogeneous mixture of lipopolysaccharides (LPS) isolated from at least one bacterium of the genus *Moritella*,
   wherein the composition comprises a greater proportion of lipid A molecules having C16 length acyl chains than lipid A molecules lacking C16 acyl chains and is immune-silent, or
   wherein the composition comprises a greater proportion of lipid A molecules lacking C16 length acyl chains than lipid A molecules having C16 acyl chains and is immune-stimulatory.

38. The heterogeneous lipid A composition of paragraph 37, wherein the immune response upon administration to a subject can be modulated based on the proportion of lipid A molecules having C16 length acyl chains as compared to lipid A molecules lacking C16 acyl chains.

39. A composition comprising: a weakly immunostimulatory lipid A molecule engineered from a lipopolysaccharide (LPS) isolated from a bacterium of the genus *Moritella*.

40. The composition of paragraph 39, wherein the weakly immunostimulatory lipid A molecule comprises five, six or seven acyl chains.

41. The composition of paragraph 39 or 40, wherein one of the five, six or seven acyl chains comprises a length of at least 16 carbons (C16).

42. The composition of paragraph 41, wherein the remaining acyl chains each comprise a length of 12-14 carbons (C12-C14).

43. The composition of any one of paragraphs 39-42, wherein the lipid A molecule further comprises a bisphospho-di-glucosamine moiety.

44. The composition of any one of paragraphs 39-43, wherein the lipid A is capable of activating Toll-like receptor signaling, caspase signaling or a combination thereof.

45. The composition of paragraph 44, wherein the lipid A binds to Toll-like Receptor isoform 4 (TLR-4).

46. The composition of any one of paragraphs 39-45, wherein the bacterium of the genus *Moritella* is selected from the group consisting of: *Moritella* 5, *Moritella* 9, *Moritella* 10, *Moritella* 14, *Moritella* 18, *Moritella* 19, *Moritella* 20, *Moritella* 24 and *Moritella* 30.

47. The composition of any one of paragraphs 39-46, wherein the weakly immunostimulatory lipid A induces an immune response when administered to a subject that is at least 20% less than an immune response when the subject is administered lipid A derived from *E. coli*.

48. A vaccine adjuvant or vaccine formulation comprising the composition of any one of paragraphs 39-47.

49. The vaccine adjuvant or formulation of paragraph 48, further comprising a nucleic acid or polypeptide.

50. The vaccine adjuvant or formulation of paragraph 49, wherein the nucleic acid comprises DNA, RNA, mRNA, dsDNA, dsRNA, siRNA, miRNA, or shRNA.

51. A method of inducing an immune response against an antigen in a subject, the method comprising: administering to a subject a vaccine comprising an antigen or a nucleic acid encoding an antigen in combination with a weakly immunostimulatory lipid A engineered from a lipopolysaccharide (LPS) isolated from a bacterium of the genus *Moritella*, thereby inducing an immune response in the subject,
   wherein the immune response is increased by at least 10% compared to the vaccine comprising an antigen or nucleic acid encoding an antigen administered in the absence of the weakly immunostimulatory lipid A.

EXAMPLES

Provided herein are novel compositions of biologically distinct LPS structures that are differentially recognized by mammalian immune systems. These compositions comprise certain LPS structures and additional components that elicit differential and selectively useful responses in mammals. LPS components are conjoined with excipients, for example, lipids, proteins, polymers, and chemical conjugation. Either the *Moritella* LPS alone, or LPS excipients, can display the desired immunostimulatory or immunosilent properties to the mammalian immune system. The methods and compositions described herein allows one to tailor the desired immune responses necessary for the desired application ranging from no innate immune response on one end of the spectrum, to stimulation of the innate immune system on the other. In addition, the immune response can be functionally tailored to stimulate certain immune pathways over others.

The methods and compositions described herein include at least 3 different classes of LPS compositions: immune-silent LPS compositions (*Moritella* 28 and 36), immune-stimulatory LPS compositions (*Moritella* 5, 10 14, 18, 20, 24), and immune-selective stimulatory LPS compositions (e.g., *Moritella* 9), and some LPS compositions with interacting stimulatory properties that are dose-dependent (*Moritella* 19 and 30).

Also provided herein is a class of immuno-silent LPS compositions (*Moritella oceanus* 28 and 36) that can be used to shield a cell, particle, nanoparticle, protein, RNA, DNA or other molecule from being recognized by the body's immune system, thus providing a "stealth" protection. These immuno-silent LPS compositions have utility for cell therapy, including overcoming the immune-rejection barrier for stem cell-derived therapies, engineered tissues, gene therapy, gene modification, drug delivery including oral, intravenous, subcutaneous, and dermal delivery formulations, as well as novel imaging agents with improved safety profiles.

In another embodiment of the methods and compositions described herein, a second class of immune-stimulatory LPS compositions (*Moritella* 5, 10, 14, 18, 20 and 24), and/or their excipients, are used to elicit robust immune stimulation. This stimulation can provide alternatives to monophosphoryl Lipid A (MPL) variants for vaccine adjuvants, for example. These LPS structures could enable safe, consistent, and robust immune stimulation without the use of materials such as *E. coli* LPS structures, which are inherently toxic.

Also provided herein are immune-selective stimulatory LPS compositions (*Moritella* 9) that enable strong or weak immune stimulation of selected pathways. This class of LPS compositions offer the potential to alter the balance of inflammatory activities that are stimulated with LPS or MPL. This balance of inflammatory activities has been long sought after, as LPS-induced inflammatory activities have clinical benefits (stimulating adaptive immunity) and costs (reactogenicity). As LPS from *Moritella* 9 displays a different balance of inflammatory activities than that induced by *E. coli* LPS, *Moritella* 9 LPS may enable adaptive immune responses to be induced without reactogenicity.

Example 1: Immunomodulatory Lipopolysaccharide Compositions

The concept of pattern recognition, initially introduced by Janeway, posits that multicellular eukaryotes should have the ability to detect all microbes in the environment [1]. This assumption of near-universal microbial detection is a foundation of modern immunology, and relies on the ability of multicellular organisms to detect infections through the actions of a set of cellular proteins known as pattern recognition receptors (PRRs) [2]. PRRs recognize potentially infectious agents by detecting specific molecules that are common to large classes of microbes. These molecules, commonly microbial cell wall components or nucleic acids, are known as pathogen associated molecular patterns (PAMPs). Well-characterized examples of PAMPs include the lipid A region of bacterial lipopolysaccharides (LPS), the flagellin subunit of bacterial flagella and double stranded DNA. Each of these molecules is important for the viability or fitness of the organism that produces them. As such, they are highly stable and prevalent in the microbial world [3].

Multiple members of the PRR family have evolved to detect each PAMP [4]. For example, the lipid A region of LPS is detected by several murine PRRs, including CD14, TLR4, MD-2 and caspase-11 [5], whereas double stranded DNA is detected by other receptors, such as cGAS and AIM2 [6]. However, these aggregate characteristics have set up an evolutionary conundrum around PAMPs. For the microbe, PAMPs are essential and maladaptive to alter. Yet these same properties make PAMPs conspicuous, conferring a benefit to the host for evolving PRRs for defense. These benefits to the host likely explain the convergent evolutionary pressures that drove the development of multiple PRRs to recognize the same PAMP.

Based on the above-described scenario, PRRs should have the capacity to detect all members of a given class of microbe. The only exceptions to this statement should be host-adapted microbes that evolved strategies to alter their PAMPs to prevent PRR detection. For example, many commensal bacteria co-exist with mammalian hosts and avoid immune detection, whereas many pathogens avoid detection to exploit the host [7-9]. These exceptions represent the result of co-evolution between host and microbe. For bacteria not closely associated with a host, there are adaptive tradeoffs to altering PAMP structure that keep these strategies the rarity, rather than the norm [10-12]. As such, outside of the intense host-microbial interface, mammalian PRRs are presumed to detect all bacteria they encounter.

However, virtually all knowledge of microbial detection has been derived from studies of bacteria that overlap ecologically with mammals, either in the same habitat or within mammalian hosts [13]. With few exceptions [14-16], these studies focused on bacteria that inhabit terrestrial or shallow-depth aquatic environments [17], where mammals abound [18]. But what of the bacteria that occupy different ecological niches? Can mammalian PRRs detect PAMPs from novel bacteria, or bacteria from habitats with little-to-no mammalian interaction? Is the selective advantage of PAMP detection exclusive to hosts and microbes from sympatric environments? More simply stated, does the pattern recognition concept have limits?

In this study, the inventors sought to test assumptions of the pattern recognition concept by examining the ability of human and murine cells to recognize bacteria that they would have not had the natural opportunity to encounter. These bacteria were collected and cultivated during an expedition to the remote and deep Pacific Ocean, where samples were collected from deep-sea seamounts with abundant and diverse invertebrate life, and that are unoccupied by any resident mammals (Table 1, Table 2).

TABLE 1

Reported ranges of Phoenix Islands Region Marine Mammals. Total marine mammals reported to inhabit the region compared to the marine mammals directly observed in the region; denoted by "x". Maximum depth is the maximum depth that has been published for marine mammal listed. Data from OBIS, [92-94].

| Common name | Scientific | Observed in PIPA? | Max depth (m) |
| --- | --- | --- | --- |
| Bottlenose dolphin | *Tursiops truncatus* | x | 46 |
| Spotted dolphin | *Stenella attenuata* | | 60 |
| Humpback whale | *Megaptera novaeangliae* | x | 240 |
| Killer whale | *Orcinus orca* | | 264 |
| Spinner dolphin | *Stenella longirostris* | x | 300 |
| Bryde's whale | *Balaenoptera edeni* | | 305 |
| Blue whale | *Balaenoptera musculus* | | 315 |
| Striped dolphin | *Stenella coeruleoalba* | | 702 |
| False killer whale | *Pseudorca crassidens* | x | 928 |
| Short Finned Pilot whale | *Globicephala macrorhynchus* | | 1019 |
| Blainville's Beaked Whale | *Mesoplodon densirostris* | x | 1408 |
| Sperm whale | *Physeter macrocephalus* | x | 2250 |
| Cuvier's beaked whale | *Ziphius cavirostris* | | 2992 |

TABLE 2

Diversity of focal taxa at depth for marine mammals (literature-reported), deep-sea corals, and coral-associated invertebrates from the 2017 SOI Falkor and NOAA Okeanos Explorer deep-sea expeditions ([18][1], [60][2]). Depths reported range from 200 m to 2500 m, with the number of reported marine mammals decreasing with depth.

| Depth (m) | mammals whose range includes PIPA[1] | deep-sea corals[2] | deep-sea coral-associated invertebrates |
| --- | --- | --- | --- |
| 200-300 | 11 | 5 | 3 |
| 300-400 | 9 | 11 | 7 |

TABLE 2-continued

Diversity of focal taxa at depth for marine mammals (literature-reported), deep-sea corals, and coral-associated invertebrates from the 2017 SOI Falkor and NOAA Okeanos Explorer deep-sea expeditions ([18][1], [60][2]). Depths reported range from 200 m to 2500 m, with the number of reported marine mammals decreasing with depth.

| Depth (m) | mammals whose range includes PIPA[1] | deep-sea corals[2] | deep-sea coral-associated invertebrates |
|---|---|---|---|
| 400-500 | 6 | 39 | 17 |
| 500-600 | 6 | 68 | 25 |
| 600-700 | 6 | 53 | 20 |
| 700-800 | 6 | 56 | 16 |
| 800-900 | 5 | 76 | 14 |
| 900-1000 | 5 | 62 | 15 |
| 1000-1100 | 4 | 69 | 17 |
| 1100-1200 | 3 | 80 | 14 |
| 1200-1300 | 3 | 63 | 14 |
| 1300-1400 | 3 | 69 | 18 |
| 1400-1500 | 3 | 53 | 13 |
| 1500-1600 | 2 | 33 | 9 |
| 1600-1700 | 2 | 32 | 8 |
| 1700-1800 | 2 | 56 | 11 |
| 1800-1900 | 2 | 68 | 11 |
| 1900-2000 | 2 | 54 | 5 |
| 2000-2100 | 2 | 37 | 10 |
| 2100-2200 | 2 | 31 | 8 |
| 2200-2300 | 2 | 19 | 8 |
| 2300-2400 | 1 | 3 | 2 |
| 2400-2500 | 1 | 1 | 0 |

The inventors spent 20 days onboard the Schmidt Ocean Institute's Research Vessel (R/V) Falkor within the boundaries of Kiribati's Phoenix Islands Protected Area (PIPA), which is a no-take marine protected area and the largest and deepest UNESCO World Heritage site [19]. This expedition included deep-sea mapping and characterization of ecosystem diversity including deep-sea invertebrates and their associated macro- and micro-fauna. Specific to this project, bacteria were collected from the deep sea (>200 m); a distinct ecological niche that is inhospitable to terrestrial life as it is principally devoid of light, under high pressure (20-300 atmospheres), and cold (2-10° C.) [20]. In addition, the deep-sea lacks residential mammalian life [18]. Although some marine mammals access the deep sea through intermittent diving, the primary habitat of marine mammals is the photic zone of the ocean (Table 1; [18]). Bacteria from these remote, deep-sea ecosystems were therefore of high interest, as mammals most likely would not have had the natural opportunity to interact extensively with bacteria from this ecosystem.

Figure 1A:
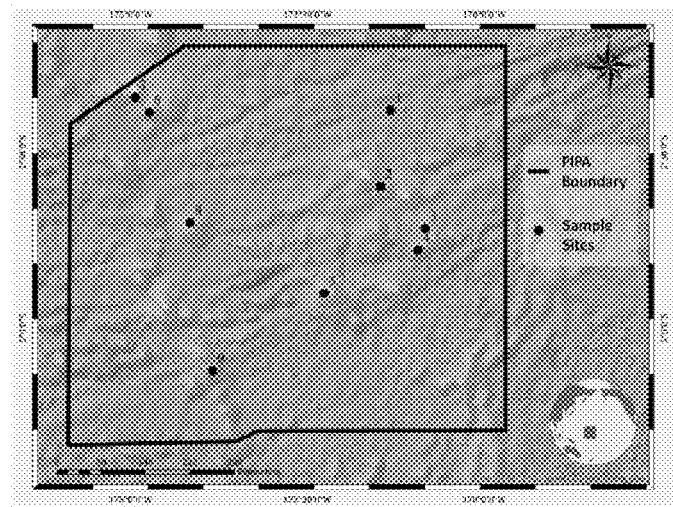
FIGS. 1A-1E. Site map of 9 sites sampled during the R/V Falkor's 2017 expedition to the Phoenix Islands Protected Area, Kiribati (FIG. 1A). Bray-Curtis non-metric multidimensional scaling ordination of total microbial community composition, based on 16S amplicon data from all stations.
Figure 1B:
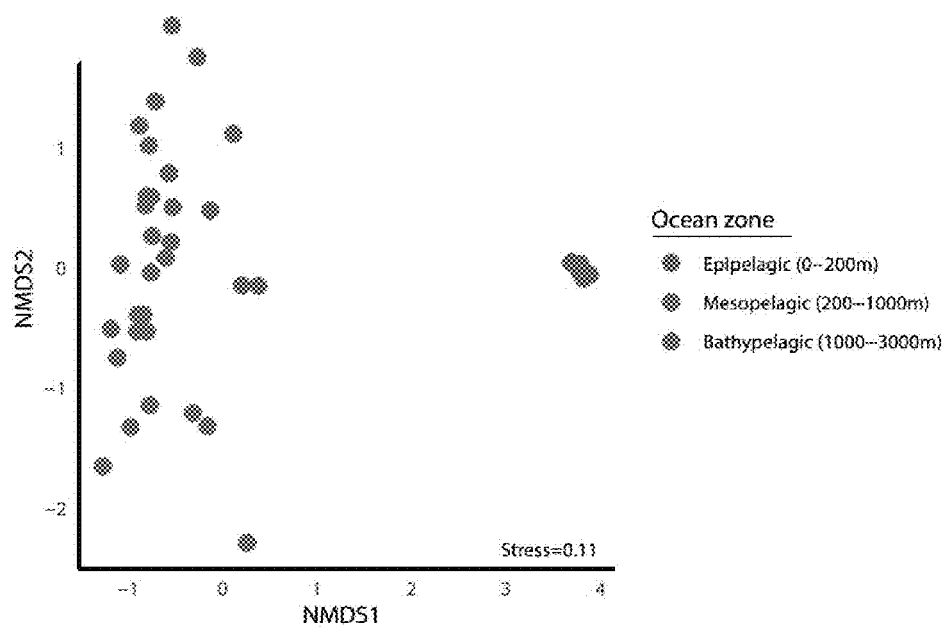
Figure 1C:
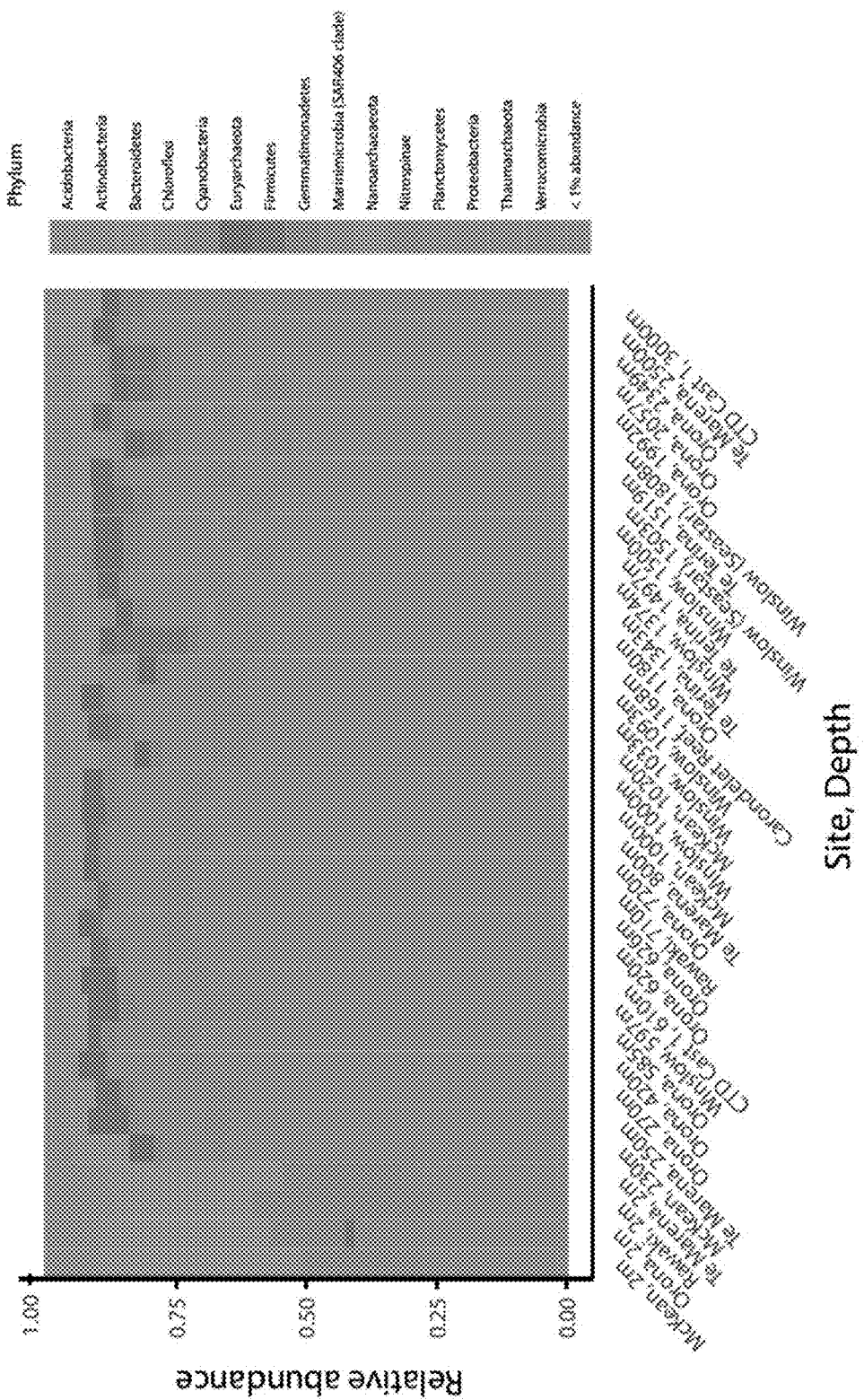

At nine sites within the boundaries of PIPA (FIG. 1A), seawater was collected at stratified depths to assess bacterial community composition by amplicon sequencing of 16S ribosomal RNA (rRNA) genes. There was an observable shift in bacterial community composition between shallow (2 m) and deep (>200 m) seawater samples (FIGS. 1B and 1C). Thus, distinct microbial communities exist in deep-sea regions where mammalian populations are minimal. While the amplicon sequencing data obtained provided the first insights into the bacterial community composition of PIPA, the main goal was to obtain culturable bacteria for experimental analysis.

Figure 1D:
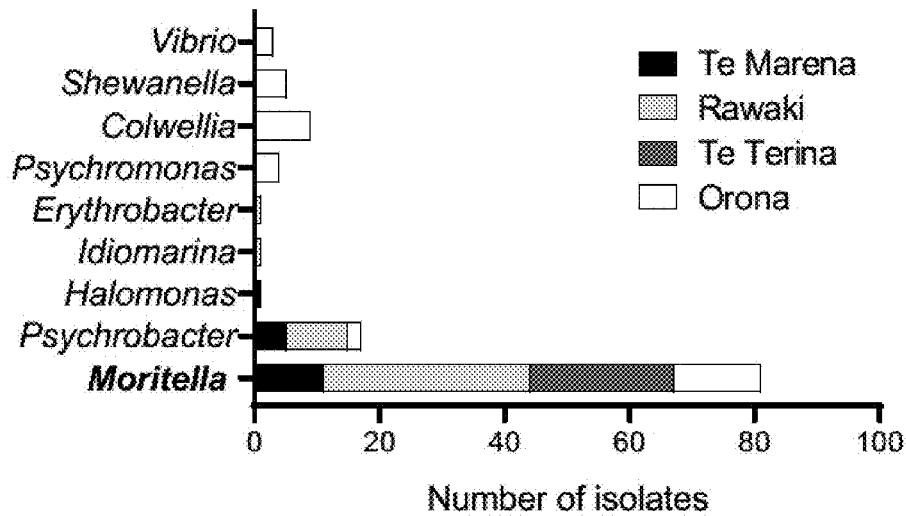
Figure 1E:
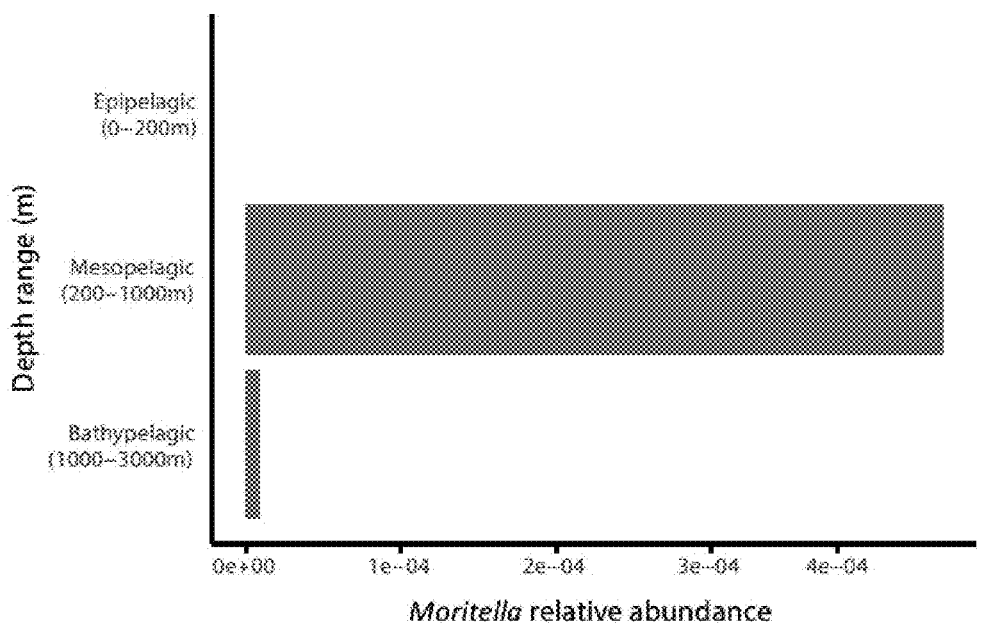

To identify culturable bacteria under laboratory conditions, the inventors sampled four sites (S2-S5) from 200-3000 m depth for seawater, sediment, coral tissue, sponge tissue, and the gut contents of corallivorous sea stars. Immediately after sample collection at sea, bacterial colonies were grown from deep-sea substrates and seawater to build our 'experimental toolbox' of bacterial strains. A total of 117 bacterial colonies were isolated and streak purified from S2-S5. 16S ribosomal sequencing of streak purified strains identified all culturable bacteria to be of the class Gammaproteobacteria, and that 70% (82 of 117) of strains were of the genus *Moritella* (FIG. 1D). Notably, *Moritella* were not detected in surface seawater samples (collected from 2 m) (FIG. 1E). Therefore, the *Moritella* genus is a common culturable constituent among these samples, exclusively found in the deeper waters of PIPA. A subset of these *Moritella* strains served as the foundation for the experimental analyses described herein.

*Moritella* are Gram-negative, which enabled us to determine the ability of mammalian LPS receptors to detect these bacteria. Mouse macrophages display monomers of the LPS receptors CD14 and TLR4 (associated with MD-2) at their plasma membrane, where they survey the extracellular space for this PAMP. When CD14 and TLR4 bind LPS, they are lost from the cell surface. CD14 is immediately internalized into endosomes whereas TLR4 must first dimerize before also being endocytosed [21-23]. The LPS-induced loss of CD14 and TLR4 monomers from the plasma membrane can be monitored by flow cytometry, which represents a rapid assay that enables LPS-PRR interactions to be tracked for endogenous receptors in their natural setting (on the macrophage surface) [21-23].

Using this flow cytometry-based assay, the inventors exposed murine immortalized bone marrow derived macrophages (iBMDMs) to live bacteria for 20 minutes and measured the loss of receptors from the cell surface. *E. coli* LPS possess a hexa-acylated, bis-phosphorylated lipid A anchor that interacts efficiently with both receptors [22]. Accordingly, live *E. coli* was used as a benchmark to delineate whether each *Moritella* strain engaged CD14 and TLR4. The inventors limited the bacterial strains tested to those that were streak purified while onboard the R/V Falkor (n=50). Of the strains examined, 88% were of the genus *Moritella* (n=44), all isolated from >550 m depth.

Figure 2A:
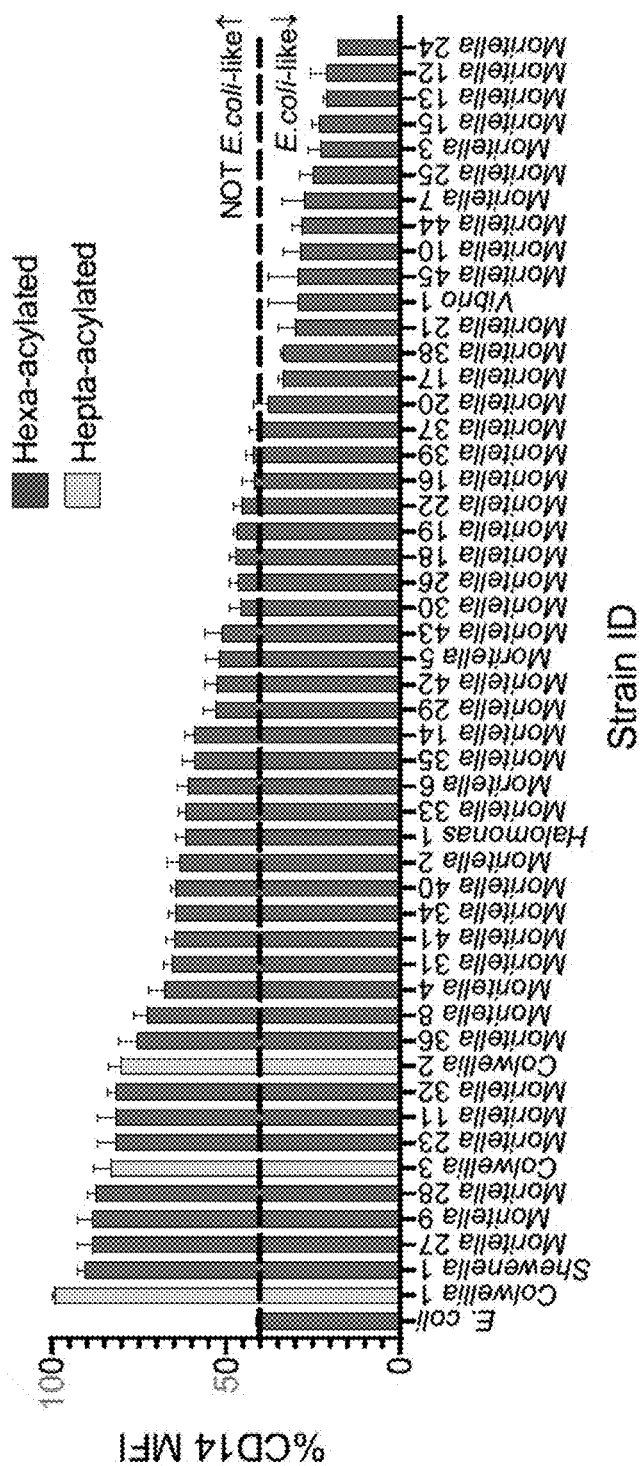
FIGS. 2A-2C. CD14 (FIG. 2A) and TLR4 (FIG. 2B) surface expression as measured by mean fluorescence intensity (MFI) on iBMDMs exposed to live deep-sea bacteria strains compared to live *E. coli* (MOI=50). The color of columns represents the predicted acyl chain number for the LPS lipid A expressed, as described in Table 3. Dashed lines are used to delineate whether bacterial strains are stimulatory or silent to CD14 or TLR4, as compared to *E. coli*. Summary of murine CD14 and TLR4 engagement by strains tested (FIG. 2C).
Figure 2B:
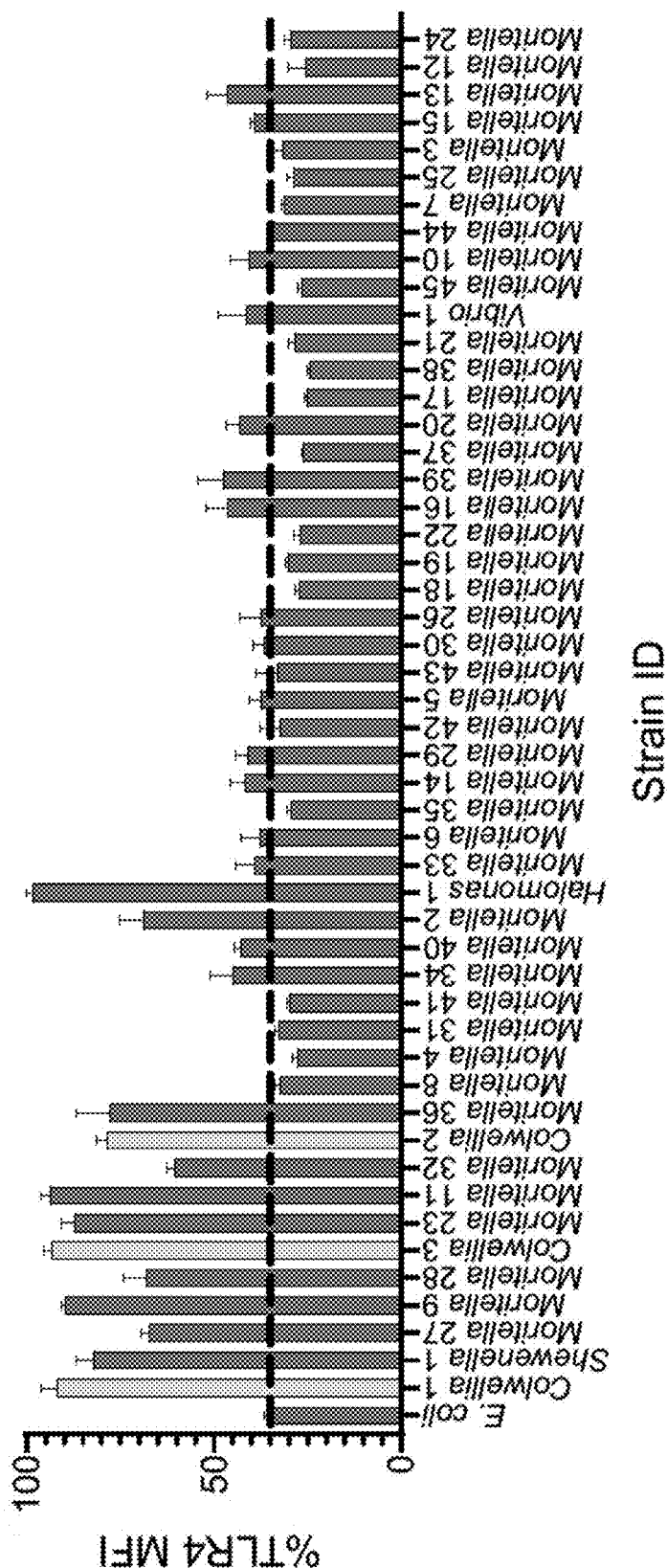
Figures 2C, 3A:
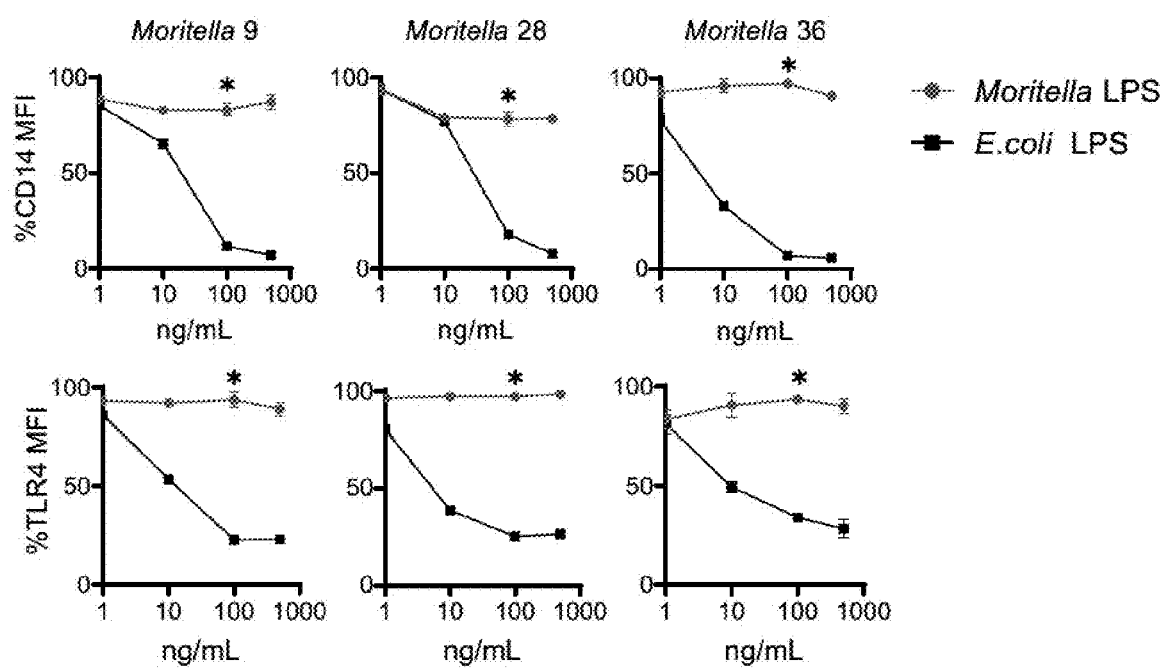
FIGS. 3A-3B. CD14 (FIG. 3A) and TLR4 surface expression as measured by mean fluorescence intensity (MFI) on iBMDMs exposed to live deep-sea bacteria strains compared to live *E. coli* (MOI=50). The color of columns represents the predicted acyl chain number for the LPS lipid A expressed, as described in Table 3. Dashed lines are used to delineate whether bacterial strains are stimulatory or silent to CD14 or TLR4, as compared to *E. coli*. Summary of murine CD14 and TLR4 engagement by strains tested (FIG. 3B).

Compared to *E. coli*, which stimulated CD14 and TLR4 loss from the cell surface, specific marine bacterial strains were grouped into three categories (FIGS. 2A-2C). Category 1 strains behaved similarly to *E. coli*, in that loss of both PRRs occurred. Category 2 strains were unable to engage either PRR. Category 3 strains engaged TLR4 but not CD14. Overall, 9 strains engaged both receptors, 24 engaged neither, 17 engaged TLR4 but not CD14 (FIG. 2C). These findings were notable for two reasons. First, the finding that any strains of bacteria stimulated CD14 and TLR4 provides direct support for a central tenet of the concept of Pattern Recognition—that PRRs have the capacity to detect novel bacteria. It was unexpected that 82% (41/50) of bacteria displayed evidence of immune evasiveness, as defined by an inability to stimulate one or both CD14 and TLR4. Deep-sea microbial species may therefore represent a reservoir of molecules with unpredictable inflammatory activities.

Figure 3B:
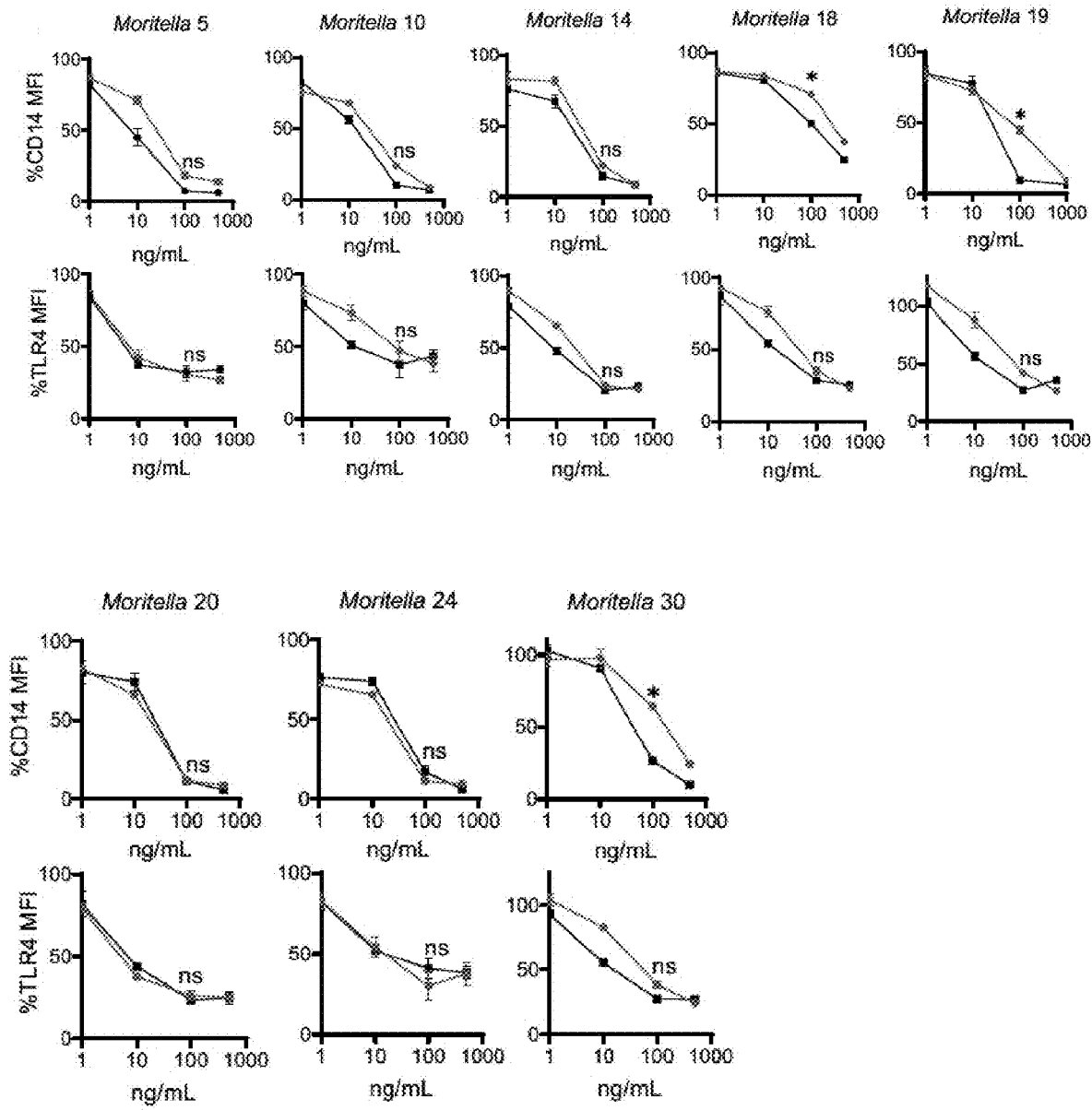

A possible explanation for the inability of deep-sea bacteria to stimulate CD14 or TLR4 is that the cell wall may contain features (e.g. capsular structures) that prevent access of PRRs to immuno-stimulatory LPS. To address this possibility, LPS was isolated from select *Moritella* strains to evaluate if purified LPS behaved similarly to whole bacteria. Twelve *Moritella* strains over the range of CD14-TLR4 engagements were selected for this analysis (FIG. 2). Specifically, three strains were selected that engaged neither PRR, and nine strains were selected that displayed a range of PRR engagement. In all analyses, purified LPS from each *Moritella* strain was compared to *E. coli* LPS (FIG. 3). Dose response curves demonstrated that bacterial cells that were unable to engage CD14 and TLR4 yielded LPS that did not promote PRR loss from the cell surface, as compared to *E. coli* LPS (FIG. 3A). Interestingly, all strains that had a partial phenotype when bacterial cells were used as stimuli (e.g., those that stimulated TLR4, but not CD14) were fully stimulatory for both PRRs when purified LPS was used (FIG. 3B). This analysis therefore allowed the inventors to classify LPS from *Moritella* in a binary fashion-either immuno-stimulatory or immuno-silent. Note, that the term "silent" is used rather than "evasive", as the latter term suggests intent. The immuno-silent LPS preparations were isolated from *Moritella* 9, 28 and 36, the latter two of which were selected for further analyses.

Figure 4A:
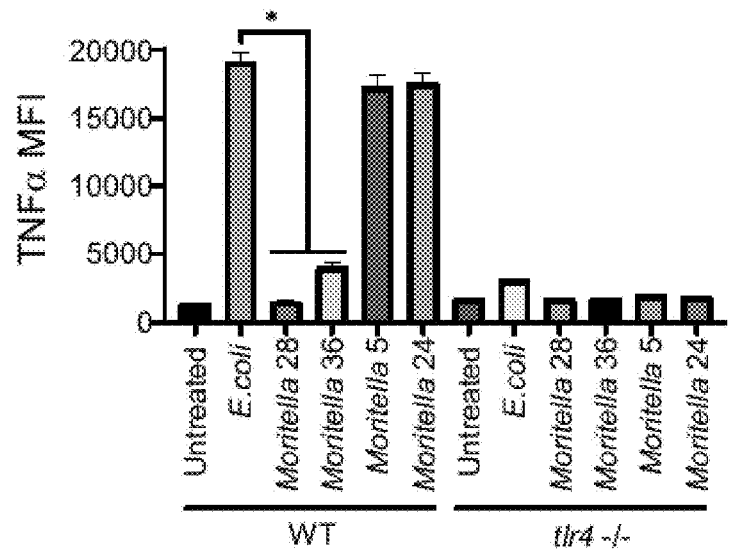
FIGS. 4A-4I. Functional analysis of purified LPS from *Moritella* strains silent (#28, 36) or stimulatory (#5, 24) to CD14 and TLR4 in murine iBMDMs. Accumulation of TNFα after 3.5 hrs (FIG. 4A) and phosphorylation of STAT1 after 2.5 hrs measured in wildtype and tlr4−/− iBMDMs incubated with 100 ng/mL purified LPS from *Moritella* strains or *E. coli* (FIG. 4B). The release of LDH, 3 hours post-electroporation of wildtype and casp11−/−iBMDMs with 1 μg of purified LPS from *Moritella* strains and *E. coli* (FIG. 4C). Cleavage of GSDMD, 3 hours post-electroporation of wildtype iBMDMs with 1 μg of purified LPS from *Moritella* strains and *E. coli* (FIG. 4D). Binding of HA-tagged caspase-11 to purified LPS supplied in excess (5 μg) from *Moritella* strains or *E. coli*, as measured by the ability of purified LPS to compete off biotinylated *E. coli* LPS (1 μg) (FIG. 4E). The production of pro-IL1β, 2.5 hours post-treatment of human THP1 cells incubated with 50 ng/mL of purified LPS from *Moritella* strains compared to purified *E. coli* LPS (FIG. 4F). Accumulation of TNFα, 4 hours post-treatment of human THP1 cells incubated with 100 ng/mL of purified LPS from *Moritella* strains compared to purified *E. coli* LPS (FIG. 4G). Engagement of human TLR4 in human TLR4/NF-κB/SEAP reporter HEK293 cells by purified LPS from *Moritella* strains compared to purified *E. coli* LPS (H). The release of LDH, 2.5 hours post-electroporation of human THP1 cells with 1 μg of purified LPS from *Moritella* strains compared to purified *E. coli* LPS (I). ($*p<0.01$ and $**\ p<0.001$)
Figure 4B:
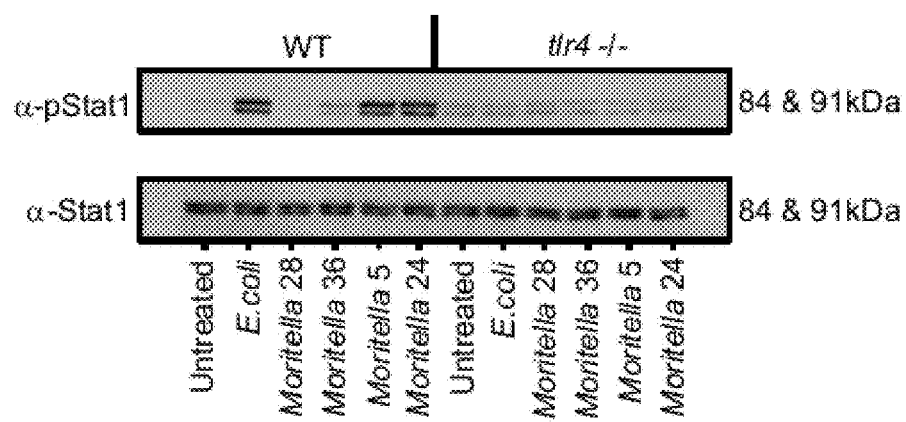

It was reasoned that if purified LPS from *Moritella* 28 and 36 are incapable of stimulating CD14 and TLR4, then these LPS preparations should be unable to stimulate TLR4-dependent inflammatory responses. Quantification of TNFα production and the phosphorylation of the transcription factor STAT1 report on TLR4 signaling from the plasma membrane or endosomes, respectively. These assays were used to assess macrophage responses to two stimulatory *Moritella* strains (#5 and 24) and two silent *Moritella* strains (#28 and 36). Consistent with these findings when assessing CD14 or TLR4 engagement, LPS from *Moritella* 5 and 24 induced TNFα production and STAT1 phosphorylation (FIGS. 4A, 4B). LPS from strains that did not stimulate CD14 or TLR4 were unable to induce these inflammatory responses (FIGS. 4A, 4B). All TNFα and STAT1 responses observed upon LPS stimulations were abolished when assays were performed on TLR4-deficient cells, as expected [24].

Figure 4C:
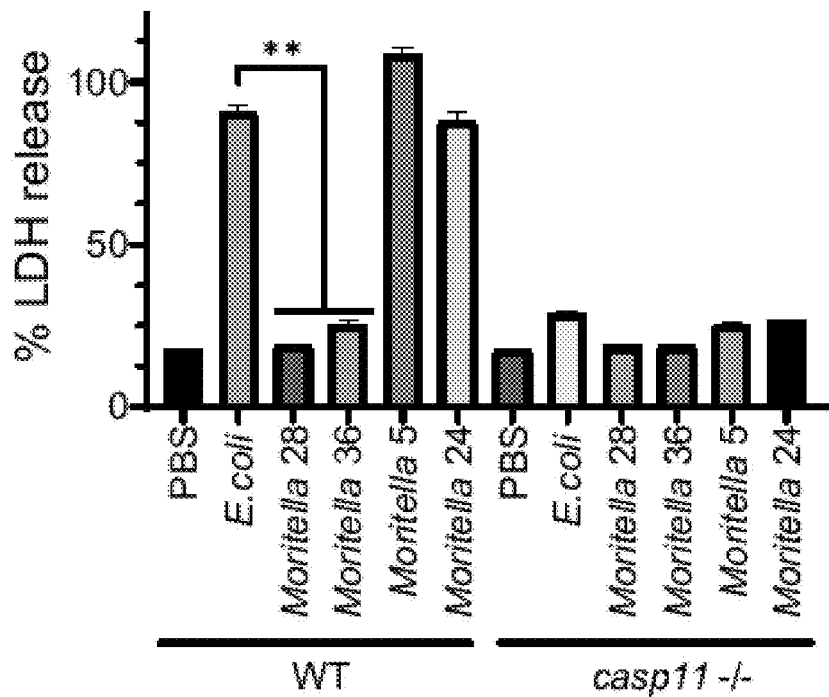
Figure 4D:
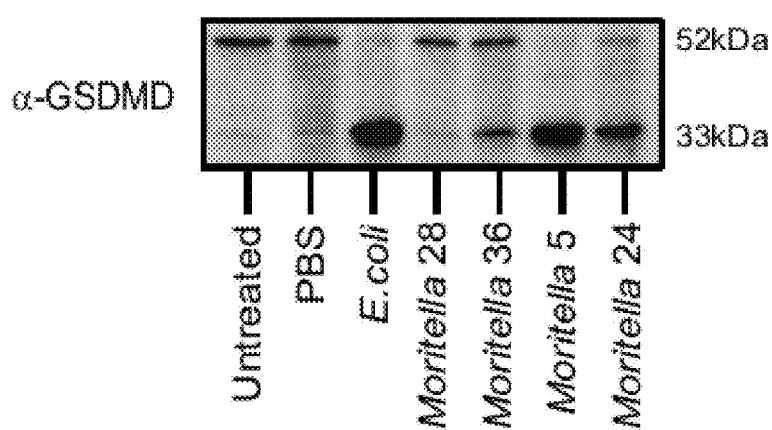
Figure 4E:
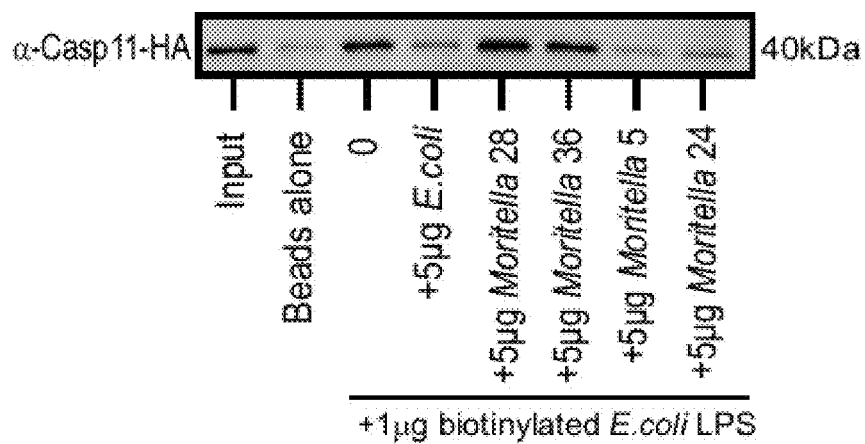

In addition to CD14 and TLR4, murine caspase-11 recognizes LPS in the cytosol of macrophages. Engagement of caspase-11 by *E. coli* LPS results in a lytic form of cell death called pyroptosis [25-28]. Pyroptosis can be assessed by monitoring the release of the cytosolic enzyme lactate dehydrogenase (LDH) into the extracellular space [29] along with the cleavage of the pore forming protein, gasdermin D (GSDMD) [30]. As expected [25, 27], electroporation of iBMDMs with *E. coli* LPS stimulated pyroptosis, as assessed by LDH release and GSDMD cleavage (FIGS. 4C, 4D). Purified LPS from *Moritella* 5 and 24 also stimulated robust LDH released after electroporation. Notably, LPS from *Moritella* strains 28 and 36, which did not stimulate CD14 and TLR4, induced no LDH release from iBMDMs (FIG. 4C). All LDH release observed was abolished when experiments were performed in caspase-11 deficient cells, as expected [26]. Consistent with these results, partial or no cleavage of GSDMD was observed in iBMDMs electroporated with purified LPS from *Moritella* strains 28 and 36 (FIG. 4D). Conversely, full cleavage of GSDMD was induced by purified LPS from *E. coli, Moritella* 5 and *Moritella* 24 (FIG. 4D). To determine if differences in pyroptosis induction related to an ability to interact with caspase-11, in vitro experiments with purified LPS were performed. Following a similar procedure to assess caspase-11 interactions with LPS [31, 32], the inventors assessed the ability of *Moritella* LPS to compete with biotinylated *E. coli* LPS for interactions with caspase-11. Biotinylated *E. coli* LPS formed a complex with caspase-11 in vitro (FIG. 4E). This interaction was prevented when reactions were performed in the presence of excess non-biotinylated *E. coli* LPS, or in the presence of immuno-stimulatory LPS from *Moritella* 5 or *Moritella* 24 (FIG. 4E). In contrast, LPS from the immuno-silent *Moritella* strains 28 and 36 did not compete with biotinylated *E. coli* LPS for binding to caspase-11 (FIG. 4E). These results suggest that only immuno-stimulatory LPS can interact with caspase-11, a finding that likely explains the pyroptosis-inducing activity of the *Moritella* strains examined.

Figure 4F:
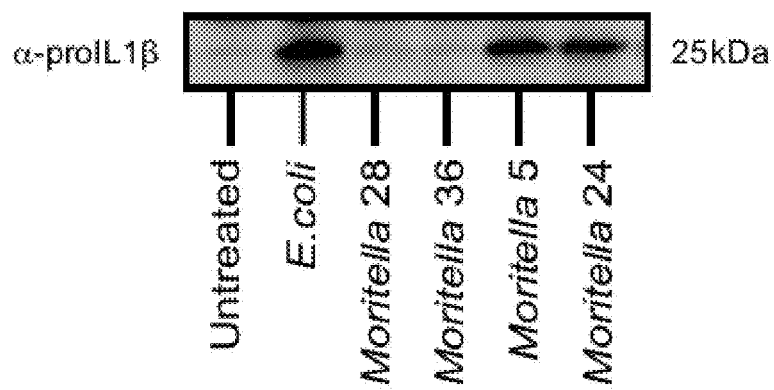
Figure 4G:
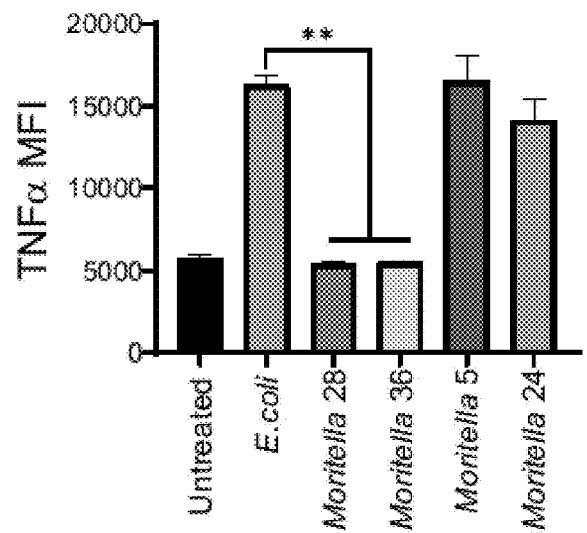
Figure 4H:
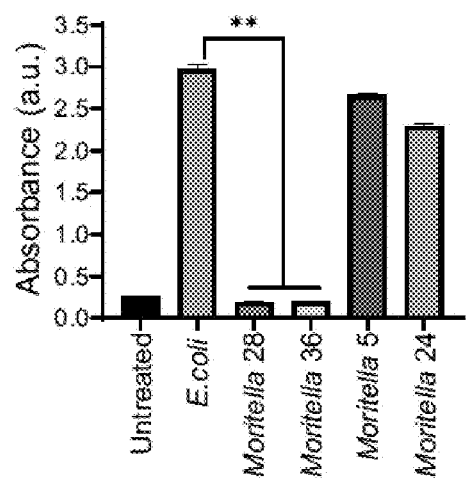
Figure 4I:
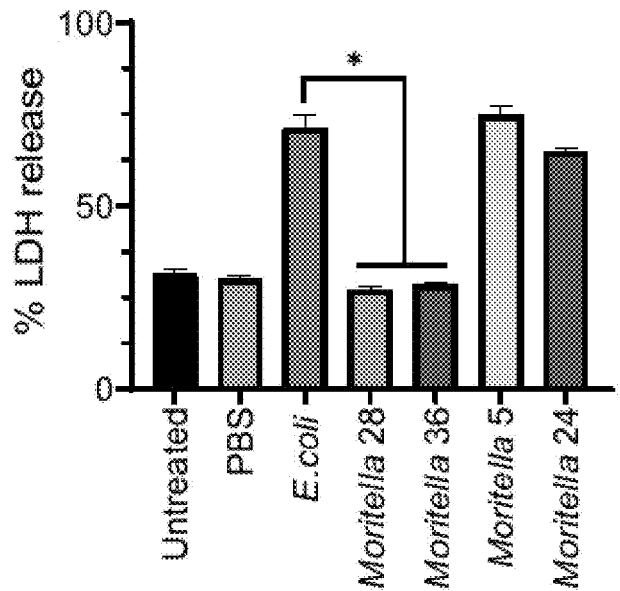

To establish whether the phenotypes observed in murine cells extend to other species, studies were performed in human THP1 monocytes and the LPS detection system from horseshoe crab crustaceans. Akin to the observations made in murine systems, LPS from *Moritella* 28 and 36 did not stimulate the production of pro-IL1β or TNFα in differentiated THP1 monocytes, as compared to LPS from *E. coli, Moritella* 5 or 24 (FIGS. 4F, 4G). To validate these findings, a minimalist HEK293-BLUE reporter system was used to assess direct engagement of human CD14, TLR4 and MD-2. In these cells, LPS interactions with these PRRs stimulates the secretion of alkaline phosphatase (SEAP). It was found that only immuno-stimulatory LPS induced SEAP production by HEK293-BLUE cells (FIG. 4H), thereby indicating that silent *Moritella* LPS from strains 28 and 36 do not engage PRRs in the TLR4 pathway. Finally, electroporated LPS from *Moritella* 5 and 24 induced THP1 monocyte pyroptosis to an extent comparable to that elicited by *E. coli* LPS (FIG. 4I). LPS from *Moritella* 28 and 36 induced minimal LDH release from electroporated THP1 monocytes (FIG. 4I).

Figure 5A:
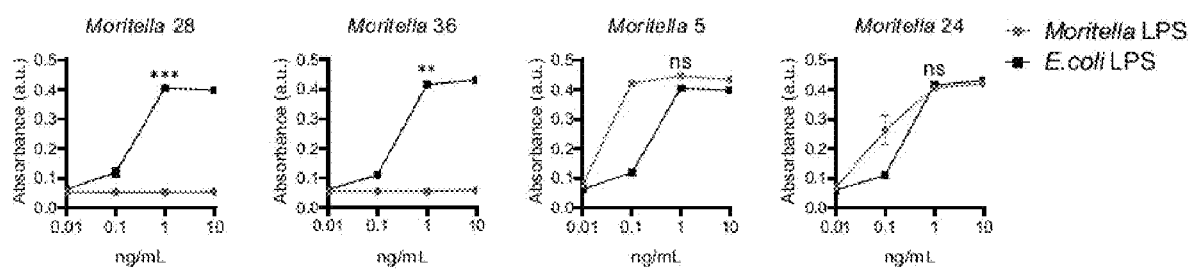
FIGS. 5A-5F. Cross species evasion of LPS receptor activity by deep-sea *Moritella* strains. Engagement of *Limulus polyphemus* factor C by purified LPS from *Moritella* strains compared to purified *E. coli* LPS (FIG. 5A). Inflammatory response to purified LPS from *Moritella* strains in vivo. IL-6 and TNFα plasma levels were measured 4 hours post intraperitoneal injection of mice with LPS from *Moritella* strains stimulatory (#5, 24) or silent (#28, 36) (FIG. 5B). 10 μg of purified *E. coli* LPS was compared to 10 μg of purified LPS or lipid A (LA) from *Moritella* strains visualized on a polyacrylamide gel stained with ProQ Emerald LPS staining solution (FIG. 5C). Accumulation of TNFα after 3.5 hr stimulations of iBMDMs with 100 ng/mL lipid A compared to purified LPS from *Moritella* strains (FIG. 5D). The release of LDH, 24 hours post-electroporation of iBMDMs with 1 μg of purified lipid A or LPS from *Moritella* strains (FIG. 5E). Engagement of *Limulus polyphemus* factor C by purified LPS and lipid A from *Moritella* strains (FIG. 5F). ($*p<0.01$, $\ p<0.001$ and $*<0.0001$)

The horseshoe crab *Limulus polyphemus* contains a distinct LPS detection system compared to terrestrial mammals [33, 34]. Upon binding of LPS to the protein Factor C from *L. polyphemus*, a complement-like protease cascade is stimulated that results in a defensive coagulation response [35]. Although it is an aquatic animal, *L. polyphemus* occupies shallow marine environments [36]. Thus, similar to mice and humans, *L. polyphemus* would be expected to rarely (if ever) encounter deep-sea bacteria in its natural environment. Interestingly, LPS preparations that could stimulate detection (or not) by mammalian LPS receptors exhibited the identical pattern of activity of engagement with Factor C. LPS from *Moritella* 28 and 36 did not engage Factor C, whereas LPS from *Moritella* 5 and 24 did so, similarly to *E. coli* LPS (FIG. 5A).

Figure 5B:
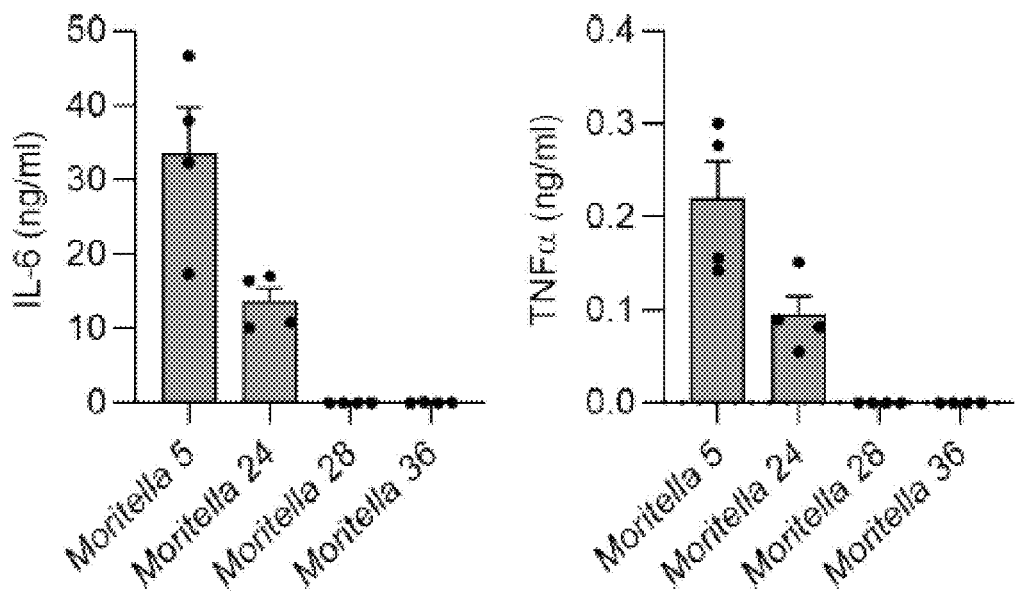

To determine if the immuno-silence of select *Moritella* LPS extended to an in vivo setting, inflammatory responses in mice were examined. Intraperitoneal injections of LPS from *Moritella* 5 and 24 induced the rapid accumulation of cytokines TNFα and IL-6 in the plasma (FIG. 5B). In contrast, these cytokines were not detected in the plasma of mice injected with *Moritella* 28 and 36 (FIG. 5B). Overall, symmetrical observations were made in mice, in human and murine cells, and in the in vitro system offered by the horseshoe crab. All these systems revealed immuno-silent LPS from select *Moritella*.

Figure 5C:
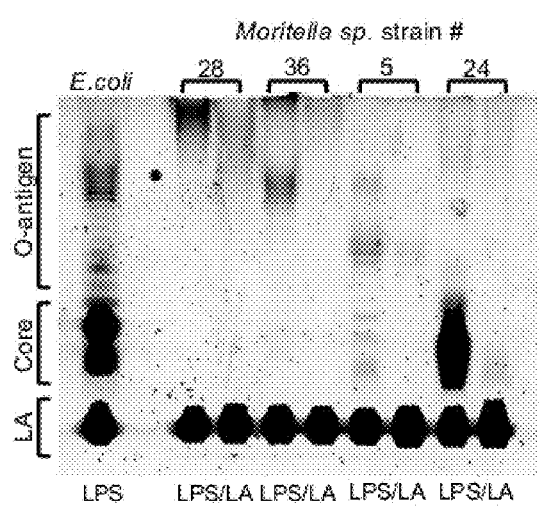
Figure 5D:
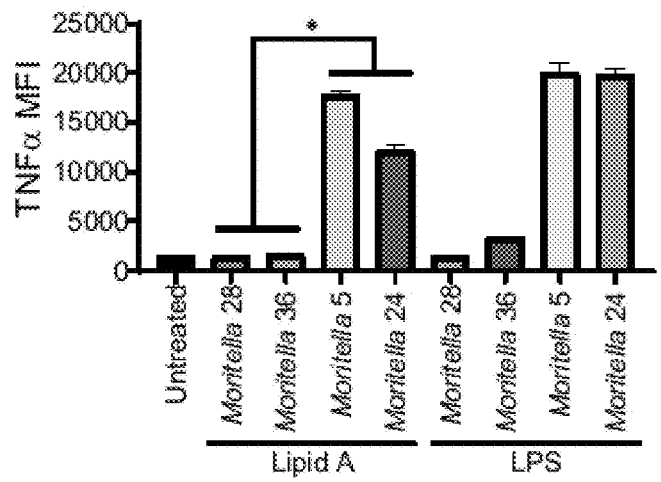
Figure 5E:
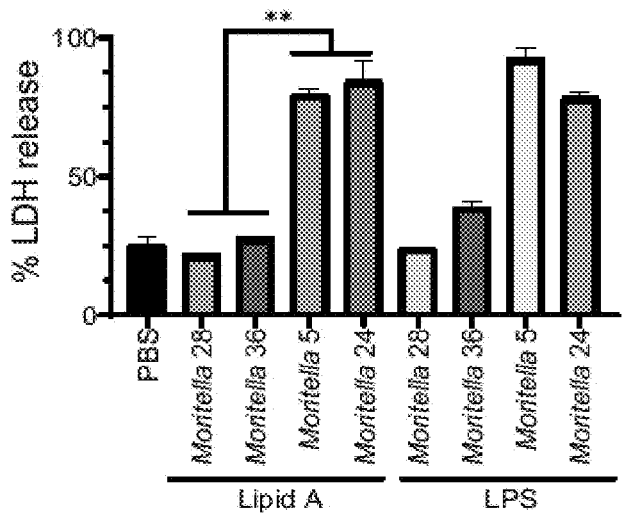
Figure 5F:
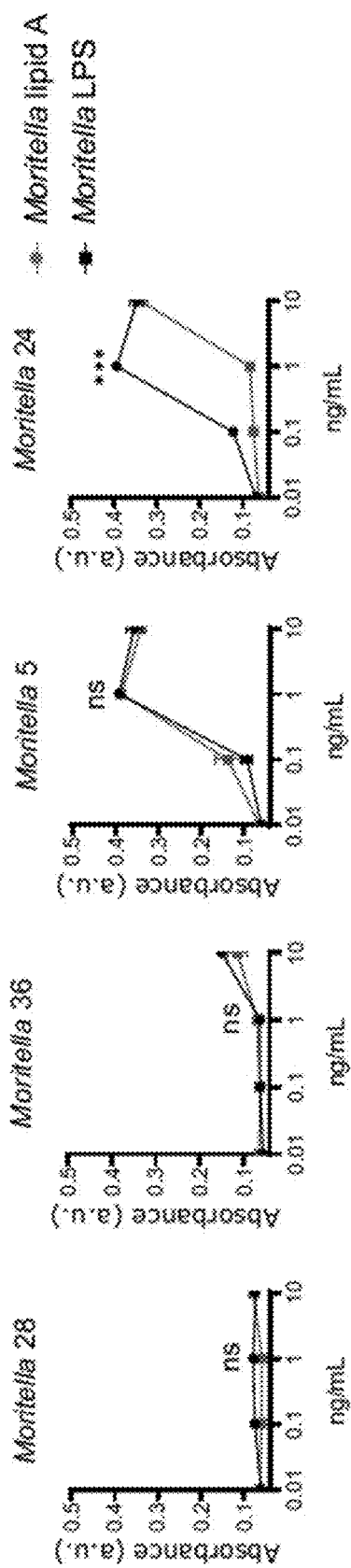

The LPS molecule of Gram-negative bacteria is composed of three distinct regions. The hydrophobic lipid A region anchors LPS to the bacterial outer membrane, whereas the water-soluble core oligosaccharide and O-antigen extend from the lipid A anchor into the aqueous extracellular space [37, 38]. It was possible that the silent activity of select *Moritella* strains was due to unique features of the O-antigen region that prevent PRR detection of lipid A. If this possibility was correct, then removal of the O-antigen should render immuno-silent molecules stimulatory. Thus, lipid A was purified after hydrolysis of the O-antigen from the LPS preparations of interest. This procedure resulted in the near-complete disappearance of the core and/or O-antigen regions, as assessed by silver staining (FIG. 5C). Contrary to the predictions of the inventors, removal of O-antigen did not increase the stimulatory activity of the immuno-silent lipid A preparations. Purified lipid A from immuno-stimulatory *Moritella* strains remained capable of inducing TNFα production, whereas purified lipid A from silent *Moritella* strains 28 and 36 remained incapable of inducing this inflammatory response (FIG. 5D). The same pattern of engagement for *Moritella* lipid A was observed for murine caspase-11 engagement, as indicated by pyroptosis induction after electroporation (FIG. 5E). Finally, Factor C engaged lipid A from *Moritella* 5 and 24 similarly to purified LPS from those same strains (FIG. 5F). Lipid A from *Moritella* 28 and 36 did not engage Factor C (FIG. 5F). These data indicate that lipid A was not being hidden from LPS receptors by other structural regions of the LPS molecule. Without wishing to be bound by theory, the inventors conclude that the silence of some deep-sea bacteria is intrinsic to the lipid A structure of LPS and, in the instance of the horseshoe crab, extends across the evolutionary tree of PRRs.

The features of lipid A that are associated with immuno-stimulatory activity of *E. coli* include a hexa-acylated and bis-phosphorylated di-glucosamine backbone [13, 39]. LPS structures that contain more (or less) than six acyl chains are weakly stimulatory to PRRs [40], and LPS structures containing mono-phosphorylated LPS are similarly immune-evasive [41]. Additionally, specific modifications to the lipid A, such as aminoarabinose [42], phosphoethanolamine (PEtn) [43, 44] or the presence of cardiolipin [45, 46] in LPS preparations are associated with non-stimulatory activity. To determine if deep-sea LPS display any of these immuno-evasive lipid A features, structural composition analysis was performed. The inventors first performed a large-scale analysis of lipid A structures isolated from all 50 deep-sea bacteria examined at the start of this study (Table 3).

TABLE 3

MALDI-TOF MS structural data and endogenous murine CD14-TLR4 engagement by bacterial strain. Structural data reported for each strain: 1) The primary m/z peak value, 2) the number of acyl chains predicted for the m/z peak value reported, 3) mono-phosphorylation of the lipid A di-glucosamine backbone, and 4) the addition of phosphoethanolamine (PEtn) to the lipid A di-glucosamine backbone. CD14-TLR4 engagement is reported as Yes/No compared to *E. coli*.

| Strain Identification | 1° ionizable m/z peak value | Predicted # acyl | Minor mono-$PO_4^{3-}$ (Yes/No) | PEtn addition (Yes/No) | Cardiolipin (Yes/No) | CD14 internalization | TLR4/MD2 dimerization |
|---|---|---|---|---|---|---|---|
| *E. coli* | 1798 | 6 | No | No | No | Yes | Yes |
| *Colwellia* 1 | 2048 | 7 | Yes | No | No | No | No |
| *Shewenella* 1 | 1727 | 6 | Yes | No | No | No | No |
| *Moritella* 27 | 1792 | 6 | Yes | No | No | No | No |
| *Moritella* 9 | 1755 | 6 | Yes | Yes | No | No | No |
| *Moritella* 28 | 1739 | 6 | No | No | No | No | No |
| *Colwellia* 3 | 2047 | 7 | Yes | Yes | No | No | No |
| *Moritella* 23 | 1739 | 6 | No | No | No | No | No |
| *Moritella* 11 | 1798 | 6 | Yes | Yes | No | No | No |
| *Moritella* 32 | 1768 | 6 | No | No | No | No | No |
| *Colwellia* 2 | 2020 | 7 | Yes | No | No | No | No |
| *Moritella* 36 | 1739 | 6 | No | No | No | No | No |
| *Moritella* 8 | 1658 | 6 | No | No | No | No | Yes |
| *Moritella* 4 | 1766 | 6 | Yes | Yes | No | No | Yes |
| *Moritella* 31 | 1740 | 6 | Yes | No | No | No | Yes |
| *Moritella* 41 | 1740 | 6 | No | No | No | No | Yes |
| *Moritella* 34 | 1739 | 6 | Yes | No | No | No | No |
| *Moritella* 40 | 1739 | 6 | Yes | No | No | No | No |
| *Moritella* 2 | 1740 | 6 | Yes | No | No | No | No |
| *Halomonas* 1 | 1739 | 6 | Yes | No | No | No | No |
| *Moritella* 33 | 1739 | 6 | Yes | No | No | No | No |
| *Moritella* 6 | 1740 | 6 | Yes | No | No | No | No |
| *Moritella* 35 | 1766 | 6 | Yes | No | No | No | Yes |
| *Moritella* 14 | 1790 | 6 | Yes | No | No | No | No |
| *Moritella* 29 | 1740 | 6 | Yes | No | Yes | No | No |
| *Moritella* 42 | 1739 | 6 | No | No | No | No | Yes |
| *Moritella* 5 | 1739 | 6 | No | No | No | No | No |
| *Moritella* 43 | 1769 | 6 | Yes | No | No | No | Yes |
| *Moritella* 30 | 1764 | 6 | No | No | No | No | No |
| *Moritella* 26 | 1766 | 6 | Yes | No | No | No | No |
| *Moritella* 18 | 1767 | 6 | Yes | No | No | No | Yes |
| *Moritella* 19 | 1766 | 6 | Yes | No | No | No | Yes |
| *Moritella* 22 | 1739 | 6 | Yes | No | No | No | Yes |
| *Moritella* 16 | 1764 | 6 | Yes | No | No | No | No |
| *Moritella* 39 | 1766 | 6 | No | No | No | No | No |
| *Moritella* 37 | 1766 | 6 | No | No | No | No | Yes |
| *Moritella* 20 | 1767 | 6 | Yes | No | No | No | No |
| *Moritella* 17 | 1790 | 6 | No | No | Yes | Yes | Yes |
| *Moritella* 38 | 1768 | 6 | Yes | No | No | Yes | Yes |
| *Moritella* 21 | 1659 | 6 | No | No | Yes | Yes | Yes |
| *Vibrio* 1 | 1754 | 6 | No | No | Yes | No | Yes |
| *Moritella* 45 | 1807 | 6 | No | No | No | Yes | Yes |
| *Moritella* 10 | 1767 | 6 | Yes | No | No | No | Yes |
| *Moritella* 44 | 1807 | 6 | No | No | Yes | Yes | Yes |

TABLE 3-continued

MALDI-TOF MS structural data and endogenous murine CD14-TLR4 engagement by bacterial strain. Structural data reported for each strain: 1) The primary m/z peak value, 2) the number of acyl chains predicted for the m/z peak value reported, 3) mono-phosphorylation of the lipid A di-glucosamine backbone, and 4) the addition of phosphoethanolamine (PEtn) to the lipid A di-glucosamine backbone. CD14-TLR4 engagement is reported as Yes/No compared to *E. coli*.

| Strain Identification | 1° ionizable m/z peak value | Predicted # acyl | Minor mono-PO$_4^{3-}$ (Yes/No) | PEtn addition (Yes/No) | Cardiolipin (Yes/No) | CD14 internalization | TLR4/MD2 dimerization |
|---|---|---|---|---|---|---|---|
| *Moritella* 7 | 1766 | 6 | Yes | No | No | Yes | Yes |
| *Moritella* 25 | 1655 | 6 | No | No | Yes | Yes | Yes |
| *Moritella* 3 | 1766 | 6 | Yes | No | No | Yes | Yes |
| *Moritella* 15 | 1766 | 6 | Yes | No | No | No | Yes |
| *Moritella* 13 | 1764 | 6 | Yes | No | No | No | Yes |
| *Moritella* 12 | 1791 | 6 | No | No | No | Yes | Yes |
| *Moritella* 24 | 1784 | 6 | No | No | No | Yes | Yes |

The inventors extracted lipid A and predicted structural composition by MALDI-TOF mass spectrometry (MS) in the negative ion mode [47-49]. Mass spectral data were used to predict the following within lipid A: (1) the number of acyl chains likely to be present, (2) the loss of a phosphate from the di-glucosamine sugar backbone (mono-phosphorylation), (3) the addition of aminoarabinose or phosphoethanolamine (PEtn) to the di-glucosamine sugar backbone and 4) the presence of cardiolipin in the lipid A extractions.

These structural analyses revealed that several bacteria contain immuno-silent modifications to their lipid A. Specifically, the *Colwellia* strains examined contained a primary ionizable m/z peak >2000 atomic mass units (amu), which is predicted to be hepta-acylated (Table 3). Additionally, the inventors observed PEtn additions (Δ m/z of 123 amu) to the lipid A backbone of select strains, as well as the presence of cardiolipin (repeating Δm/z of 12 amu) in others (Table 3). These bacteria were identified in FIG. 2 as containing LPS that prevents detection by CD14 or TLR4, an observation that, without wishing to be bound by theory, is likely explained by the structural changes to the lipid A identified.

In contrast to the examples offered above, which are consistent with current views of LPS-PRR interactions, most strains examined (including all 44 *Moritella* strains) contained a primary ionizable m z peak ranging from 1650-1800 amu (Table 3). These spectra are consistent with hexa-acylated lipid A being present in all *Moritella* examined. Similar findings were observed for lipid A structures from *Halomonas, Shewanella,* and *Vibrio* strains (Table 3). All *Moritella* strains were also predicted to contain bis-phosphorylated lipid A, although some strains had minor populations of mono-phosphorylation (Δm/z of 80) (Table 3). These features of lipid A—hexa-acylated and bis-phosphorylated—are commonly associated with immuno-stimulatory LPS, such as that from *E. coli*. Yet, these *E. coli*-like lipid A structures from deep-sea bacteria were either immuno-stimulatory or immuno-silent. Indeed, of the *Moritella* examined structurally, 79.5% (35/44) displayed evidence of immuno-silence when bacteria were used to stimulate murine cells (FIG. 2). The immuno-silence of *Moritella* 9 may be explained by the presence of a PEtn on its lipid A di-glucosamine backbone (Table 3) [43, 50]. *Moritella* 28 and 36, in contrast, did not have any observable backbone modifications to explain why their LPS was immuno-silent across multiple experimental systems.

To confirm the MALDI-TOF MS analyses generated from acid-extracted lipid A for silent and stimulatory *Moritella*, the inventors employed a newly described gentle extraction method, known as Fast Lipid Analysis Technique (FLAT) [51]. FLAT enables the detection of very small quantities of lipid A within a bacterial colony, without the need for centrifugation or lyophilization. Bacterial colonies were smeared directly onto a MALDI plate and lipid A was extracted rapidly in a citric acid buffer. Analysis was then performed in the negative ion mode on a Bruker Microflex. The mass spectra obtained by this distinct method were consistent with those obtained using other methods (Table 3), in that all four *Moritella* strains of interest (2 immuno-stimulatory and 2 immuno-silent) are predicted to be hexa-acylated and bis-phosphorylated (FIG. 6A).

To further assess the structural features of *Moritella* lipid A, gas chromatography-mass spectrometry (GC-MS) was performed. This analysis enables the determination of the composition of acyl chains present on lipid A [52, 53]. It was found that immuno-silent strains (*Moritella* 28 and 36) contained lipid A with the highest amount of C16 acyl chains (FIG. 6B). Conversely, the stimulatory strains contained lipid A with zero C16 chains (*Moritella* 5) or low amounts of C16 chains (*Moritella* 24). Instead, these stimulatory strains had mainly C12 and C14 length acyl chains (FIG. 6B). These findings were notable, as C14 and C12 length acyl chains are the optimal lengths for robust activation of TLR4 signaling [54, 55]. C16 chains, in contrast, are recognized as being non-optimal lengths for productive interactions with MD-2 [56]. Indeed, in the context of synthetic lipid A mimics, those with C16 chains cannot bind MD-2 at all—and are consequently immuno-silent [56]. Consistent with this idea, the highest amount of C16 acyl chains were found in the immuno-silent *Moritella* strains 28 and 36. Other than these C16 differences, the GC analysis revealed similar patterns of fatty acid composition in the strains examined, with no strain-specific differences in short or odd-length fatty acids detected. Thus, the inventors propose that immuno-silence is not the result of an unusual addition to the lipid A molecules found in the deep sea, but rather results from the existence of abundant C116 acyl chains found in select strains, which determines PRR interactions.

It was next sought to determine how each *Moritella* strain related to each other and to previously identified *Moritella* species. A combination of Nanopore and Illumina sequencing was used to determine the genome sequence of the two silent and the two stimulatory *Moritella* strains (Table 4).

TABLE 4

*Moritella* genome summary table. Name of *Moritella* sequenced, isolation location, and isolation depth are reported along with the following information: 1) Sequencing coverage, 2) GC content, 3) genome size, 4) replicons, 5) longest contig, 6) predicted total coding sequences (CDS), and 7) NCBI accession number. All genomes are complete; note that *Moritella rawaki* 24 contains two plasmids.

| Name | *Moritella rawaki* 24 | *Moritella oceanus* 36 | *Moritella oceanus* 5 | *Moritella oceanus* 28 |
|---|---|---|---|---|
| Isolation location | *Rawaki* | Te Terina | Te Marena | Te Terina |
| Isolation Depth (m) | 601 | 1148 | 1266 | 1148 |
| Isolation Date | 2017 Oct. 18 | 2017 Oct. 18 | 2017 Oct. 16 | 2017 Oct. 18 |
| Sequencing Coverage | 460x | 233x | 198x | 191x |
| GC content (%) | 39.79 | 39.91 | 39.96 | 39.93 |
| Genome Size (bp) | 4,731,068 | 5,037,375 | 4,991,674 | 5,097,422 |
| Replicons | 3 | 1 | 1 | 1 |
| Longest Contig (bp) | 4,638,679 | 5,037,375 | 4,991,674 | 5,097,422 |
| Predicted Total CDSs | 4,076 | 4,290 | 4,255 | 4,341 |
| NCBI Genome Accession | CP056123 — | CP056120 | CP056122 | CP056121 |

Figure 6C:
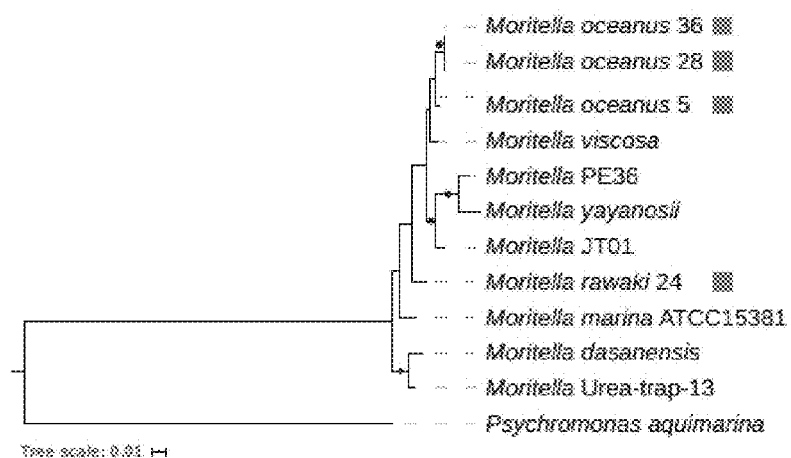
Figure 6D:
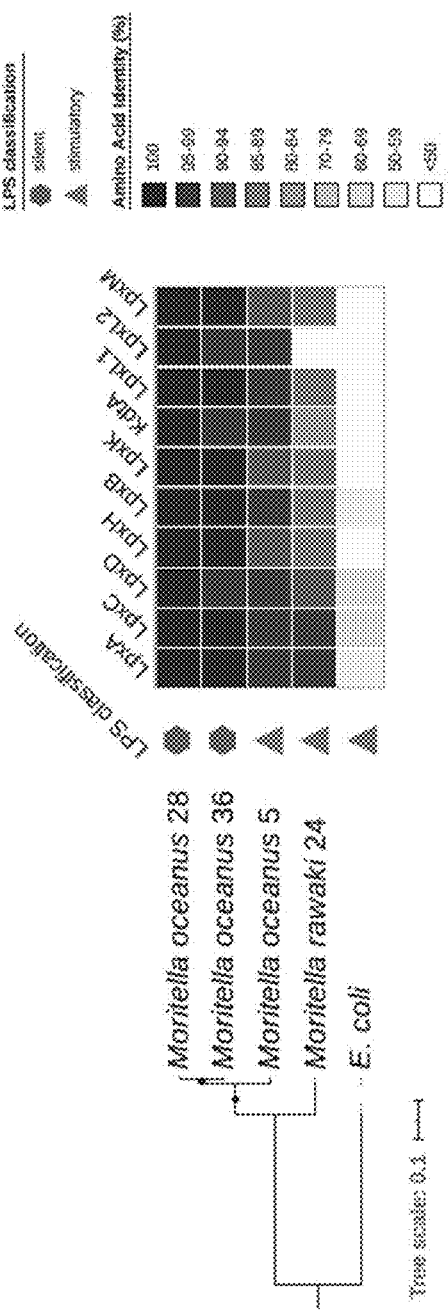

The phylogenetic relationship between these strains and other sequenced *Moritella* genomes was determined (FIG. 6C). This analysis indicated that the four *Moritella* strains described herein are novel and evolutionarily distinct from known *Moritella*. Average nucleotide identity analysis [57, 58] indicated that *Moritella* 24 represents a distinct species, whereas *Moritella* 5, 28, and 36 represent substrains of a second new species (Table 5).

TABLE 5

Average nucleotide identity analysis of sequenced *Moritella* genomes vs. other *Moritella* genome assemblies from NCBI Genbank. For analysis, the query genome was compared to reference genome and the percent (%) nucleotide identity is reported with the number of bidirectional fragment mappings and the number of total query fragments analyzed.

| Query Genome | Reference Genome | Average Nucleotide Identity (%) | # Bidirectional fragment mappings | Total query fragments |
|---|---|---|---|---|
| *Moritella rawaki* 24 | *Moritella rawaki* 24 | 100.0 | 1571 | 1576 |
| *Moritella rawaki* 24 | *Moritella oceanus* 5 | 84.6 | 1098 | 1576 |
| *Moritella rawaki* 24 | *Moritella oceanus* 28 | 84.6 | 1115 | 1576 |
| *Moritella rawaki* 24 | *Moritella oceanus* 36 | 84.6 | 1069 | 1576 |
| *Moritella rawaki* 24 | *Moritella viscosa* (GCF_000953735.1) | 84.3 | 1076 | 1576 |
| *Moritella rawaki* 24 | *Moritella* JT01 (GCF_001574435.1) | 84.3 | 1073 | 1576 |
| *Moritella rawaki* 24 | *Moritella marina* ATCC15381 (GCF_008931805.1) | 84.2 | 1058 | 1576 |
| *Moritella rawaki* 24 | *Moritella* PE36 (GCA_000170855.1) | 84.1 | 1019 | 1576 |
| *Moritella rawaki* 24 | *Moritella* Urea-trap-13 (GCF_002836355.1) | 83.9 | 1015 | 1576 |
| *Moritella rawaki* 24 | *Moritella yayanosii* (GCA_900465055.1) | 83.9 | 956 | 1576 |
| Moritella rawaki 24 | *Moritella dasanensis* ArB 0140 (GCA_000276805.1) | 83.8 | 1028 | 1576 |
| *Moritella oceanus* 28 | *Moritella oceanus* 28 | 100.0 | 1694 | 1699 |
| *Moritella oceanus* 28 | *Moritella oceanus* 36 | 99.1 | 1554 | 1699 |
| *Moritella oceanus* 28 | *Moritella oceanus* 5 | 96.8 | 1475 | 1699 |
| *Moritella oceanus* 28 | *Moritella* JT01 (GCF_001574435.1) | 93.3 | 1382 | 1699 |
| *Moritella oceanus* 28 | *Moritella viscosa* (GCF_000953735.1) | 92.0 | 1300 | 1699 |
| *Moritella oceanus* 28 | *Moritella* PE36 (GCA_000170855.1) | 86.6 | 1153 | 1699 |
| *Moritella oceanus* 28 | *Moritella yayanosii* (GCA_900465055.1) | 86.0 | 1076 | 1699 |
| *Moritella oceanus* 28 | *Moritella rawaki* 24 | 84.6 | 1097 | 1699 |
| *Moritella oceanus* 28 | *Moritella* Urea-trap-13 (GCF_002836355.1) | 84.0 | 1054 | 1699 |
| *Moritella oceanus* 28 | *Moritella marina*. ATCC15381 (GCF 008931805.1) | 83.8 | 1042 | 1699 |
| *Moritella oceanus* 28 | *Moritella dasanensis* ArB 0140 (GCA_000276805.1) | 83.7 | 1046 | 1699 |
| *Moritella oceanus* 36 | *Moritella oceanus* 36 | 100.0 | 1672 | 1679 |
| *Moritella oceanus* 36 | *Moritella oceanus* 28 | 99.1 | 1550 | 1679 |
| *Moritella oceanus* 36 | *Moritella oceanus* 5 | 96.8 | 1444 | 1679 |
| *Moritella oceanus* 36 | *Moritella* JT01 (GCF_001574435.1) | 93.3 | 1355 | 1679 |
| *Moritella oceanus* 36 | *Moritella viscosa* GCF_000953735.1 | 91.9 | 1283 | 1679 |
| *Moritella oceanus* 36 | *Moritella* PE36 (GCA_000170855.1) | 86.5 | 1137 | 1679 |
| *Moritella oceanus* 36 | *Moritella yayanosii* (GCA_900465055.1) | 86.0 | 1057 | 1679 |
| *Moritella oceanus* 36 | *Moritella rawaki* 24 | 84.6 | 1067 | 1679 |
| *Moritella oceanus* 36 | *Moritella* Urea-trap-13 (GCF_002836355.1) | 84.0 | 1057 | 1679 |
| *Moritella oceanus* 36 | *Moritella dasanensis* ArB 0140 (GCA_000276805.1) | 83.8 | 1043 | 1679 |
| *Moritella oceanus* 36 | *Moritella marina*. ATCC15381 (GCF_008931805.1) | 83.8 | 1037 | 1679 |
| *Moritella oceanus* 5 | *Moritella oceanus* 5 | 100.0 | 1659 | 1663 |
| *Moritella oceanus* 5 | *Moritella oceanus* 28 | 96.8 | 1468 | 1663 |
| *Moritella oceanus* 5 | *Moritella oceanus* 36 | 96.8 | 1448 | 1663 |
| *Moritella oceanus* 5 | *Moritella* JT01 (GCF_001574435.1) | 93.5 | 1382 | 1663 |
| *Moritella oceanus* 5 | *Moritella viscosa* (GCF_000953735.1) | 92.1 | 1312 | 1663 |
| *Moritella oceanus* 5 | *Moritella* PE36 (GCA_000170855.1) | 86.6 | 1168 | 1663 |
| *Moritella oceanus* 5 | *Moritella yayanosii* (GCA_900465055.1) | 86.1 | 1080 | 1663 |

TABLE 5-continued

Average nucleotide identity analysis of sequenced *Moritella* genomes vs. other *Moritella* genome assemblies from NCBI Genbank. For analysis, the query genome was compared to reference genome and the percent (%) nucleotide identity is reported with the number of bidirectional fragment mappings and the number of total query fragments analyzed.

| Query Genome | Reference Genome | Average Nucleotide Identity (%) | # Bidirectional fragment mappings | Total query fragments |
|---|---|---|---|---|
| *Moritella oceanus* 5 | *Moritella rawaki* 24 | 84.8 | 1080 | 1663 |
| *Moritella oceanus* 5 | *Moritella* Urea-trap-13 (GCF_002836355.1) | 84.2 | 1042 | 1663 |
| *Moritella oceanus* 5 | *Moritella dasanensis* ArB 0140 (GCA_000276805.1) | 83.9 | 1041 | 1663 |
| *Moritella oceanus* 5 | *Moritella marina*. ATCC15381 (GCF_008931805.1) | 83.7 | 1069 | 1663 |

The inventors tentatively propose these species be designated *Moritella oceanus* (formerly *Moritella* 5, 28, and 36) and *Moritella rawaki* (formerly *Moritella* 24).

Pangenome analysis revealed a set of protein-coding sequences that distinguished the two immuno-silent from the two immuno-stimulatory strains. Specifically, both immuno-silent *Moritella* strains encoded a common set of 192 unique protein-coding sequences (Table 6) not found in either immuno-stimulatory strain. 55 protein-coding genes were found exclusively in both stimulatory strains (Table 7). Most of these genes lack an annotated function. Whether any of these unique genes affect immuno-silence or detection is unknown, as is the degree of sequence conservation across other (un-sequenced, but behaviorally similar (as in FIG. 2)) *Moritella* strains.

TABLE 6

Gene clusters unique to the *Moritella* strains containing immuno-silent LPS (*Moritella oceanus* 28 and *M. oceanus* 36) and not in the immuno-stimulatory strains. NCBI accession IDs are provided for the putative protein-coding genes belonging to each of the 192 putative protein-coding sequence clusters.

| Cluster | Annotated Function | *Moritella oceanus* 28 | *Moritella oceanus* 36 |
|---|---|---|---|
| cluster101 | hypothetical protein | HWV02_07580;HWV02_07585 | HWV03_07585;HWV03_07590 |
| cluster102 | RHS repeat protein | HWV02_07595;HWV02_04535 | HWV03_07600;HWV03_04540 |
| cluster103 | hypothetical protein | HWV02_11475;HWV02_11485 | HWV03_11080;HWV03_11090 |
| cluster24 | ISNCY family transposase | HWV02_18225 | HWV03_08010;HWV03_17885; HWV03_17920;HWV03_17955; HWV03_17995;HWV03_11130 |
| cluster3078 | hypothetical protein | HWV02_08300 | HWV03_10240;HWV03_04470 |
| cluster3079 | hypothetical protein | HWV02_18300 | HWV03_16280;HWV03_16300 |
| cluster3081 | hypothetical protein | HWV02_22215 | HWV03_21815; HWV03_21940 |
| cluster3097 | AHH domain-containing protein | HWV02_12230; HWV02_13490 | HWV03_11855 |
| cluster3779 | DUF547 domain-containing protein | HWV02_05570 | HWV03_05645 |
| cluster3781 | PhzF family phenazine biosynthesis protein | HWV02_05790 | HWV03_05840 |
| cluster3782 | Ig-like domain-containing protein | HWV02_06080 | HWV03_06110 |
| cluster3783 | porin family protein | HWV02_06120 | HWV03_06150 |
| cluster3784 | Qnr family pentapeptide repeat protein | HWV02_06125 | HWV03_06155 |
| cluster3785 | RNA polymerase sigma factor | HWV02_06295 | HWV03_06325 |
| cluster3786 | UpxY family transcription antiterminator | HWV02_06300 | HWV03_06330 |
| cluster3787 | glycoside hydrolase family protein | HWV02_06305 | HWV03_06335 |
| cluster3788 | hypothetical protein | HWV02_06310 | HWV03_06340 |
| cluster3789 | hypothetical protein | HWV02_06315 | HWV03_06345 |
| cluster3790 | phage tail sheath family protein | HWV02_06320 | HWV03_06350 |
| cluster3791 | hypothetical protein | HWV02_06330 | HWV03_06360 |
| cluster3792 | phage tail protein | HWV02_06335 | HWV03_06365 |
| cluster3793 | hypothetical protein | HWV02_06345 | HWV03_06375 |
| cluster3794 | hypothetical protein | HWV02_06350 | HWV03_06380 |
| cluster3795 | hypothetical protein | HWV02_06355 | HWV03_06385 |
| cluster3796 | GPW/gp25 family protein | HWV02_06360 | HWV03_06390 |
| cluster3797 | hypothetical protein | HWV02_06365 | HWV03_06395 |
| cluster3798 | hypothetical protein | HWV02_06370 | HWV03_06400 |
| cluster3799 | tail fiber protein | HWV02_06375 | HWV03_06405 |
| cluster3800 | hypothetical protein | HWV02_06380 | HWV03_06410 |
| cluster3801 | hypothetical protein | HWV02_06385 | HWV03_06415 |
| cluster3802 | hypothetical protein | HWV02_06390 | HWV03_06420 |
| cluster3803 | hypothetical protein | HWV02_06395 | HWV03_06425 |
| cluster3804 | hypothetical protein | HWV02_06400 | HWV03_06430 |
| cluster3805 | hypothetical protein | HWV02_06405 | HWV03_06435 |

TABLE 6-continued

Gene clusters unique to the *Moritella* strains containing immuno-silent LPS (*Moritella oceanus* 28 and *M. oceanus* 36) and not in the immuno-stimulatory strains. NCBI accession IDs are provided for the putative protein-coding genes belonging to each of the 192 putative protein-coding sequence clusters.

| Cluster | Annotated Function | *Moritella oceanus* 28 | *Moritella oceanus* 36 |
|---|---|---|---|
| cluster3806 | LysR family transcriptional regulator | HWV02_06885 | HWV03_06915 |
| cluster3807 | hypothetical protein | HWV02_06890 | HWV03_06920 |
| cluster3808 | hypothetical protein | HWV02_06895 | HWV03_06925 |
| cluster3811 | ester cyclase | HWV02_07515 | HWV03_07520 |
| cluster3812 | methyltransferase domain-containing protein | HWV02_07520 | HWV03_07525 |
| cluster3813 | hypothetical protein | HWV02_07530 | HWV03_07535 |
| cluster3814 | hypothetical protein | HWV02_07535 | HWV03_07540 |
| cluster3815 | toxin | HWV02_07590 | HWV03_07595 |
| cluster3816 | L,D-transpeptidase family protein | HWV02_08110 | HWV03_07880 |
| cluster3817 | hypothetical protein | HWV02_08115 | HWV03_07885 |
| cluster3818 | RHS repeat-associated core domain-containing protein | HWV02_18725 | HWV03_08035 |
| cluster3819 | metallophosphoesterase | HWV02_08380 | HWV03_08175 |
| cluster3820 | hypothetical protein | HWV02_08420 | HWV03_08215 |
| cluster3821 | aminotransferase class I/II-fold pyridoxal phosphate-dependent enzyme | HWV02_08610 | HWV03_08390 |
| cluster3822 | hypothetical protein | HWV02_08615 | HWV03_08395 |
| cluster3823 | RidA family protein | HWV02_08670 | HWV03_08450 |
| cluster3824 | DMT family transporter | HWV02_08675 | HWV03_08455 |
| cluster3825 | SPFH domain-containing protein | HWV02_08785 | HWV03_08580 |
| cluster3827 | DUF285 domain-containing protein | HWV02_08925 | HWV03_08670 |
| cluster3829 | ketopantoate reductase family protein | HWV02_08960 | HWV03_08715 |
| cluster3830 | citrate lyase ligase | HWV02_00940 | HWV03_00940 |
| cluster3833 | hypothetical protein | HWV02_09325 | HWV03_09060 |
| cluster3834 | phage integrase N-terminal SAM-like | HWV02_09370 | HWV03_09105 |
| cluster3835 | type VI secretion system amidase effector protein Tae4 | HWV02_09375 | HWV03_09110 |
| cluster3836 | type II secretion system protein | HWV02_09380 | HWV03_09115 |
| cluster3837 | hypothetical protein | HWV02_09390 | HWV03_09125 |
| cluster3838 | alpha/beta hydrolase | HWV02_09395 | HWV03_09135 |
| cluster3839 | gamma-glutamylcyclotransferase | HWV02_09405 | HWV03_09145 |
| cluster3840 | class I SAM-dependent methyltransferase | HWV02_09835 | HWV03_09550 |
| cluster3843 | GNAT family N-acetyltransferase | HWV02_09855 | HWV03_09575 |
| cluster3844 | DUF1330 domain-containing protein | HWV02_09860 | HWV03_09580 |
| cluster3845 | hypothetical protein | HWV02_09900 | HWV03_09620 |
| cluster3846 | ATP/GTP-binding protein | HWV02_10185 | HWV03_09870 |
| cluster3847 | helix-turn-helix transcriptional regulator | HWV02_10190 | HWV03_09875 |
| cluster3848 | porin family protein | HWV02_10380 | HWV03_10065 |
| cluster3849 | hypothetical protein | HWV02_10385 | HWV03_10070 |
| cluster3850 | RICIN domain-containing protein | HWV02_10445 | HWV03_10130 |
| cluster3851 | DUF4261 domain-containing protein | HWV02_10480 | HWV03_10160 |
| cluster3852 | hypothetical protein | HWV02_10485 | HWV03_10165 |
| cluster3853 | immunity 53 family protein | HWV02_10490 | HWV03_10170 |
| cluster3854 | hypothetical protein | HWV02_10495 | HWV03_10175 |
| cluster3855 | type I methionyl aminopeptidase | HWV02_10500 | HWV03_10180 |
| cluster3856 | ParD-like family protein | HWV02_10505 | HWV03_10185 |
| cluster3858 | hypothetical protein | HWV02_10750 | HWV03_10355 |
| cluster3859 | hypothetical protein | HWV02_10755 | HWV03_10360 |
| cluster3860 | type II secretion system protein | HWV02_10760 | HWV03_10365 |

TABLE 6-continued

Gene clusters unique to the *Moritella* strains containing immuno-silent LPS
(*Moritella oceanus* 28 and *M. oceanus* 36) and not in the immuno-stimulatory strains.
NCBI accession IDs are provided for the putative protein-coding genes belonging to
each of the 192 putative protein-coding sequence clusters.

| Cluster | Annotated Function | *Moritella oceanus* 28 | *Moritella oceanus* 36 |
|---|---|---|---|
| cluster3861 | prepilin-type N-terminal cleavage/methylation domain-containing protein | HWV02_10765 | HWV03_10370 |
| cluster3862 | hypothetical protein | HWV02_10770 | HWV03_10375 |
| cluster3863 | type II secretion system protein | HWV02_10775 | HWV03_10380 |
| cluster3864 | hypothetical protein | HWV02_10780 | HWV03_10385 |
| cluster3865 | hypothetical protein | HWV02_10785 | HWV03_10390 |
| cluster3866 | PilT/PilU family type 4a pilus ATPase | HWV02_10790 | HWV03_10395 |
| cluster3867 | type II/IV secretion system protein | HWV02_10795 | HWV03_10400 |
| cluster3868 | type II secretion system F family protein | HWV02_10800 | HWV03_10405 |
| cluster3869 | hypothetical protein | HWV02_10805 | HWV03_10410 |
| cluster3870 | type II secretion system protein GspD | HWV02_10810 | HWV03_10415 |
| cluster3871 | sel1 repeat family protein | HWV02_10815 | HWV03_10420 |
| cluster3872 | sterol desaturase family protein | HWV02_10820 | HWV03_10425 |
| cluster3873 | pilin | HWV02_10825 | HWV03_10430 |
| cluster3874 | PhzF family phenazine biosynthesis protein | HWV02_11180 | HWV03_10785 |
| cluster3875 | hypothetical protein | HWV02_11185 | HWV03_10790 |
| cluster3876 | GFA family protein | HWV02_11190 | HWV03_10800 |
| cluster3877 | GNAT family N-acetyltransferase | HWV02_11195 | HWV03_10805 |
| cluster3878 | hypothetical protein | HWV02_11480 | HWV03_11085 |
| cluster3879 | hypothetical protein | HWV02_16395 | HWV03_11150 |
| cluster3880 | M4 family metallopeptidase | HWV02_11565 | HWV03_11190 |
| cluster3881 | hypothetical protein | HWV02_11635 | HWV03_11260 |
| cluster3882 | phosphotyrosine protein phosphatase | HWV02_11880 | HWV03_11485 |
| cluster3883 | ExeM/NucH family extracellular endonuclease | HWV02_12190 | HWV03_11795 |
| cluster3884 | hypothetical protein | HWV02_12265 | HWV03_11830 |
| cluster3885 | RHS repeat-associated core domain-containing protein | HWV02_12270 | HWV03_11835 |
| cluster3890 | copper chaperone PCu(A)C | HWV02_12375 | HWV03_11970 |
| cluster3891 | hypothetical protein | HWV02_12380 | HWV03_11975 |
| cluster3892 | di-heme enzyme | HWV02_12385 | HWV03_11980 |
| cluster3893 | metallo-mystery pair system four-Cys motif protein | HWV02_12390 | HWV03_11985 |
| cluster3894 | hypothetical protein | HWV02_12395 | HWV03_11990 |
| cluster3897 | hypothetical protein | HWV02_07900 | HWV03_12380 |
| cluster3898 | hypothetical protein | HWV02_07895 | HWV03_12385 |
| cluster3901 | glycosyltransferase | HWV02_12905 | HWV03_12540 |
| cluster3902 | hypothetical protein | HWV02_12915 | HWV03_12550 |
| cluster3903 | MBOAT family protein | HWV02_12920 | HWV03_12555 |
| cluster3904 | SGNH/GDSL hydrolase family protein | HWV02_12925 | HWV03_12560 |
| cluster3906 | HIT family protein | HWV02_13220 | HWV03_12855 |
| cluster3907 | type II secretion system protein | HWV02_13385 | HWV03_13060 |
| cluster3908 | hypothetical protein | HWV02_13815 | HWV03_13365 |
| cluster3909 | MBL fold metallo-hydrolase | HWV02_13935 | HWV03_13485 |
| cluster3910 | hypothetical protein | HWV02_13940 | HWV03_13490 |
| cluster3911 | DUF692 domain-containing protein | HWV02_13945 | HWV03_13495 |
| cluster3912 | putative DNA-binding domain-containing protein | HWV02_13950 | HWV03_13500 |
| cluster3913 | DoxX family protein | HWV02_13955 | HWV03_13505 |
| cluster3914 | LysR family transcriptional regulator | HWV02_13975 | HWV03_13525 |
| cluster3918 | YunC family protein | HWV02_14190 | HWV03_13760 |
| cluster3920 | CDP-archaeol synthase | HWV02_14320 | HWV03_13890 |
| cluster3921 | AMP-binding protein | HWV02_14325 | HWV03_13895 |

TABLE 6-continued

Gene clusters unique to the *Moritella* strains containing immuno-silent LPS
(*Moritella oceanus* 28 and *M. oceanus* 36) and not in the immuno-stimulatory strains.
NCBI accession IDs are provided for the putative protein-coding genes belonging to
each of the 192 putative protein-coding sequence clusters.

| Cluster | Annotated Function | *Moritella oceanus* 28 | *Moritella oceanus* 36 |
| --- | --- | --- | --- |
| cluster3922 | hypothetical protein | HWV02_14330 | HWV03_13900 |
| cluster3923 | phosphoenolpyruvate synthase | HWV02_14335 | HWV03_13905 |
| cluster3924 | phosphotransferase | HWV02_14340 | HWV03_13910 |
| cluster3925 | UbiA family prenyltransferase | HWV02_14345 | HWV03_13915 |
| cluster3926 | MMPL family transporter | HWV02_14350 | HWV03_13920 |
| cluster3927 | hypothetical protein | HWV02_14355 | HWV03_13925 |
| cluster3928 | outer membrane lipoprotein-sorting protein | HWV02_14360 | HWV03_13930 |
| cluster3929 | TAXI family TRAP transporter solute-binding subunit | HWV02_14450 | HWV03_14025 |
| cluster3930 | hypothetical protein | HWV02_14580 | HWV03_14150 |
| cluster3931 | hypothetical protein | HWV02_14890 | HWV03_14455 |
| cluster3932 | endonuclease III domain-containing protein | HWV02_14970 | HWV03_14500 |
| cluster3933 | hypothetical protein | HWV02_03900 | HWV03_14505 |
| cluster3934 | hypothetical protein | HWV02_14940 | HWV03_14510 |
| cluster3935 | DUF2195 family protein | HWV02_14945 | HWV03_14515 |
| cluster3938 | hypothetical protein | HWV02_14960 | HWV03_14665 |
| cluster3939 | methyl-accepting chemotaxis protein | HWV02_15065 | HWV03_14710 |
| cluster3940 | AraC family transcriptional regulator | HWV02_15530 | HWV03_15180 |
| cluster3941 | LysE family transporter | HWV02_15535 | HWV03_15185 |
| cluster3942 | hypothetical protein | HWV02_15540 | HWV03_15190 |
| cluster3943 | hypothetical protein | HWV02_15545 | HWV03_15195 |
| cluster3944 | VOC family protein | HWV02_15610 | HWV03_15270 |
| cluster3946 | acyl-CoA synthetase | HWV02_15690 | HWV03_15355 |
| cluster3947 | hypothetical protein | HWV02_15700 | HWV03_15365 |
| cluster3950 | AAA family ATPase | HWV02_08795 | HWV03_16025 |
| cluster3951 | hypothetical protein | HWV02_16510 | HWV03_16125 |
| cluster3952 | sulfatase-like hydrolase/transferase | HWV02_16625 | HWV03_16235 |
| cluster3953 | hypothetical protein | HWV02_18295 | HWV03_16275 |
| cluster3954 | transposase zinc-binding domain-containing protein | HWV02_05620 | HWV03_16315 |
| cluster3955 | methyltransferase domain-containing protein | HWV02_16740 | HWV03_16455 |
| cluster3959 | sphingomyelin phosphodiesterase | HWV02_16905 | HWV03_16630 |
| cluster3960 | hypothetical protein | HWV02_17980 | HWV03_17570 |
| cluster3961 | Do family serine endopeptidase | HWV02_18000 | HWV03_17590 |
| cluster3962 | Hsp20 family protein | HWV02_18005 | HWV03_17595 |
| cluster3963 | EAL domain-containing protein | HWV02_18010 | HWV03_17600 |
| cluster3965 | hypothetical protein | HWV02_18135 | HWV03_17720 |
| cluster3966 | 2,3-diaminopropionate biosynthesis protein SbnB | HWV02_18205 | HWV03_17770 |
| cluster3967 | 2,3-diaminopropionate biosynthesis protein SbnA | HWV02_18210 | HWV03_17775 |
| cluster3968 | hypothetical protein | HWV02_18270 | HWV03_17815 |
| cluster3975 | ABC transporter substrate-binding protein | HWV02_18685 | HWV03_18405 |
| cluster3976 | iron ABC transporter permease | HWV02_18690 | HWV03_18410 |
| cluster3977 | iron ABC transporter permease | HWV02_18695 | HWV03_18415 |
| cluster3978 | ABC transporter ATP-binding protein | HWV02_18700 | HWV03_18420 |
| cluster3979 | hypothetical protein | HWV02_19915 | HWV03_19595 |
| cluster3980 | DeoR/GlpR transcriptional regulator | HWV02_20705 | HWV03_20385 |
| cluster3981 | glycerophosphoryl diester phosphodiesterase | HWV02_20710 | HWV03_20390 |
| cluster3982 | TRAP transporter substrate-binding protein DctP | HWV02_20715 | HWV03_20395 |

TABLE 6-continued

Gene clusters unique to the *Moritella* strains containing immuno-silent LPS
(*Moritella oceanus* 28 and *M. oceanus* 36) and not in the immuno-stimulatory strains.
NCBI accession IDs are provided for the putative protein-coding genes belonging to
each of the 192 putative protein-coding sequence clusters.

| Cluster | Annotated Function | *Moritella oceanus* 28 | *Moritella oceanus* 36 |
|---|---|---|---|
| cluster3983 | TRAP transporter small permease | HWV02_20720 | HWV03_20400 |
| cluster3984 | TRAP transporter large permease | HWV02_20725 | HWV03_20405 |
| cluster3986 | hypothetical protein | HWV02_22190 | HWV03_21820 |
| cluster3987 | ABC transporter ATP-binding protein | HWV02_03005 | HWV03_03040 |
| cluster3991 | anion permease | HWV02_03250 | HWV03_03215 |
| cluster3992 | adenylyl-sulfate kinase | HWV02_03260 | HWV03_03225 |
| cluster3993 | DHH family phosphoesterase | HWV02_03270 | HWV03_03235 |
| cluster3994 | hypothetical protein | HWV02_03275 | HWV03_03240 |
| cluster3995 | acyltransferase | HWV02_03285 | HWV03_03260 |
| cluster3996 | AAC(3) family N-acetyltransferase | HWV02_03295 | HWV03_03270 |
| cluster3997 | DUF4910 domain-containing protein | HWV02_03300 | HWV03_03275 |
| cluster3998 | GNAT family N-acetyltransferase | HWV02_03305 | HWV03_03280 |
| cluster3999 | HDOD domain-containing protein | HWV02_00405 | HWV03_00365 |
| cluster4000 | FAD-dependent monooxygenase | HWV02_03555 | HWV03_03535 |
| cluster4001 | PaaI family thioesterase | HWV02_03595 | HWV03_03560 |
| cluster4002 | fatty acid desaturase | HWV02_03600 | HWV03_03565 |
| cluster4003 | hypothetical protein | HWV02_03905 | HWV03_03875 |
| cluster63 | hypothetical protein | HWV02_09820;HWV02_09825; HWV02_09830 | HWV03_09540;HWV03_09545 |

TABLE 7

Gene clusters unique to the *Moritella* strains containing immuno-stimulatory LPS
(*Moritella oceanus* 5 and *M. rawaki* 24) and not in the immuno-silent strains.
NCBI accession IDs are provided for the putative protein-coding genes belonging
to each of the 55 putative protein-coding sequence clusters.

| Cluster | Annotated Function | *Moritella oceanus* 5 | *Moritella rawaki* 24 |
|---|---|---|---|
| cluster3085 | WYL domain-containing protein | HWV01_02095 | HWV00_01855;HWV00_18630 |
| cluster4007 | hypothetical protein | HWV01_16210 | HWV00_06000 |
| cluster4008 | YjiH family protein | HWV01_15525 | HWV00_06390 |
| cluster4009 | hypothetical protein | HWV01_15520 | HWV00_06395 |
| cluster4010 | M20 family metallopeptidase | HWV01_15515 | HWV00_06400 |
| cluster4012 | glycosyltransferase family 4 protein | HWV01_12440 | HWV00_06805 |
| cluster4013 | UDP-N-acetylglucosamine 4,6-dehydratase | HWV01_03210 | HWV00_06815 |
| cluster4015 | MAPEG family protein | HWV01_09075 | HWV00_06910 |
| cluster4016 | SAM-dependent methyltransferase | HWV01_14795 | HWV00_07255 |
| cluster4017 | MFS transporter | HWV01_14690 | HWV00_07350 |
| cluster4018 | NTP transferase domain-containing protein | HWV01_03215 | HWV00_07705 |
| cluster4019 | hemerythrin domain-containing protein | HWV01_14185 | HWV00_07830 |
| cluster4020 | DUF2249 domain-containing protein | HWV01_14180 | HWV00_07835 |
| cluster4021 | hypothetical protein | HWV01_14175 | HWV00_07840 |
| cluster4022 | virulence protein | HWV01_14160 | HWV00_07860 |
| cluster4023 | DUF4056 domain-containing protein | HWV01_14155 | HWV00_07865 |
| cluster4024 | BamA/TamA family outer membrane protein | HWV01_14150 | HWV00_07870 |

TABLE 7-continued

Gene clusters unique to the *Moritella* strains containing immuno-stimulatory LPS
(*Moritella oceanus* 5 and *M. rawaki* 24) and not in the immuno-silent strains.
NCBI accession IDs are provided for the putative protein-coding genes belonging
to each of the 55 putative protein-coding sequence clusters.

| Cluster | Annotated Function | *Moritella oceanus* 5 | *Moritella rawaki* 24 |
| --- | --- | --- | --- |
| cluster4025 | LysR family transcriptional regulator | HWV01_07865 | HWV00_07965 |
| cluster4026 | class I SAM-dependent methyltransferase | HWV01_13705 | HWV00_07970 |
| cluster4027 | type I-F CRISPR-associated protein Csy3 | HWV01_12965 | HWV00_08015 |
| cluster4028 | glyoxalase/bleomycin resistance/dioxygenase family protein | HWV01_13710 | HWV00_08400 |
| cluster4029 | hypothetical protein | HWV01_13650 | HWV00_08505 |
| cluster4031 | peptidase T | HWV01_12710 | HWV00_09050 |
| cluster4033 | EAL domain-containing protein | HWV01_11380 | HWV00_09880 |
| cluster4034 | SDR family NAD(P)-dependent oxidoreductase | HWV01_11330 | HWV00_09945 |
| cluster4035 | GtrA family protein | HWV01_10610 | HWV00_10465 |
| cluster4036 | HAMP domain-containing histidine kinase | HWV01_10605 | HWV00_10470 |
| cluster4037 | response regulator transcription factor | HWV01_10600 | HWV00_10475 |
| cluster4038 | glycosyltransferase family 2 protein | HWV01_10595 | HWV00_10480 |
| cluster4039 | glycosyltransferase family 39 protein | HWV01_10590 | HWV00_10485 |
| cluster4040 | sodium:solute symporter family protein | HWV01_09605 | HWV00_11480 |
| cluster4042 | NAD(P)H-dependent oxidoreductase | HWV01_09210 | HWV00_12085 |
| cluster4043 | DUF2007 domain-containing protein | HWV01_08965 | HWV00_12310 |
| cluster4044 | hypothetical protein | HWV01_04185 | HWV00_12545 |
| cluster4045 | sensor domain-containing diguanylate cyclase | HWV01_08355 | HWV00_12595 |
| cluster4046 | TMAO reductase system sensor histidine kinase/response regulator TorS | HWV01_07905 | HWV00_12890 |
| cluster4047 | TMAO reductase system periplasmic protein TorT | HWV01_07900 | HWV00_12895 |
| cluster4048 | two-component system response regulator TorR | HWV01_07895 | HWV00_12900 |
| cluster4049 | hypothetical protein | HWV01_07060 | HWV00_13445 |
| cluster4050 | serine dehydratase subunit alpha family protein | HWV01_07000 | HWV00_13600 |
| cluster4053 | hypothetical protein | HWV01_04905 | HWV00_15730 |
| cluster4055 | hypothetical protein | HWV01_02100 | HWV00_01860 |
| cluster4056 | hypothetical protein | HWV01_02085 | HWV00_01865 |
| cluster4059 | GDP-mannose 4,6-dehydratase | HWV01_03220 | HWV00_17530 |
| cluster4060 | threonine/serine exporter family protein | HWV01_02935 | HWV00_17855 |
| cluster4061 | threonine/serine exporter family protein | HWV01_02930 | HWV00_17860 |
| cluster4062 | DNA-directed DNA polymerase | HWV01_02115 | HWV00_18600 |
| cluster4063 | hypothetical protein | HWV01_02105 | HWV00_18625 |
| cluster4064 | hypothetical protein | HWV01_02080 | HWV00_18645 |
| cluster4065 | hypothetical protein | HWV01_15910 | HWV00_20815 |
| cluster4069 | winged helix-turn-helix domain-containing protein | HWV01_18145 | HWV00_04160 |
| cluster4072 | cache domain-containing protein | HWV01_17660 | HWV00_04540 |
| cluster4073 | zinc-dependent alcohol dehydrogenase family protein | HWV01_17410 | HWV00_04610 |
| cluster4075 | hypothetical protein | HWV01_17675 | HWV00_04690 |
| cluster4077 | hypothetical protein | HWV01_16800 | HWV00_05335 |

The biosynthesis of lipid A is highly conserved and consists of nine different enzymes [49]. The inventors identified the lipid A biosynthesis enzymes and their protein coding sequences within the genomes of four *Moritella* strains (FIG. 7). The inventors identified one copy of each enzyme, with the exception of LpxL, the late acyltransferase for laurate (C12:0), which had two protein coding sequences present in each genome. Next, the degree of sequence conservation was determined for enzymes in the lipid A biosynthesis pathway between these four *Moritella* strains and *E. coli* (FIG. 61D). While the *E. coli* lipid A enzymes were distinct from those present in any *Moritella* strain, the most notable distinctions came from comparisons within *Moritella*. The enzymes that build lipid A in immuno-silent *M. oceanus* 28 and *M. oceanus* 36 are (on a network scale) highly similar to each other. The analogous enzymes in immuno-stimulatory *M. oceanus* 5 or *M. rawaki* 24 are also highly similar to each other, but differed from the corresponding enzymes present in immuno-silent *M. oceanus* strains. Based on this analysis, these data indicate that no single enzyme is responsible for differential inflammatory activities of deep-sea *Moritella* LPS. Rather, the entire lipid A biosynthetic pathway can contribute to the distinct inflammatory activities of select deep-sea *Moritella* LPS structures.

In this study, the limits of the pattern recognition hypothesis was tested by asking if mammalian PRRs could detect bacteria from a different ecosystem. Two major conclusions were drawn. First, some deep-sea bacteria can be detected by mammalian LPS receptors, although immuno-stimulation of both CD14 and TLR4 represented a minor population of all bacteria examined (18% (9/50)). Nonetheless, the identification of even a single bacterium with immuno-stimulatory activity validates a central principle of Pattern Recognition—that the human innate immune system can detect novel bacteria. Secondly, it was found that mammalian PRRs were unable to detect the majority (82% (41/50)) of LPS displayed on live, cultured bacterial strains from the deep sea, revealing that the rules of innate immune detection may be more limited than previously appreciated. Thus, the inventors posit a revision to the pattern recognition concept-PRRs should have the capacity to detect all bacteria that exist in the same general habitat as the host. In other words, innate immunity follows local (not global) rules of engagement (FIG. 8).

The mechanisms of immuno-silence associated with deep-sea bacteria were diverse. Some bacteria contained silent LPS only when in the context of whole bacterial cells, whereas others contained LPS that contained modifications known to be immune-evasive (e.g. hepta-acylation). The most striking mechanistic finding however, was the discovery that all forty-four strains of *Moritella* examined displayed lipid A structures that are likely hexa-acylated and bis-phosphorylated. Despite this consistency in acyl chain number and phosphorylation status, the inventors detected higher amounts of C16 acyl chains on lipid A from immuno-silent *Moritella*, as compared to their immuno-stimulatory counterparts.

Deep-sea environments, including the PIPA deep sea, remain largely unexplored [59]. As the diversity of life in these regions is only beginning to undergo taxonomic determination [60], it is not surprising that all four of the bacterial strains sequenced contained unique genomes and displayed unique biological activities, attributes that are consistent with the assignment of these strains as unique species [61, 62]. These findings highlight the value of further microbial exploration in undocumented habitats, including remote marine protected areas that have limited anthropogenic disturbance.

It is unlikely that deep-sea bacteria experience any fitness benefit from evading detection of mammalian PRRs, even those expressed by mammals that occasionally dive to the depths that these microbes inhabit (Table 1). Indeed, even the historically most-abundant deep-diving marine mammal in the region (the now relatively rare sperm whale, *Physeter macrocephalus* [63] though capable of diving to 2250 m depth [18], is not capable of spending extensive time there. As such, there would be minimal opportunity for marine mammals to interact meaningfully with deep-sea microbial communities, which are distinctly different from shallow-water communities (FIGS. 1B, 1C). Inhabiting an environment devoid (or nearly devoid) of mammals likely creates a scenario where there is no selective advantage to bacterial LPS being immune-evasive, immuno-silent, or immuno-stimulatory. Bacteria from extreme, non-mammalian environments may have cell wall structures that are uniquely optimized to their environment, and when habitats are artificially crossed, bacteria may encounter a mammalian host in which they are accidentally immune-evasive. The consequences of such interactions are difficult to predict, but are important to consider in this age of increasing globalization and exploitation of deep-sea resources [64].

Finally, it is worth considering whether deep-sea invertebrates may have evolved PRRs to detect LPS structures that are common to bacteria found in these habitats. This consideration is notable, as the functions of LPS receptors have been explored almost exclusively in mammals. In fact, genomic analysis of numerous organisms has demonstrated a notable lack of the CD14-MD-2-TLR4 system in marine fish and invertebrates. While proteins that display homology to TLR4 can sometimes be identified in fish or invertebrates, the significance of this homology in unclear, as CD14 and MD-2 can almost be considered mammal-specific factors. Identification of invertebrate taxa in the deep-sea is ongoing, and many species are yet unknown, however deep-sea corals and sponges are among the most abundant foundational macrofauna [59, 60]. Shallow-water cnidarians have an abundance of genes that have been bioinformatically annotated as PRRs [65]; however, whether these PRRs also exist abundantly in deep-sea taxa is unknown. Only one study has examined flagellin signaling in cnidarians (a shallow-water anemone) [66], but nothing is yet known about LPS detection events in any marine invertebrate. As such, it is unclear whether LPS detection systems are common outside of the mammalian lineage. Indeed, even the plant *Arabidopsis thaliana*, which was once thought to use the protein LORE as an LPS receptor [67], is now recognized to not detect LPS at all [68]. While these evolution-function considerations remain to be answered, the data described herein suggest that the rules of innate immune engagement are defined locally (not globally), and thus provide a mandate for further exploration of host-microbe interactions in diverse ecosystems.

REFERENCES

Janeway C A, Jr.: Approaching the asymptote? Evolution and revolution in immunology. *Cold Spring Harbor symposia on quantitative biology* 1989, 54 Pt 1:1-13.

Medzhitov R, Janeway C A: Innate immunity: impact on the adaptive immune response. *Current Opinion in Immunology* 1997, 9(1):4-9.

Janeway C A, Jr., Medzhitov R: Innate immune recognition. *Annual review of immunology* 2002, 20:197-216.

Akira S, Uematsu S, Takeuchi O: Pathogen Recognition and Innate Immunity. *Cell* 2006, 124(4):783-801.

Kieser K J, Kagan J C: Multi-receptor detection of individual bacterial products by the innate immune system. *Nat Rev Immunol* 2017, 17(6):376-390.

Roers A, Hiller B, Hornung V: Recognition of Endogenous Nucleic Acids by the Innate Immune System. *Immunity* 2016, 44(4):739-754.

Vance R E, Isberg R R, Portnoy D A: Patterns of pathogenesis: discrimination of pathogenic and nonpathogenic microbes by the innate immune system. *Cell host & microbe* 2009, 6(1):10-21.

Steimle A, Autenrieth I B, Frick J-S: Structure and function: Lipid A modifications in commensals and pathogens. *International Journal of Medical Microbiology* 2016, 306(5):290-301.

Andersen-Nissen E, Smith K D, Strobe K L, Barrett S L R, Cookson B T, Logan S M, Aderem A: Evasion of Toll-like receptor 5 by flagellated bacteria. *Proceedings of the National Academy of Sciences of the United States of America* 2005, 102(26):92479252.

Li Y, Wang Z, Chen J, Ernst R K, Wang X: Influence of lipid A acylation pattern on membrane permeability and innate immune stimulation. *Marine drugs* 2013, 11(9):3197-3208.

Da Silva G J, Domingues S: Interplay between Colistin Resistance, Virulence and Fitness in *Acinetobacter baumannii*. *Antibiotics (Basel, Switzerland)* 2017, 6(4).

Beceiro A, Tomis M, Bou G: Antimicrobial Resistance and Virulence: a Successful or Deleterious Association in the Bacterial World? *Clinical Microbiology Reviews* 2013, 26(2):185-230.

Khan M M, Ernst O, Sun J, Fraser I D C, Ernst R K, Goodlett D R, Nita-Lazar A: Mass Spectrometry-based Structural Analysis and Systems Immunoproteomics Strategies for Deciphering the Host Response to Endotoxin. *Journal of molecular biology* 2018, 430(17):2641-2660.

Kokoulin M S, Sokolova E V, Elkin Y N, Romanenko L A, Mikhailov V V, Komandrova N A: Partial structure and immunological properties of lipopolysaccharide from marine-derived *Pseudomonas stutzeri* KMM 226. *Antonie van Leeuwenhoek* 2017, 110(12):1569-1580.

Lorenzo F D, Palmigiano A, Paciello I, Pallach M, Garozzo D, Bernardini M L, Cono V, Yakimov M M, Molinaro A, Silipo A: The Deep-Sea Polyextremophile *Halobacteroides lacunaris* TB21 Rough-Type LPS: Structure and Inhibitory Activity towards Toxic LPS. *Marine drugs* 2017, 15(7).

Lorenzo F D, Palmigiano A, Albitar-Nehme S, Pallach M, Kokoulin M, Komandrova N, Romanenko L, Bernardini M L, Garozzo D, Molinaro A et al: Lipid A Structure and Immunoinhibitory Effect of the Marine Bacterium *Cobetia pacifica* KMM 3879T. *European Journal of Organic Chemistry* 2018, 2018(20-21):2707-2716.

Scott A J, Oyler B L, Goodlett D R, Ernst R K: Lipid A structural modifications in extreme conditions and identification of unique modifying enzymes to define the Toll-like receptor 4 structure-activity relationship. *Biochimica et biophysica acta Molecular and cell biology of lipids* 2017, 1862(11):1439-1450.

Perrin W F, Wursig B, Thewissen J G M: Encyclopedia of marine mammals., vol. 2. Amsterdam, The Netherlands: Elsevier Inc.; 2009.

Rotjan R, Jamieson R, Carr B, Kaufman L, Mangubhai S, Obura D, Pierce R, Rimon B, Ris B, Sandin S et al: Establishment, management, and maintenance of the phoenix islands protected area. *Advances in marine biology* 2014, 69:289-324.

D'Amico S, Collins T, Marx J-C, Feller G, Gerday C: Psychrophilic microorganisms: challenges for life. *EMBO Rep* 2006, 7(4):385-389.

Zanoni I, Ostuni R, Marek L R, Barresi S, Barbalat R, Barton G M, Granucci F, Kagan J C: CD14 controls the LPS-induced endocytosis of Toll-like receptor 4. *Cell* 2011, 147(4):868-880.

Tan Y, Zanoni I, Cullen T W, Goodman A L, Kagan J C: Mechanisms of Toll-like Receptor 4 Endocytosis Reveal a Common Immune-Evasion Strategy Used by Pathogenic and Commensal Bacteria. *Immunity* 2015, 43(5): 909-922.

Akashi S, Saitoh S, Wakabayashi Y, Kikuchi T, Takamura N, Nagai Y, Kusumoto Y, Fukase K, Kusumoto S, Adachi Y et al: Lipopolysaccharide interaction with cell surface Toll-like receptor 4-MD-2: higher affinity than that with MD-2 or CD14. *The Journal of experimental medicine* 2003, 198(7):1035-1042.

Poltorak A, He X, Smirnova I, Liu M Y, Van Huffel C, Du X, Birdwell D, Alejos E, Silva M, Galanos C et al: Defective LPS signaling in C3H/HeJ and C57BL/10ScCr mice: mutations in Tlr4 gene. *Science (New York, NY)* 1998, 282(5396):2085-2088.

Kayagaki N, Stowe I B, Lee B L, O'Rourke K, Anderson K, Warming S, Cuellar T, Haley B, Roose-Girma M, Phung Q T et al: Caspase-11 cleaves gasdermin D for non-canonical inflammasome signalling. *Nature* 2015, 526 (7575):666-671.

Kayagaki N, Warming S, Lamkanfi M, Walle L V, Louie S, Dong J, Newton K, Qu Y, Liu J, Heldens S et al: Non-canonical inflammasome activation targets caspase-11. *Nature* 2011, 479(7371):117-121.

Shi J, Zhao Y, Wang K, Shi X, Wang Y, Huang H, Zhuang Y, Cai T, Wang F, Shao F: Cleavage of GSDMD by inflammatory caspases determines pyroptotic cell death. *Nature* 2015, 526(7575):660-665.

Shi J, Zhao Y, Wang Y, Gao W, Ding J, Li P, Hu L, Shao F: Inflammatory caspases are innate immune receptors for intracellular LPS. *Nature* 2014, 514(7521):187-192.

Rayamajhi M, Zhang Y, Miao E A: Detection of pyroptosis by measuring released lactate dehydrogenase activity. *Methods Mol Biol* 2013, 1040:85-90.

Shi J, Gao W, Shao F: Pyroptosis: Gasdermin-Mediated Programmed Necrotic Cell Death. *Trends in Biochemical Sciences* 2017, 42(4):245-254.

Zanoni I, Tan Y, Di Gioia M, Broggi A, Ruan J, Shi J, Donado C A, Shao F, Wu H, Springstead J R et al: An endogenous caspase-11 ligand elicits interleukin-1 release from living dendritic cells. *Science (New York, NY)* 2016, 352(6290):1232-1236.

Zanoni I, Tan Y, Di Gioia M, Springstead J R, Kagan J C: By Capturing Inflammatory Lipids Released from Dying Cells, the Receptor CD14 Induces Inflammasome-Dependent Phagocyte Hyperactivation. *Immunity* 2017, 47(4): 697-709.e693.

Levin J: The horseshoe crab: a model for gram-negative sepsis in marine organisms and humans. *Prog Clin Biol Res* 1988, 272:3-15.

Levin J, Bang F B: Clottable protein in *Limulus*; its localization and kinetics of its coagulation by endotoxin. *Thrombosis et diathesis haemorrhagica* 1968, 19(1): 186197.

Muta T, Miyata T, Misumi Y, Tokunaga F, Nakamura T, Toh Y, Ikehara Y, Iwanaga S: *Limulus* factor C. An endotoxinsensitive serine protease zymogen with a mosaic structure of complement-like, epidermal growth factor-like, and lectin-like domains. *The Journal of biological chemistry* 1991, 266(10):6554-6561.

Smith D R, Brockmann H J, Beekey M A, King T L, Millard M J, Zaldivar-Rae J: Conservation status of the American horseshoe crab, (*Limulus polyphemus*): a regional assessment. *Reviews in Fish Biology and Fisheries* 2017, 27(1):135-175.

Raetz C R, Whitfield C: Lipopolysaccharide endotoxins. *Annual review of biochemistry* 2002, 71:635-700.

Lerouge I, Vanderleyden J: O-antigen structural variation: mechanisms and possible roles in animal/plant-microbe interactions. *FEMS Microbiology Reviews* 2002, 26(1):17-47.

Matsuura M: Structural Modifications of Bacterial Lipopolysaccharide that Facilitate Gram-Negative Bacteria Evasion of Host Innate Immunity. *Front Immunol* 2013, 4:109-109.

Chandler C E, Ernst R K: Bacterial lipids: powerful modifiers of the innate immune response. *F1000Research* 2017, 6.

Salkowski C A, Detore G R, Vogel S N: Lipopolysaccharide and monophosphoryl lipid A differentially regulate interleukin-12, gamma interferon, and interleukin-10 mRNA production in murine macrophages. *Infection and immunity* 1997, 65(8):32393247.

Kawasaki K, Ernst R K, Miller S I: Inhibition of *Salmonella enterica* Serovar *Typhimurium* Lipopolysaccharide Deacylation by Aminoarabinose Membrane *Modification*. *Journal of bacteriology* 2005, 187(7):2448-2457.

Pelletier M R, Casella L G, Jones J W, Adams M D, Zurawski D V, Hazlett K R O, Doi Y, Ernst R K: Unique structural modifications are present in the lipopolysaccharide from colistin-resistant strains of *Acinetobacter baumannii*. *Antimicrob Agents Chemother* 2013, 57(10):4831-4840.

Liu Y-Y, Chandler C E, Leung L M, McElheny C L, Mettus R T, Shanks R M Q, Liu J-H, Goodlett D R, Ernst R K, Doi Y: Structural Modification of Lipopolysaccharide Conferred by mcr-1 in Gram-Negative ESKAPE Pathogens. *Antimicrob Agents Chemother* 2017, 61(6):e00580-00517.

Pizzuto M, Lonez C, Baroja-Mazo A, Martinez-Banaclocha H, Tourlomousis P, Gangloff M, Pelegrin P, Ruysschaert J-M, Gay N J, Bryant C E: Saturation of acyl chains converts cardiolipin from an antagonist to an activator of Toll-like receptor-4. *Cell Mol Life Sci* 2019, 76(18):3667-3678.

Lopalco P, Stahl J, Annese C, Averhoff B, Corcelli A: Identification of unique cardiolipin and monolysocardiolipin species in *Acinetobacter baumannii*. *Scientific Reports* 2017, 7(1):2972.

Therisod H, Labas V, Caroff M: Direct microextraction and analysis of rough-type lipopolysaccharides by combined thin-layer chromatography and MALDI mass spectrometry. *Analytical chemistry* 2001, 73(16):3804-3807.

Scott A J, Flinders B, Cappell J, Liang T, Pelc R S, Tran B, Kilgour D P A, Heeren R M A, Goodlett D R, Ernst R K: Norharmane matrix enhances detection of endotoxin by MALDI-MS for simultaneous profiling of pathogen, host and vector systems. *Pathogens and Disease* 2016, 74(8).

Caroff M, Karibian D, Cavaillon J M, Haeffner-Cavaillon N: Structural and functional analyses of bacterial lipopolysaccharides. *Microbes and infection* 2002, 4(9):915926.

Gregg K A, Harberts E, Gardner F M, Pelletier M R, Cayatte C, Yu L, McCarthy M P, Marshall J D, Ernst R K: Rationally Designed TLR4 Ligands for Vaccine Adjuvant Discovery. *mBio* 2017, 8(3).

Sorensen M C C, Gardner F G, Ramadan S, Khot P D, Leung L M, Farrance, C E, Goodlett D R, Ernst R K, Nilsson E.: Rapid microbial identification and colistin resistance detection via MALDI-TOF M S using a novel on-target extraction of membrane lipids. *Scientific Reports* Accepted for publication Nov. 22, 2020.

Hittle L E, Powell D A, Jones J W, Tofigh M, Goodlett D R, Moskowitz S M, Ernst R K: Site-specific activity of the acyltransferases HtrB1 and HtrB2 in *Pseudomonas aeruginosa* lipid A biosynthesis. *Pathogens and disease* 2015, 73(8):ftv053-ftv053.

Guillotte M L, Gillespie J J, Chandler C E, Rahman M S, Ernst R K, Azad A F: *Rickettsia* Lipid A Biosynthesis Utilizes the Late Acyltransferase LpxJ for Secondary Fatty Acid Addition. *Journal of bacteriology* 2018, 200(19):e00334-00318.

Rietschel E T, Kirikae T, Schade F U, Mamat U, Schmidt G, Loppnow H, Ulmer A J, Zahringer U, Seydel U, Di Padova F et al: Bacterial endotoxin: molecular relationships of structure to activity and function. *FASEB journal: official publication of the Federation of American Societies for Experimental Biology* 1994, 8(2):217-225.

Park B S, Lee J-O: Recognition of lipopolysaccharide pattern by TLR4 complexes. *Exp Mol Med* 2013, 45(12):e66-e66.

Facchini F A, Zaffaroni L, Minotti A, Rapisarda S, Calabrese V, Forcella M, Fusi P, Airoldi C, Ciaramelli C, Billod J-M et al: Structure-Activity Relationship in Monosaccharide-Based Toll-Like Receptor 4 (TLR4) Antagonists. *Journal of Medicinal Chemistry* 2018, 61(7):2895-2909.

Ciufo S, Kannan S, Sharma S, Badretdin A, Clark K, Turner S, Brover S, Schoch C L, Kimchi A, DiCuccio M: Using average nucleotide identity to improve taxonomic assignments in prokaryotic genomes at the NCBI. *International journal of systematic and evolutionary microbiology* 2018, 68(7):2386-2392.

Jain C, Rodriguez-R L M, Phillippy A M, Konstantinidis K T, Aluru S: High throughput ANI analysis of 90K prokaryotic genomes reveals clear species boundaries. *Nature communications* 2018, 9(1):5114.

Kennedy BRC, K. Cantwell, M. Malik, C. Kelley, J. Potter, K. Elliot, M. Lobecker, D. Sowers, M. White, S. France et al: The unknown and the unexplored: Quantifying what we now know, and still don't know, about the Pacific deep-sea following the 3-year NOAA CAPSTONE Expeditions. *In review, Frontiers in Marine Science* 2019.

Auscavitch S R, Deere M C, Keller A G, Rotjan R D, Shank T M, Cordes E E: Oceanographic Drivers of Deep-Sea Coral Species Distribution and Community Assembly on Seamounts, Islands, Atolls, and Reefs Within the Phoenix Islands Protected Area. *Frontiers in Marine Science* 2020, 7(42).

International Code of Nomenclature of Prokaryotes. *International journal of systematic and evolutionary microbiology* 2019, 69(1A):S1-S111.

Imachi H, Nobu M K, Nakahara N, Morono Y, Ogawara M, Takaki Y, Takano Y, Uematsu K, Ikuta T, Ito M et al: Isolation of an archaeon at the prokaryote-eukaryote interface. *Nature* 2020, 577(7791):519-525.

Kennedy B R C, Hakam L, Jamieson R, Witting J, Taei S, Smith T, Teemari T, Rotjan R D: Historical trends of sperm whale (*Physeter macrocephalus*) distribution in the Phoenix Archipelago. *bioRxiv; In preparation for submission to Frontiers of Marine Science* 2020.

Cordes E E, Levin L A: Exploration before exploitation. *Science (New York, NY)* 2018, 359(6377):719.

Hamada M, Shoguchi E, Shinzato C, Kawashima T, Miller D J, Satoh N: The complex NOD-like receptor repertoire of the coral *Acropora digitifera* includes novel domain combinations. *Molecular biology and evolution* 2013, 30(1):167-176.

Brennan J J, Messerschmidt J L, Williams L M, Matthews B J, Reynoso M, Gilmore T D: Sea anemone model has a single Toll-like receptor that can function in pathogen detection, NF-KB signal transduction, and development. *Proceedings of the National Academy of Sciences of the United States of America* 2017, 114(47):E10122-e10131.

Ranf S, Gisch N, Schaffer M, Illig T, Westphal L, Knirel Y A, Sinchez-Carballo P M, Zahringer U, Hückelhoven R, Lee J et al: A lectin S-domain receptor kinase mediates lipopolysaccharide sensing in *Arabidopsis thaliana*. *Nature immunology* 2015, 16(4):426-433.

Kutschera A, Dawid C, Gisch N, Schmid C, Raasch L, Gerster T, Schaffer M, Smakowska-Luzan E, Belkhadir Y, Vlot A C et al: Bacterial medium-chain 3-hydroxy fatty acid metabolites trigger immunity in *Arabidopsis* plants. *Science (New York, NY)* 2019, 364(6436):178-181.

Amon D J, Kennedy B R C, Cantwell K, Suhre K, Glickson D, Shank T M, Rotjan R D: Deep-Sea Debris in the Central and Western Pacific Ocean. *Frontiers in Marine Science* 2020, 7(369).

Bolyen E, Rideout J R, Dillon M R, Bokulich N A, Abnet C C, Al-Ghalith G A, Alexander H, Alm E J, Arumugam M, Asnicar F et al: Reproducible, interactive, scalable and extensible microbiome data science using QIIME 2. *Nature Biotechnology* 2019, 37(8):852-857.

Callahan B J, McMurdie P J, Rosen M J, Han A W, Johnson A J A, Holmes S P: DADA2: High-resolution sample inference from Illumina amplicon data. *Nature Methods* 2016, 13(7):581-583.

Quast C, Pruesse E, Yilmaz P, Gerken J, Schweer T, Yarza P, Peplies J, Glöckner F O: The SILVA ribosomal RNA gene database project: improved data processing and web-based tools. *Nucleic acids research* 2013, 41(Database issue):D590-D596.

McMurdie P J, Holmes S: phyloseq: An R Package for Reproducible Interactive Analysis and Graphics of Microbiome Census Data. *PloS one* 2013, 8(4):e61217.

Wickham H: ggplot2: Elegant Graphics for Data Analysis: Springer-Verlag New York; 2016.

Team R C: R: A language and environment for statistical computing. Vienna, Austria: Foundation for Statistical Computing; 2020.

Rudi K, Skulberg O M, Larsen F, Jakobsen K S: Strain characterization and classification of oxyphotobacteria in clone cultures on the basis of 16S rRNA sequences from the variable regions V6, V7, and V8. *Appl Environ Microbiol* 1997, 63(7):2593-2599.

Wick R R, Judd L M, Gorrie C L, Holt K E: Unicycler: Resolving bacterial genome assemblies from short and long sequencing reads. *PLOS Computational Biology* 2017, 13(6):e1005595.

Parks D H, Imelfort M, Skennerton C T, Hugenholtz P, Tyson G W: CheckM: assessing the quality of microbial genomes recovered from isolates, single cells, and metagenomes. *Genome research* 2015, 25(7):1043-1055.

Parks D H, Chuvochina M, Waite D W, Rinke C, Skarshewski A, Chaumeil P-A, Hugenholtz P: A standardized bacterial taxonomy based on genome phylogeny substantially revises the tree of life. *Nature Biotechnology* 2018, 36(10):996-1004.

Chaumeil P A, Mussig A J, Hugenholtz P, Parks D H: GTDB-Tk: a toolkit to classify genomes with the Genome Taxonomy Database. *Bioinformatics (Oxford, England)* 2019.

Stamatakis A: RAxML Version 8: A Tool for Phylogenetic Analysis and Post-Analysis of Large Phylogenies. *Bioinformatics (Oxford, England)* 2014, 30.

Letunic I, Bork P: Interactive Tree Of Life (iTOL) v4: recent updates and new developments. *Nucleic acids research* 2019, 47(W1):W256-w259.

Li L, Stoeckert C J, Jr., Roos D S: OrthoMCL: identification of ortholog groups for eukaryotic genomes. *Genome research* 2003, 13(9):2178-2189.

Arkin A P, Cottingham R W, Henry C S, Harris N L, Stevens R L, Maslov S, Dehal P, Ware D, Perez F, Canon S et al: KBase: The United States Department of Energy Systems Biology Knowledgebase. *Nature Biotechnology* 2018, 36(7):566-569.

Katoh K, Standley D M: MAFFT multiple sequence alignment software version 7: improvements in performance and usability. *Molecular biology and evolution* 2013, 30(4):772-780.

Cock P J, Antao T, Chang J T, Chapman B A, Cox C J, Dalke A, Friedberg I, Hamelryck T, Kauff F, Wilczynski B et al: Biopython: freely available Python tools for computational molecular biology and bioinformatics. *Bioinformatics (Oxford, England)* 2009, 25(11):1422-1423.

Apicella M A: Isolation and characterization of lipopolysaccharides. *Methods Mol Biol* 2008, 431:3-13.

Hirschfeld M, Ma Y, Weis J H, Vogel S N, Weis J J: Cutting edge: repurification of lipopolysaccharide eliminates signaling through both human and murine toll-like receptor 2. *Journal of immunology (Baltimore, Md: 1950)* 2000, 165(2):618-622.

El Hamidi A, Tirsoaga A, Novikov A, Hussein A, Caroff M: Microextraction of bacterial lipid A: easy and rapid method for mass spectrometric characterization. *J Lipid Res* 2005, 46(8):1773-1778.

Leung L M, Fondrie W E, Doi Y, Johnson J K, Strickland D K, Ernst R K, Goodlett D R: Identification of the ESKAPE pathogens by mass spectrometric analysis of microbial membrane glycolipids. *Scientific Reports* 2017, 7(1):6403.

Li Y, Powell D A, Shaffer S A, Rasko D A, Pelletier M R, Leszyk J D, Scott A J, Masoudi A, Goodlett D R, Wang X et al: LPS remodeling is an evolved survival strategy for bacteria. *Proceedings of the National Academy of Sciences of the United States of America* 2012, 109(22):8716-8721.

Obura D, Stone G, Mangubhai S, Bailey S, Yoshinaga A, Holloway C, Barrel R:
Baseline Marine Biological Surveys of the Phoenix Islands, July 2000. In., vol. 589; 2011.

Kerr V, Wragg G: Southern Line Islands—Observations and Marine Survey Report 2008; 2008.

Kerr V, Wragg G: Phoenix Islands Conservation Survey 2006 Marine Survey Report; 2006.

Example 2: Materials & Methods

Deep-sea sampling: In October 2017, the R/V Falkor, operated by the Schmidt Ocean Institute, conducted 17 remotely operated vehicle (ROV) surveys in the Phoenix Islands Protected Area (cruise FK171005) (detailed in [60]) using the 4,500-m rated ROV SuBastian. On the PIPA expedition, ROV SuBastian was equipped with an Insite Pacific Mini Zeus HD 1080i CMOS camera for situational awareness and an Insite Zeus Plus or SULIS 4K 12× Zoom camera for science surveys (5.1-51 mm wide angle zoom lens). In addition, the vehicle hosted a Seabird FastCAT CTD Sensor (SBE49) and a Paroscientific 8000 Series Submersible Depth Sensor for measuring depth of observations (as in [69]). In addition to 17 ROV dives, 7 CTD casts were deployed and retrieved in PIPA, from which water was filtered for microbial extraction or culturing, as below.

Isolation of culturable bacteria strains: At five atolls within the boundaries of PIPA (depths 270-2500 m), seawater, soft coral tissue, glass sponge tissue, and sea star gut content were collected to use as substrate to grow deep-sea bacteria. Tissue and gut content were homogenized in 5 mL of PBS pH 7.4 in sterile 15 mL falcon tubes. 200 µl of substrate was loaded onto individual Difco™ marine agar 2216 (Becton Dickenson, 212185) plates without antibiotics in a sterile fume hood aboard the R/V Falkor. Plates were incubated at 4° C. for 5-14 days, protected from light, until colonies formed. Following bacteria colony formation, strains were streak purified and glycerol stocks (50% marine media, 25% water, 25% glycerol) were stored at −80° C. in 2.0 mL cryovials. Upon expedition completion, glycerol stocks were transported on dry ice by airplane to be stored at −80° C. in Boston, MA.

Amplicon sequencing: 5-20 L of seawater was collected by CTD Rosette or by ROV. Seawater was vacuum filtered immediately following acquisition on the deck of the R/V Falkor using an industrial vacuum pump to concentrate all bacteria on a PES membrane (0.22 µm). Membranes were frozen at −80° C., transported and stored in liquid nitrogen, and sent to CD Genomics (Shirley, NY) for processing upon return. The bacteria community composition was determined from filter-extracted bacterial DNA using CD Genomics' sample processing pipeline. Briefly, genomic DNA was extracted and amplified with primers targeting the V3-V4 region of the 16S rRNA gene. DNA libraries were constructed from purified PCR products prior to sequencing on an Illumina MiSeq™ to generate 2×300 nt paired-end reads, yielding between 5661-49,031 sequences per sample.

Forward reads for each 16S amplicon were processed with the QIIME 2 pipeline (release 2020.2) [70], using the DADA2 algorithm for quality control and denoising [71]. Taxonomic annotations were assigned based on the SILVA 132 database [72]. Amplicon data analysis and plotting was conducted using Phyloseq [73] and ggplot2 [74] within R (V4.01) [75].

Sequencing bacterial strains from liquid culture: The phylogeny (genus) of streak purified deep-sea bacteria strains was determined by Sanger sequencing using the following protocol. Glycerol stocks were streaked on Difco™ marine agar 2216 plates and incubated at 4° C. for 5-7 days prior to colony formation. Colonies were picked and grown in 5 mL of sterile Difco™ marine broth 2216 at 14.5° C. for 36 hrs (Becton Dickenson, 279110). 3 mL of the 5 mL cultures were transferred to 30 mL marine media (1:10 dilution). After 48 hrs, 50 µl of each culture was boiled at 98° C. for 10 min and used as input template DNA for amplification of V regions within the bacterial genome by PCR. Amplified DNA was cleaned using the QIAquick™ PCR purification kit (Qiagen, 28106), and the final DNA concentration was determined by Nanodrop2000™. 20 ng/mL of amplified bacteria DNA was used as a template for Sanger sequencing (Genewiz, Inc.) to determine nucleotide composition within each amplified V region sequenced. The following two primer pairs were used to sequence the bacterial V regions: Forward:5'-AGAGTTT-GATYMTGGCTCAG-3' (SEQ ID NO: 1), Reverse 5'-ACG-GYTACCTTGTTACGACTT-3' (SEQ ID NO: 2) or Forward:5'-CCAGACTCCTACGGGAGGCAGC-3' (SEQ ID NO: 3), Reverse: 5'CTTGTGCGGGCCCCCGTCAATTC (SEQ ID NO: 4) [76]. Two primer pairs were employed to ensure that at least one successful PCR for each strain was accomplished for sequencing, given the unknown nature of the strains being sequenced. Using NCBI's nucleotide BLAST search tool, the nucleotide sequences generated were used to determine the genus of each bacteria strain streak purified.

*Moritella* genome sequencing and analysis: 1 mL (~2×10$^9$ bacteria) of *Moritella* sp. (OD600=1) was pelleted and resuspended in 600 µl Nuclei Lysis solution from Promega's Wizard™ Genomic DNA Purification Kit (A1120). Genomic DNA (gDNA) was prepared according to the manufacturer's protocol. Briefly, resuspended bacterial pellets were lysed by heating for 5 min at 80° C. Contaminating nucleotides were digested with 3 µl RNase A for 60 min at 37° C. Proteins were precipitated and the supernatant containing gDNA was harvested by centrifugation. The supernatant was mixed with isopropanol to precipitate gDNA which was subsequently washed with ethanol and pelleted. gDNA was resuspended in 100 µl Rehydration Solution and incubated overnight at 4° C. The following morning, final DNA concentrations were determined by Nanodrop2000™ and all samples were brought to a final concentration between 150-250 ng/ul in a final volume of 100 µl. gDNA samples were sent to the Microbial Genome Sequencing Center (MiGS; Pittsburgh, PA) for sequencing by both Oxford Nanopore and Illumina short-read sequencing. A hybrid genome assembly was performed at MiGS using the Unicycler™ pipeline [77], which determined that the final genome assemblies were circular and likely complete. The completeness of the final genome assemblies were determined using CheckM (V1.1.2) [78] and the relationship among genomes characterized with fastANI (V1.3) [58].

The phylogenetic relationship between these strains and other available *Moritella* was determined using a concatenated alignment of 120 single copy marker proteins [79]. These amino acid sequences were identified in the genomes, aligned, and concatenated using GTDB-TK (V1.3.0) [80]. The maximum likelihood tree was generated using RAxML (v8.2.9) [81] with the following options: raxmlHPC-PTHREADS-AVX -f a -m PROTGAMMAAUTO -p 12345 -x 12345 - #100. All phylogenetic trees were plotted using iTOL [82]. Pangenome analysis to compare gene content among *Moritella* strains was conducted using OrthoMCL (V2.0) [83] as implemented in Kbase [84].

To examine the lipid A synthesis pathway in *Moritella*, the conserved enzymes in the Raetz lipid A pathway for *E. coli* were identified in each sequenced genome. *E. coli* str.K-12 substr. MG1655 (NCBI 32NC_000913.3) was used for comparison. The protein sequence of each enzyme was aligned using mafft (V 7.273, in L-INS-i mode) [85], and the pathway-level phylogeny calculated from the concatenated sequences from each genome using RAxML as above. Protein identities for each protein were calculated from the individual alignments using the distance matrix calculated using the DistanceCalculator function in BioPython [86].

Cell lines: Wild type, tlr4 −/−, and casp11 −/− immortalized bone marrow derived macrophages (iBMDMs) were cultured in DMEM with 10% FBS, 1% Penicillin and Streptomycin, and 1% supplement of L-glutamine and sodium pyruvate. This media is referred to as complete DMEM. Prior to experimentation, cells were washed with PBS pH 7.4 and lifted with PBS pH 7.4 containing 2 mM EDTA. Otherwise, cells were passaged 1:10 every 2-3 days.

During routine passage, cells were washed with PBS pH 7.4 and lifted with 0.25% Trypsin. Trypsin was deactivated by adding serum containing media; after which cells were spun down and re-suspended in fresh media.

LPS and lipid A preparations: LPS was purified from *Moritella* strains using the Ernst laboratory's standard operating procedure (SOP) to extract LPS from bacteria [87] and eliminate the presence of contaminating lipoproteins [88]. One liter of each strain of *Moritella* was grown in sterile, filtered (0.22 um) Difco™ marine media 2216 (Becton Dickenson, 279110) at 14.5° C. to >1 OD. Crude LPS was extracted from each strain using the aqueous hot phenol method. This method relies on phenol and water to separate LPS from contaminating proteins, polysaccharides, and nucleic acids. Briefly, *Moritella* strains were pelleted by centrifugation, and each pellet was resuspended in 60 mL of endotoxin free ddH2O and mixed with equal volume 90% phenol (65° C.) for one hour, vortexing intermittently to liberate crude LPS molecules from the bacterial outer membrane. Following centrifugation, the aqueous layer containing the amphipathic LPS molecules was harvested from each preparation and placed on ice. An equal volume of endotoxin free ddH2O was added to the remaining phenol layer. Again, the bacteria/phenol/water mixtures were incubated at 65° C. with intermittent vortexing to liberate remaining LPS molecules. The preparations were centrifuged, and a second aqueous layer harvested. Aqueous layers were pooled and dialyzed against milliQ water for >48 hours, changing the water every 8-12 hours (or until odorless). Dialyzed LPS preparations (total volume~100 mL/prep) were shell frozen in sterile 250 mL glass flasks on dry ice and lyophilized for 2-4 days or until completely dry.

Contaminating nucleic acids and proteins were digested from the extracted LPS. To accomplish this, lyophilized LPS was resuspended in 10 mM Tris buffer pH 7.4 containing RNase A (25 μg/mL) and DNase I (100 μg/mL) and incubated at 37° C. for 120 min. Following the digestion of any contaminating nucleic acids, proteinase K (100 μg/mL) was added to the resuspended LPS at 37° C. for 60 min to digest the RNase A and DNase I as well as any other contaminating proteins. LPS was re-extracted from the Tris-mixture with water-saturated phenol. The aqueous layer containing LPS was harvested following centrifugation, dialyzed for 24 hours against milliQ water, and re-lyophilized.

Third, contaminating phospholipids were removed using four sequential chloroform: methanol (2:1 [vol/vol]; 20 mL total) washes. After chloroform:methanol washes, LPS preparations were resuspended in endotoxin-free ddH2O and re-lyophilized. Finally, further removal of remaining phospholipids was accomplished by resuspending lyophilized LPS in endotoxin-free ddH2O containing detergents TEA (0.2%) and sodium deoxycholate (0.5%). LPS was re-extracted with water-saturated phenol, and following centrifugation, the aqueous layer containing purified LPS was harvested and placed on ice. An equal volume of endotoxin free ddH2O containing detergents TEA (0.2%) and 10% DOC was added to the tube containing water saturated phenol, and the remaining, purified LPS was harvested following centrifugation. Pooled aqueous layers were then mixed with 30 mL of ice cold, 200 proof ethanol and sodium acetate (30 mM). Preparations were incubated overnight at −20° C. to precipitate purified LPS. Precipitated LPS was pelleted by centrifugation, washed 2× with ice cold 200 proof ethanol, resuspended in 5 mL of endotoxin-free ddH2O, and re-lyophilized in a pre-tared tube. Following lyophilization, purified LPS preparations were weighed (mg) and resuspended in endotoxin free ddH2O for use in experimental assays. LPS stocks were stored at −80° C. (for long term storage) and −20° C. (for experiments).

Hydrolysis and purification of *Moritella* lipid A from purified *Moritella* LPS was accomplished as follows. Purified LPS (2-8 mg/prep) from *Moritella* sp. Strains 5, 24, 28 and 36 were hydrolyzed in 2% acetic acid (pH 4.5) by heating for 1 hr at 100° C. Samples were frozen at −80° C. for 30 min and lyophilized overnight. The lyophilized lipid A product was washed in 95% ethanol, pelleted, and resuspended in 1 mL endotoxin free ddH2O in a pre-tared tube. Lipid A was again frozen at −80° C. and lyophilized overnight. The final product was weighed (mg), diluted to 1 mg/mL in endotoxin free ddH2O, and stocks were frozen (−20° C. and −80° C.). 1 mg/mL stock solutions were further diluted for use in all assays.

Pro-Q Emerald LPS/lipid A gel: 10 μg of purified *Moritella* LPS, *Moritella* lipid A, or *E. coli* O111:B4 LPS was mixed with 5× Laemmli buffer in 1.5 mL tubes and boiled for 5 min at 100° C. Samples were separated on a 10% SDS-polyacrylamide gel by electrophoresis. The resulting gel was fixed overnight at 4° C. on an orbital shaker in a solution containing 50% methanol and 5% acetic acid in milliQ ddH2O. Gel was washed twice in 3% acetic acid for 20 min on an orbital shaker at room temperature (RT) prior to being oxidized with periodic acid solution (Thermo Fisher, P20495). Gels were then washed three times in 3% acetic acid prior to staining with Pro-Q Emerald 300 Staining Solution for 120 min. After washing twice with acetic acid, gels were visualized with a 300 nm UV transilluminator.

Lipid A extraction for MALDI-TOF MS: Bacteria strains (n=50) were grown for 48-72 hours to OD600=1 in 5 mL marine media at 14.5° C. in a shaking incubator (180 rpm). Bacteria were pelleted and frozen for future extraction of lipid A. Frozen bacterial pellets were thawed on ice and lipid A was extracted from pellets using the isobutyric acid method [89]. Briefly, in screw-cap tubes, pellets were resuspended in 70% isobutyric acid and 1M ammonium hydroxide (5:3 [vol/vol]; 400 uL total). Tubes were incubated for 60 minutes at 100° C. with occasional vortexing to liberate the lipid A. Products were cooled on ice, centrifuged for 5 min at 8,000×g prior to harvesting the supernatant into new 1.5 mL tubes containing an equal volume (400 μl) of endotoxin-free ddH2O. Samples were frozen on dry ice for 30 min and lyophilized. Lyophilized samples were washed with methanol and lipid A was extracted from the remaining pellet with 50 μL of chloroform:methanol:water (3:1.5:0.25 [vol/vol]). The final lipid A product was mixed with Dowex™ beads and centrifuged for 5 min at 5,000×g. 1 ul of the lipid A product (supernatant) was resuspended with 1 μl of 10 mg/mL Norharmane™ matrix (Sigma, N6252, [48]) resuspended in chloroform: methanol (2:1 [vol/vol]) at a ratio of 1:1 and spotted on a steel re-usable MALDI plate. Spots were air dried and samples were analyzed on a Bruker Microflex™ mass spectrometer (Bruker Daltonics, Billerica, MA) in the negative-ion mode with reflectron mode. The spectrometer was calibrated with an electron spray tuning mix prior to every run (Agilent, Palo Alto, CA).

FLAT technique lipid A extraction for MALDI-TOF MS: Microbial colony smears or liquid samples were applied to a target location on a stainless steel MALDI plate. The target plate was incubated in a 70% citric acid buffer in a humidified chamber for 30 minutes at 110° C. The MALDI plate was washed with deionized water from a squeeze bottle, allowed to air dry, then 1 uL of Norharmane™ matrix solution was applied (10 mg/mL in 12:6:1, v/v/v chloroform/methanol/water) to each target location [51]. Following the method of Leung et al. [90], spectra were acquired from target locations in negative ion mode using a Microflex™ LRF MALDI-TOF MS (Bruker, Billerica MA) in reflectron mode with a limited mass range of 1,000-2,400 m z. Typically, 300 laser shots were summed to acquire each mass spectrum.

MALDI-TOF MS Data Analysis: Replicate mass-to-charge (m z) spectra data was generated for each lipid A. Bruker Daltonics flexAnalysis software was used to analyze all spectral data generated. Lipid A was classified as hexa- or hepta-acylated based on the m z ratio of its primary spectral peak. Based on previous MS-based studies on LPS lipid A [43, 44, 87, 91], peaks with m z ratios between 1650-1800 atomic mass units (amu) are predicted to by hexa-acylated, while peaks above 2000 amu are predicted to be hepta-acylated. Using these parameters, the acyl chain number present in the lipid A of each strain was predicted. In addition, the loss or addition of a phosphate to the di-glucosamine backbone was indicated by a m z change of 80 amu, and the addition of PEtn was indicated by a m z change 123amu. The presence of the outer membrane molecule, cardiolipin, was indicated by a m z ratio value of 1456 amu and single carbon loss/additions.

Gas Chromatography-Mass Spectrometry (GC-MS) analysis: Lipid A fatty acids were converted to fatty acid methyl esters as previously described [52]. Briefly, the bacterial cell pellet was incubated at 70° C. for 1 hour in 500 μl of 90% phenol and 500 μl of water. Samples were then cooled on ice for 5 minutes and centrifuged at 10,000 rpm for 10 minutes. The aqueous layer was collected and 500 μl of water was added to the lower (organic) layer and incubated again. This process was repeated thrice in total and all aqueous layers were pooled. Two ml of ethyl ether was added to the harvested aqueous layers, this mixture was then vortexed and centrifuged at 3,000 rpm for 5 minutes. The lower (organic) phase was collected, and 2 ml of ether were added back remaining aqueous phase. This process was carried out thrice in total. The collected organic layer was then frozen and lyophilized overnight. LPS fatty acids were converted to fatty methyl esters, in the presence of 10 μg pentadecanoic acid (Sigma, St. Louis, MO) as an internal standard, with 2 M methanolic HCl (Sigma, St. Louis, MO) at 90° C. for 18 hours. The resultant fatty acid methyl esters were analyzed and quantitated by gas chromatography-mass spectrometry (GC-MS) as follows.

GC-MS separation of derivatives was carried out on Shimadzu GC-MS 2010 with split injection with an injection temperature of 280° C. The initial oven temperature was 80° C. and held for 1 minute. The temperature was increased 25° C./minute until the oven reached 160° C. and held for 1 minute. The temperature was increased 10° C./minute until 265° C. and then increased 1° C./minute until 270° C. The temperature was held at 270° C. for 1 minute followed by a 10° C./minute increase to 295° C. where it was maintained for 1 minute. Total run time per sample was 25.2 minutes. Column head pressure was 100 kPa with an MSD detector. Transfer line temperature was 180° C. and mass range was m z 50-400. Identification of metabolites was performed using the standard National Institute of Standards and Technology NIST 08 standard and Golm Metabolome Database (GMD) mass spectra libraries and by comparison with authentic standards. Data processing was performed using a pipeline in KNIME. When required, GC-FAME standard (Matreya Bacterial Acid Methyl Esters, CP Mix, 1114) was used to identify individual fatty acids.

Murine macrophage stimulations and analysis: Flow cytometry for cell surface expression of CD14 & TLR4 monomers: $0.4 \times 10^6$ iBMDMs were seeded in complete DMEM 24-hours prior to lifting with PBS/EDTA and resuspension in complete DMEM. The following day, $0.5 \times 10^6$ iBMDMs were lifted and resuspended in 5 mL tubes in 2 mL of complete DMEM and treated with live bacteria (multiplicity of infection (MOI)=50) or purified LPS from *Moritella* strains or *E. coli* O111:B4 (Enzo Life Sciences, ALX-581-012) at the specified dose in triplicate. Following a 20-minute incubation at 37° C., 5% CO2, tubes were placed on ice, centrifuged at 400 g (4° C.), washed with 2 mL of cold PBS, and co-stained with antibodies to CD14 (eBioscience, 17-0141-82, dilute 1:100) and TLR4 monomers (Biolegend, 117610, dilute 1:100) for 60 minutes. Cells were centrifuged (4° C.) and washed twice with 2 mL of cold PBS. iBMDMs were resuspended in 0.5 mL of cold PBS and CD14 and TLR4 monomer cell surface expression were measured by flow cytometry using the APC (CD14) and Pe/Cy7 (TLR4) laser channels on the FACs Canto II or FACs Fortessa. Samples were normalized to unstained samples in Flowlo. Flow cytometry data were processed using FlowJo Version9.3.2 and data presentation and analysis were performed in Prism.

Statistical analysis in Prism: The 100 ng/mL dose from purified *Moritella* LPS preps were compared to the 100 ng/mL dose of purified *E. coli* O111:B4 LPS. One-way analysis of variance (ANOVA) was performed assuming Gaussian distribution, no pairing, and multiple comparisons *E. coli* (100 ng/mL). Equal standard deviation was not assumed, and Brown-Forsythe and Welsh ANOVA tests were performed to determine if there were significant differences between CD14 or TLR4 MFI in iBMDMs after treatment with *Moritella* LPS and *E. coli* LPS at the 100 ng/mL dose. Significance was reported to a 99% confidence interval ($p<0.01$).

Flow cytometry for intracellular TNFα accumulation: $0.4 \times 10^6$ iBMDMs were seeded in complete DMEM 24-hours prior to lifting with PBS/EDTA and resuspension in complete DMEM. $0.5 \times 10^6$ iBMDMs were pre-treated for 30 min with brefeldin A (BFA) and incubated with 100 ng/mL *Moritella* LPS, *Moritella* lipid A, or *E. coli* O111:B4 LPS for 3.5 hrs. Cells were centrifuged, placed on ice, and washed with cold PBS prior to fixation for 60 min (eBioscience, 88-8824-00). Following a cold PBS wash, cells were resuspended in 1× permeabilization buffer (eBioscience, 88-8824-00) containing antibody to TNFα (Biolegend, 506308, dilute 1:100) and incubated overnight at 4° C., protected from light. The following morning, iBMDMs were washed twice with cold PBS and were resuspended in 0.5 mL cold PBS. Intracellular TNFα accumulation was measured by flow cytometry using the APC laser channel on the FACs Canto II. Samples were normalized to unstained samples in FlowJo Version9.3.2. Flow cytometry data were processed using FlowJo Version9.3.2 and data presentation and analyses were performed in Prism.

Statistical analysis in Prism: One-way analysis of variance (ANOVA) was performed assuming Gaussian distribution, no pairing, and multiple comparisons to purified *E. coli* O111:B4 LPS. Equal standard deviation was not assumed, and Brown-Forsythe and Welsh ANOVA tests were performed to determine if there were significant differences in TNFα MFI in iBMDMs after treatment with *Moritella* LPS and *E. coli* LPS at the 100 ng/mL dose. Significance was reported to a 99% confidence interval ($p<0.01$).

Lactase dehydrogenase (LDH) release and gasdermin D (GSDMD) cleavage: $1 \times 10^6$ iBMDMs per condition were seeded in complete DMEM and primed with 10 ng/mL of Pam3Csk overnight. Cells were lifted the following day with PBS/EDTA and washed with PBS prior to being resuspended in 130 µl electroporation resuspension buffer R (Neon Transfection Kit, ThermoFisher, MPK10096) in 1.5 mL tubes. iBMDMs were electroporated for 20 ms, 1400V, 2 pulses with 1 µg of purified *Moritella* LPS, *Moritella* lipid A, or *E. coli* O111:B4 LPS according to the manufacturer's protocol. After electroporation, cells were re-suspended in 2 mL complete medium without antibiotics and plated in triplicate in 200 µl aliquots in a 96-well tissue culture dish that was then incubated at 37° C., 5% CO2 for 3 hours. 50 µl of media was harvested from each well and total LDH was measured according to the manufacturer's protocol (ThermoFisher, C20301). Absorbance data at 490 nm and 680 nm were acquired in triplicate by plate reader (Tecan, model Spark 10M). 680 nm data was aligned to and subtracted from 490 nm data in Microsoft Excel to generate final absorbance data points for LDH release. Final data presentation and analyses were performed in Prism.

The remainder of iBMDMs were plated in one well of a 12-well dish and lysed after 3 hours. Whole cell lysates were prepared with 1× Laemmli buffer. Lysates were needled and boiled for 5 min at 100° C. prior to electrophoresis. Samples were electrophoresed on a 12% SDS-PAGE gel and immunoblotted for GSDMD using standard molecular techniques (Abcam, 209845, dilute 1:1000).

Statistical analysis in Prism: iBMDMs electroporated with purified *Moritella* LPS were compared to iBMDMs electroporated with purified *E. coli* 011:4 LPS. iBMDMS electroporated with purified *Moritella* lipid A were compared to iBMDMs electroporated with purified *Moritella* LPS. One-way analysis of variance (ANOVA) was performed assuming Gaussian distribution, no pairing, and multiple comparisons *E. coli* (100 ng/mL). Equal standard deviation was not assumed, and Brown-Forsythe and Welsh ANOVA tests were performed to determine if there were significant differences between conditions analyzed. Significance was reported to a 99.9% confidence interval ($p<0.001$).

Western analysis for phosphorylation of STAT1: $0.4 \times 10^6$ iBMDMs/well were seeded in 6-well dishes in complete DMEM 24-hours prior to treatment with 100 ng/mL purified *Moritella* LPS or *E. coli* O111:B4 LPS. After 2.5 hrs, whole cell lysates were prepared with NP40 lysis buffer (1% NP40, 50 mM Tris-HCl (pH 7.4), 150 mM NaCl) and incubated for 20 min on ice. Protease inhibitors were added to lysis buffer just before cell lysis. Nuclei were removed by centrifugation at 17,000×g for 5 min at 4° C. Aqueous layers were harvested, resuspended with 5× Laemmli buffer, and boiled for 5 min at 100° C. Samples were electrophoresed on a 12% SDS-PAGE gel and immunoblotted for total STAT1 or phosphorylated STAT1 using standard molecular techniques. The following antibodies were used: anti-STAT1 (Becton Dickenson, 610115, 1:5000), anti-pSTAT1 p701 (Becton Dickenson, 612132, dilute 1:2000).

In vitro caspase-11 (CASP11)-LPS interactions: The binding capacity of LPS from *Moritella* to murine CASP11 was evaluated by the biotinylated *E. coli* LPS pull down assay. 293T cells were plated at 20% confluency in three, 10 cm tissue culture plates. Each plate was transfected with 5 µg plasmid DNA for wildtype (WT) CASP11 with an HA tag. After 48 hours, lysates expressing CASP11-HA were harvested in 700 ul NP40 lysis buffer (1% NP40, 50 mM Tris-HCl (pH 7.4), 150 mM NaCl) and incubated for 20 min on ice. Protease inhibitors were added to lysis buffer just before cell lysis. Nuclei were removed by centrifugation at 17,000×g for 5 min at 4° C. The aqueous layers from the three plates were harvested and pooled. 50 ul of the pooled lysate was prepared as an input fraction with 5× Laemmli buffer, and the remainder of the pooled lysate was divided into n=7 1.5 mL tubes, 300 ul aliquots of pooled lysate each.

293T lysates were pre-treated with 5 ug non-biotinylated LPS (*E. coli* or *Moritella*) for 30 minutes prior to an overnight incubation with 1 ug of biotinylated *E. coli* LPS on the nutator at 4° C. The following morning, 50 ul of neutravidin beads were added to each lysate, and lysates were spun an additional 3 hours on the nutator at 4° C. Beads were lysed in 50 ul 1× Laemmli buffer by boiling for 5 minutes at 100° C. CASP11-HA attached to biotinylated LPS and captured by neutravidin beads was evaluated by western blot analysis (Roche, 11867423001, dilute 1:1000).

In vivo LPS challenge: 10-week old mice were injected intraperitoneally with 1 mg/kg of LPS purified from *Moritella* sp. strains 5, 24, 28 or 36. Blood samples were collected 4 hours post injection and plasma were obtained by centrifugation at 2000 g for 10 min. IL-6 and TNFα plasma concentrations were measured by ELISA (Biolegend). All animal procedures were approved by the Institutional Animal Care and Use Committee.

Human THP1 cell stimulations and analysis: Human THP1 cells were cultured in complete RPMI and differentiated with 50 ng/mL PMA for 48 hours prior to assessing pro-IL1β and TNFα after stimulations with 50 ng/mL or 100 ng/mL *E. coli* or *Moritella* LPS, respectively.

Western analysis for production of pro-IL1β: THP1 cells were lifted with PBS/EDTA. $1 \times 10^6$ cells were resuspended in 1 mL complete RPMI and incubated with 50 ng/mL purified *Moritella* sp. LPS or *E. coli* O111:B4 LPS for 2.5 hours. Whole cell lysates were prepared with 1× Laemmli buffer. Lysates we needled and boiled for 5 min at 100° C. prior to electrophoresis. Samples were electrophoresed on a 12% SDS-PAGE gel and immunoblotted for pro-IL1β using standard molecular techniques (Genetex, GTX74034, dilute 1:1000)

Flow cytometry for intracellular TNFα accumulation: THP1 cells were lifted with PBS/EDTA and resuspended in complete RPMI. $1 \times 10^6$ THP1 cells were pre-treated for 30 min with 10 ug/mL BFA and incubated with 100 ng/mL purified *Moritella* sp. LPS or *E. coli* O111:B4 LPS for 5 hrs. Cells were centrifuged, placed on ice, and washed with cold PBS prior to fixation for 60 min (eBioscience, 88-882400). Following a cold PBS wash, cells were resuspended in 1× permeabilization buffer (eBioscience, 888824-00) containing antibody to TNFα (Biolegend, 502906, dilute 1:100) and incubated overnight at 4° C., protected from light. The following morning, THP1 cells were washed twice with cold PBS and were resuspended in 0.5 mL cold PBS. Intracellular TNFα accumulation was measured by flow cytometry using the FITC laser channel on the FACs Canto II. Samples were normalized to unstained samples in FlowJo Version9.3.2. Flow cytometry data were processed using FlowJo Version9.3.2 and data presentation and analyses were performed in Prism.

Statistical analysis in Prism: One-way analysis of variance (ANOVA) was performed assuming Gaussian distribution, no pairing, and multiple comparisons to purified *E. coli* O111:B4 LPS. Equal standard deviation was not assumed, and Brown-Forsythe and Welsh ANOVA tests were performed to determine if there were significant differences in TNFα MFI in THP1 cells after treatment with *Moritella* sp. LPS and *E. coli* LPS at the 50 ng/mL dose. Significance was reported to a 99.9% confidence interval ($p<0.001$).

LDH release from human THP1 cells: $2\times10^6$ THP1 cells per condition were seeded in complete RPMI and primed with 10 ng/mL of Pam3Csk overnight. Cells were washed with PBS prior to being resuspended in 20 µl electroporation resuspension buffer T (Neon Transfection Kit, ThermoFisher, MPK10096) in 0.5 mL tubes. THP1 cells were electroporated for 10 ms, 1400V, 3 pulses with 1 µg of purified *Moritella* sp. LPS, or purified *E. coli* O111::B4 LPS according to the manufacturer's protocol. After electroporation, cells were re-suspended in 2 mL complete medium without antibiotics and plated in 200 µl aliquots in a 96-well tissue culture dish that was then incubated at 37° C., 5% $CO_2$ for 2.5 hours. 50 µl of media was harvested from each well and total LDH was measured according to the manufacturer's protocol (ThermoFisher, C20301). Absorbance data at 490 nm and 680 nm were acquired in triplicate by plate reader (Tecan, model Spark 10M). 680 nm data was aligned to and subtracted from 490 nm data in Microsoft Excel to generate final absorbance data points for LDH release. Final data presentation and analyses were performed in Prism.

Statistical analysis in Prism: THP1 cells electroporated with purified *Moritella* sp. LPS were compared to THP1 cells electroporated with purified *E. coli* O111:B4 LPS. One-way analysis of variance (ANOVA) was performed assuming Gaussian distribution, no pairing, and multiple comparisons *E. coli* (100 ng/mL). Equal standard deviation was not assumed, and Brown-Forsythe and Welsh ANOVA tests were performed to determine if there were significant differences between conditions analyzed. Significance was reported to a 99% confidence interval ($p<0.01$).

HEK-Blue 293T reporter cell line (InvivoGen, hkb-htlr4): In a 96-well plate, $0.5\times10^5$ cells/well were plated in culture media for real-time detection of secreted alkaline phosphatase (InvivoGen, hb-det2). In triplicate, 100 ng/ml of purified *Moritella* LPS or *E. coli* O111:B4 LPS was added to each well. Plates were incubated for 24 hours at 37° C., 5% CO2. Secreted alkaline phosphatase was determined by reading the absorbance at 635 nm (Tecan, model Spark 10M).

Statistical analysis in Prism: One-way analysis of variance (ANOVA) was performed assuming Gaussian distribution, no pairing, and multiple comparisons to purified *E. coli* O111:B4 LPS. Equal standard deviation was not assumed, and Brown-Forsythe and Welsh ANOVA tests were performed to determine if there were significant differences in absorbance between 293T cells incubated with *Moritella* LPS and *E. coli* LPS. Significance was reported to a 99.9% confidence interval ($p<0.001$).

*Limulus* Amebocyte Lysate Pyrochrome assay: In triplicate, 20 ng/mL of purified *Moritella* LPS, *Moritella* lipid A, or *E. coli* O111:B4 LPS was sequentially diluted 10-fold from 20 ng/mL to 20 µg/mL in a 96-well plate. The total volume in each well was 50 1l/well. PBS was used as a negative control. Pyrochrome reagent was resuspended in Glucashield buffer according to the manufacturer's protocol (Associates of Cape Cod, CG1500). 50 µl of Pyrochrome reagent (1:1 [vol/vol]) was added to each well for a final volume of 100 µl/well. The final concentrations of LPS/lipid A measured in triplicate were: 10 ng/mL, 1 ng/mL, 100 µg/mL and 10 µg/mL. Absorbance was measured at 405 nm at 37° C. for 60 minutes every 5 min by plate reader (Tecan, model Spark 10M). Data was analyzed when maximum absorbance was reached at 1 ng/mL. Data presentation and analyses were performed in Prism.

Statistical analysis in Prism: One-way analysis of variance (ANOVA) was performed assuming Gaussian distribution, no pairing, and multiple comparisons to either purified *E. coli* LPS or purified *Moritella* LPS. Equal standard deviation was not assumed, and Brown-Forsythe and Welsh ANOVA tests were performed to determine if there were significant differences between conditions analyzed. Significance was reported to a 99.9% confidence interval ($p<0.001$).

Data Availability: All genomes were deposited in NCBI Genbank under BioProject PRJNA639995 (accession numbers in Table 2). 16S amplicon data are available from the NCBI Sequence Read Archive, Study SRP267655. (Available on the world wide web at dataview.ncbi.nlm.nih.gov/object/PRJNA639995?reviewer=ck2khf837 mocafu62499 m8ic3e) Bacterial strains are available upon request, with written permission from the Kiribati government.

The invention claimed is:

1. A composition comprising an effective amount of an immunostimulatory lipid A molecule engineered from a lipopolysaccharide (LPS) purified from an immunostimulatory strain of the genus *Moritella* and an agent, wherein the agent is a protein, a drug, a prodrug, a vitamin, a neutraceutical, a cytokine, a chemokine, an enzyme, a growth factor, a nucleic acid, an imaging agent, a bioactive molecule, or a diagnostic agent.

2. The composition of claim 1, wherein the lipid A is capable of activating Toll-like receptor signaling, caspase signaling, or a combination thereof.

3. The composition of claim 1, wherein the strain of the genus *Moritella* is a species selected from the group consisting of *Moritella oceanus* and *Moritella rawaki*.

4. The composition of claim 1, wherein the nucleic acid is DNA, RNA, mRNA, dsRNA, dsRNA, SiRNA, miRNA, or ShRNA.

5. A vaccine formulation comprising an effective amount of an immunostimulatory lipid A molecule engineered from a lipopolysaccharide (LPS) purified from an immunostimulatory strain of the genus *Moritella* and an antigen, wherein the strain of the genus *Moritella* is a species selected from the group consisting of *Moritella oceanus* and *Moritella rawaki* and wherein the effective amount is sufficient to stimulate an immune response against the antigen.

6. A method of inducing an immune response to an antigen in a mammalian subject, the method comprising administering to the subject an effective amount of a vaccine comprising an antigen and an effective amount of an immunostimulatory lipid A molecule engineered from a lipopolysaccharide (LPS) purified from an immunostimulatory strain of the genus *Moritella*, thereby inducing the immune response to the antigen in the subject, wherein the immune response to the antigen is increased by at least 10% compared to a vaccine comprising the antigen administered in the absence of the immunostimulatory lipid A molecule.

7. The method of claim 6, wherein the immunostimulatory lipid A molecule comprises five, six, or seven acyl chains.

8. The method of claim 7, wherein no more than one of the five, six, or seven acyl chains has a length of at least 16 carbons (C16).

9. The method of claim 8, wherein each of the five, six, or seven acyl chains has a length of 12-14 carbons (C12-C14).

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agagtttgat ymtggctcag                                            20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acggytacct tgttacgact t                                          21

```
<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccagactcct acgggaggca gc                                              22

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cttgtgcggg cccccgtcaa ttc                                             23
```